US008663129B2

(12) United States Patent
Allen et al.

(10) Patent No.: US 8,663,129 B2
(45) Date of Patent: Mar. 4, 2014

(54) BLOOD COLLECTION SAFETY DEVICES AND METHODS OF USE AND MANUFACTURE

(75) Inventors: David P. Allen, Newport Beach, CA (US); Edward P. Browka, Chapel Hill, NC (US); Jessie Delgado, Durham, NC (US); Matthew R. Penny, Cary, NC (US); David L. Foshee, Apex, NC (US); Theodore J. Mosler, Raleigh, NC (US)

(73) Assignee: Sta-Med, LLC, Irvine, CA (US)

( * ) Notice: Subject to any disclaimer, the term of this patent is extended or adjusted under 35 U.S.C. 154(b) by 0 days.

(21) Appl. No.: 13/483,878

(22) Filed: May 30, 2012

(65) Prior Publication Data

US 2012/0323142 A1 Dec. 20, 2012

Related U.S. Application Data

(60) Provisional application No. 61/491,830, filed on May 31, 2011, provisional application No. 61/596,684, filed on Feb. 8, 2012, provisional application No. 61/615,783, filed on Mar. 26, 2012.

(51) Int. Cl.
*A61B 10/00* (2006.01)

(52) U.S. Cl.
USPC ............................ 600/576; 600/573; 600/579

(58) Field of Classification Search
USPC .......... 600/576, 579; 604/6.15, 6.16, 36, 264, 604/272, 403, 411
See application file for complete search history.

(56) References Cited

U.S. PATENT DOCUMENTS

| 2,460,641 A | 2/1949 | Kleiner |
| 2,876,770 A | 3/1959 | White |
| 3,134,380 A | 5/1964 | Armao |

(Continued)

FOREIGN PATENT DOCUMENTS

| DE | 20 2007 001717 | 7/2007 |
| EP | 0329038 A1 * | 8/1989 |

(Continued)

OTHER PUBLICATIONS

International Search Report and Written Opinion in corresponding Application No. PCT/US2012/039893, mailed Sep. 7, 2012, 10 pages.

(Continued)

*Primary Examiner* — Sean Dougherty
*Assistant Examiner* — Daniel Cerioni
(74) *Attorney, Agent, or Firm* — Knobbe, Martens, Olson & Bear, LLP

(57) ABSTRACT

An automatically locking safety device, e.g., for use in a blood collection procedure, can include a housing, first and second needle covers that are at least partly received in the housing, and a needle that is at least partly received in at least one of the first and second needle covers. The needle can include a proximal tip configured for placement into a patient and a distal tip configured for placement into a blood collection vial. In some embodiments, the first and second needle covers are biased by a biasing member. In some cases, one or both of the first and second needle covers can be locked to prevent axial movement thereof after the blood collection procedure. In certain embodiments, a distal end of the device is configured to connect with a medical connector, such as a needleless IV access device.

21 Claims, 68 Drawing Sheets

(56) References Cited

U.S. PATENT DOCUMENTS

| | | | |
|---|---|---|---|
| 3,299,891 A | 1/1967 | Smeton | |
| 3,929,165 A | 12/1975 | Diebolt et al. | |
| 4,127,131 A | 11/1978 | Vaillancourt | |
| 4,205,675 A | 6/1980 | Vaillancourt | |
| 4,276,170 A | 6/1981 | Vaillancourt | |
| 4,318,402 A | 3/1982 | Vaillancourt | |
| 4,326,569 A | 4/1982 | Vaillancourt | |
| 4,349,035 A | 9/1982 | Thomas et al. | |
| 4,416,290 A | 11/1983 | Lutkowski | |
| 4,492,313 A | 1/1985 | Touzani | |
| 4,511,359 A | 4/1985 | Vaillancourt | |
| 4,525,157 A | 6/1985 | Vaillancourt | |
| 4,525,374 A | 6/1985 | Vaillancourt | |
| 4,585,435 A | 4/1986 | Vaillancourt | |
| 4,610,683 A | 9/1986 | Vaillancourt | |
| 4,617,012 A | 10/1986 | Vaillancourt | |
| 4,636,200 A | 1/1987 | Vaillancourt | |
| 4,636,313 A | 1/1987 | Vaillancourt | |
| 4,645,495 A | 2/1987 | Vaillancourt | |
| 4,652,256 A | 3/1987 | Vaillancourt | |
| 4,655,750 A | 4/1987 | Vaillancourt | |
| 4,678,462 A | 7/1987 | Vaillancourt | |
| 4,682,607 A | 7/1987 | Vaillancourt | |
| 4,702,739 A | 10/1987 | Milorad | |
| 4,704,177 A | 11/1987 | Vaillancourt | |
| 4,723,955 A | 2/1988 | Vaillancourt | |
| 4,725,267 A | 2/1988 | Vaillancourt | |
| 4,743,243 A | 5/1988 | Vaillancourt | |
| 4,773,458 A | 9/1988 | Touzani | |
| 4,795,432 A | 1/1989 | Karczmer | |
| 4,801,296 A | 1/1989 | Vaillancourt | |
| 4,804,371 A | 2/1989 | Vaillancourt | |
| 4,813,937 A | 3/1989 | Vaillancourt | |
| 4,830,914 A | 5/1989 | Vaillancourt | |
| 4,834,108 A | 5/1989 | Vaillancourt | |
| 4,850,977 A | 7/1989 | Bayless | |
| 4,850,996 A | 7/1989 | Cree | |
| 4,863,431 A | 9/1989 | Vaillancourt | |
| 4,867,743 A | 9/1989 | Vaillancourt | |
| 4,887,998 A | 12/1989 | Martin et al. | |
| 4,894,055 A | 1/1990 | Sudnak | |
| 4,904,248 A | 2/1990 | Vaillancourt | |
| 4,943,281 A | 7/1990 | Kothe | |
| 4,971,068 A | 11/1990 | Sahi | |
| 5,011,479 A | 4/1991 | Le et al. | |
| 5,015,240 A | 5/1991 | Soproni et al. | |
| 5,026,356 A | 6/1991 | Smith | |
| 5,057,086 A | 10/1991 | Dillard, III et al. | |
| 5,069,225 A | 12/1991 | Okamura | |
| 5,104,384 A | 4/1992 | Parry | |
| 5,104,385 A | 4/1992 | Huband | |
| 5,125,908 A | 6/1992 | Cohen | |
| 5,180,370 A | 1/1993 | Gillespie | |
| 5,222,502 A | 6/1993 | Kurose | |
| 5,279,584 A | 1/1994 | Dillard, III et al. | |
| 5,292,314 A | 3/1994 | D'Alessio et al. | |
| 5,295,975 A | 3/1994 | Lockwood, Jr. | |
| 5,300,045 A | 4/1994 | Plassche, Jr. | |
| 5,303,713 A | 4/1994 | Kurose | |
| 5,308,332 A | 5/1994 | Dillard, III et al. | |
| 5,336,187 A | 8/1994 | Terry et al. | |
| 5,348,544 A | 9/1994 | Sweeney et al. | |
| 5,360,409 A | 11/1994 | Boyd, III et al. | |
| 5,364,372 A * | 11/1994 | Danks et al. | 604/264 |
| 5,368,568 A | 11/1994 | Pitts et al. | |
| 5,389,085 A | 2/1995 | O'Alessio et al. | |
| 5,403,286 A | 4/1995 | Lockwood, Jr. | |
| 5,415,645 A | 5/1995 | Friend et al. | |
| 5,423,765 A | 6/1995 | Hollister | |
| 5,462,533 A | 10/1995 | Daugherty | |
| 5,472,430 A | 12/1995 | Vaillancourt | |
| 5,514,116 A | 5/1996 | Vaillancourt | |
| 5,520,193 A | 5/1996 | Suzuki et al. | |
| 5,578,011 A | 11/1996 | Shaw | |
| 5,582,597 A | 12/1996 | Brimhall et al. | |
| 5,601,536 A | 2/1997 | Crawford et al. | |
| 5,609,577 A | 3/1997 | Haber et al. | |
| 5,632,733 A | 5/1997 | Shaw | |
| 5,651,480 A | 7/1997 | Piepenstock | |
| 5,656,031 A | 8/1997 | Thorne et al. | |
| 5,688,241 A | 11/1997 | Asbaghi | |
| 5,795,336 A | 8/1998 | Romano et al. | |
| 5,823,973 A * | 10/1998 | Racchini et al. | 600/573 |
| 5,824,001 A | 10/1998 | Erskine | |
| 5,893,845 A | 4/1999 | Newby et al. | |
| 5,935,104 A | 8/1999 | Janek et al. | |
| 5,964,739 A | 10/1999 | Champ | |
| 5,976,111 A | 11/1999 | Hart | |
| 5,984,899 A | 11/1999 | D'Alessio et al. | |
| 6,024,727 A * | 2/2000 | Thorne et al. | 604/195 |
| 6,090,077 A | 7/2000 | Shaw | |
| RE36,885 E | 9/2000 | Blecher et al. | |
| 6,186,980 B1 | 2/2001 | Brunel | |
| 6,203,529 B1 | 3/2001 | Gabriel et al. | |
| 6,379,336 B1 | 4/2002 | Asbaghi et al. | |
| 6,468,383 B2 | 10/2002 | Kundel | |
| 6,524,279 B1 | 2/2003 | Shields | |
| 6,572,584 B1 | 6/2003 | Shaw et al. | |
| 6,629,959 B2 | 10/2003 | Kuracina et al. | |
| 6,648,856 B1 | 11/2003 | Argento | |
| 6,648,858 B2 | 11/2003 | Asbaghi | |
| 6,699,221 B2 | 3/2004 | Vaillancourt | |
| 6,706,000 B2 * | 3/2004 | Perez et al. | 600/583 |
| 6,712,792 B2 | 3/2004 | Leong | |
| 6,719,730 B2 | 4/2004 | Jansen et al. | |
| 6,733,465 B1 * | 5/2004 | Smutney et al. | 600/576 |
| 6,761,706 B2 | 7/2004 | Vaillancourt | |
| 6,796,967 B2 * | 9/2004 | Jensen | 604/197 |
| 6,808,507 B2 | 10/2004 | Roser | |
| 6,855,129 B2 | 2/2005 | Jensen et al. | |
| 6,860,871 B2 | 3/2005 | Kuracina et al. | |
| 6,869,415 B2 | 3/2005 | Asbaghi | |
| 6,872,190 B1 | 3/2005 | Denis et al. | |
| 6,905,483 B2 | 6/2005 | Newby et al. | |
| 6,926,697 B2 | 8/2005 | Malenchek | |
| 6,966,898 B1 | 11/2005 | Pouget et al. | |
| 6,984,223 B2 | 1/2006 | Newby et al. | |
| 6,986,760 B2 | 1/2006 | Giambattista et al. | |
| 6,997,913 B2 | 2/2006 | Wilkinson | |
| 7,037,294 B2 | 5/2006 | Luther et al. | |
| 7,083,600 B2 | 8/2006 | Meloul | |
| 7,101,351 B2 | 9/2006 | Crawford et al. | |
| 7,160,267 B2 | 1/2007 | Brown | |
| 7,186,239 B2 | 3/2007 | Woehr | |
| 7,198,617 B2 | 4/2007 | Millerd | |
| 7,201,740 B2 | 4/2007 | Crawford | |
| 7,226,432 B2 | 6/2007 | Brown | |
| 7,306,566 B2 * | 12/2007 | Raybuck | 600/576 |
| 7,314,464 B2 | 1/2008 | Giambattista et al. | |
| 7,354,422 B2 * | 4/2008 | Riesenberger et al. | 604/198 |
| 7,357,783 B2 | 4/2008 | Millerd | |
| 7,361,160 B2 | 4/2008 | Hammann et al. | |
| 7,396,343 B2 | 7/2008 | Brown | |
| 7,469,458 B1 * | 12/2008 | Starnes | 29/428 |
| 7,524,308 B2 | 4/2009 | Conway | |
| 7,530,967 B2 | 5/2009 | Brown | |
| 7,615,033 B2 | 11/2009 | Leong | |
| 7,648,480 B2 | 1/2010 | Bosel et al. | |
| 7,666,164 B2 | 2/2010 | Giambattista et al. | |
| 7,678,077 B2 * | 3/2010 | Harris et al. | 604/117 |
| 7,736,322 B2 * | 6/2010 | Roe et al. | 600/583 |
| 7,766,879 B2 | 8/2010 | Tan et al. | |
| 7,811,261 B2 | 10/2010 | Rubinstein et al. | |
| 7,815,611 B2 | 10/2010 | Giambattista et al. | |
| 7,828,817 B2 * | 11/2010 | Belef et al. | 606/213 |
| 7,922,698 B2 * | 4/2011 | Riesenberger et al. | 604/192 |
| 7,927,314 B2 | 4/2011 | Kuracina et al. | |
| 8,162,882 B2 | 4/2012 | Rubinstein et al. | |
| 8,211,036 B2 * | 7/2012 | Schraga | 600/583 |
| 8,308,691 B2 * | 11/2012 | Woehr et al. | 604/167.01 |
| 8,419,688 B2 * | 4/2013 | Woehr et al. | 604/167.01 |
| 8,435,738 B2 * | 5/2013 | Holmes | 435/6.1 |
| 8,460,247 B2 * | 6/2013 | Woehr et al. | 604/164.08 |
| 8,475,739 B2 * | 7/2013 | Holmes et al. | 422/509 |

(56) References Cited

U.S. PATENT DOCUMENTS

| | | | |
|---|---|---|---|
| 8,486,027 B2 * | 7/2013 | Findlay et al. | 604/187 |
| 2003/0050608 A1 | 3/2003 | Brown | |
| 2003/0078548 A1 | 4/2003 | Kobayashi | |
| 2003/0114797 A1 | 6/2003 | Vaillancourt et al. | |
| 2003/0144632 A1 | 7/2003 | Hammann et al. | |
| 2003/0212369 A1 | 11/2003 | Kobayashi | |
| 2004/0087914 A1 * | 5/2004 | Bryan et al. | 604/264 |
| 2004/0112457 A1 * | 6/2004 | Norton et al. | 141/26 |
| 2004/0204662 A1 * | 10/2004 | Perez et al. | 600/583 |
| 2004/0210197 A1 * | 10/2004 | Conway | 604/198 |
| 2004/0222579 A1 | 11/2004 | Adoline et al. | |
| 2004/0254499 A1 * | 12/2004 | Smutney et al. | 600/576 |
| 2005/0267410 A1 | 12/2005 | Koska | |
| 2005/0277893 A1 | 12/2005 | Liversidge | |
| 2006/0079847 A1 * | 4/2006 | Crawford | 604/192 |
| 2006/0189933 A1 | 8/2006 | Alheidt et al. | |
| 2006/0224122 A1 | 10/2006 | Bosel et al. | |
| 2006/0229570 A1 * | 10/2006 | Lovell et al. | 604/218 |
| 2007/0060893 A1 | 3/2007 | Mahurkar | |
| 2007/0129683 A1 | 6/2007 | Brungardt | |
| 2007/0179451 A1 | 8/2007 | Sprinkle et al. | |
| 2007/0265566 A1 | 11/2007 | Simpson et al. | |
| 2007/0293819 A1 | 12/2007 | Giambattista et al. | |
| 2008/0319346 A1 | 12/2008 | Crawford et al. | |
| 2009/0204026 A1 | 8/2009 | Crawford et al. | |
| 2009/0227950 A1 | 9/2009 | Jensen et al. | |
| 2009/0227956 A1 | 9/2009 | Emmott et al. | |
| 2009/0299295 A1 * | 12/2009 | Rubinstein et al. | 604/198 |
| 2010/0004602 A1 | 1/2010 | Nord et al. | |
| 2010/0010372 A1 | 1/2010 | Brown et al. | |
| 2010/0042053 A1 | 2/2010 | Dillard, III | |
| 2010/0087784 A1 | 4/2010 | Bosel et al. | |
| 2010/0160865 A1 | 6/2010 | Zeltzer et al. | |
| 2010/0241029 A1 * | 9/2010 | Mahurkar | 600/577 |
| 2010/0262038 A1 | 10/2010 | Tan et al. | |
| 2010/0280488 A1 * | 11/2010 | Pruitt et al. | 604/506 |
| 2010/0286558 A1 * | 11/2010 | Schraga | 600/576 |
| 2010/0292654 A1 * | 11/2010 | Schraga | 604/198 |
| 2010/0298770 A1 | 11/2010 | Rubinstein et al. | |
| 2011/0077600 A1 | 3/2011 | Uchida et al. | |
| 2011/0106148 A1 * | 5/2011 | Ginn et al. | 606/213 |
| 2011/0152832 A1 * | 6/2011 | Foshee et al. | 604/506 |
| 2011/0257603 A1 | 10/2011 | Ruan et al. | |
| 2011/0270198 A1 | 11/2011 | Perot et al. | |
| 2011/0276014 A1 * | 11/2011 | Saitoh et al. | 604/272 |
| 2012/0071790 A1 * | 3/2012 | Mahurkar | 600/577 |
| 2012/0277628 A1 * | 11/2012 | Schraga | 600/576 |
| 2012/0289930 A1 | 11/2012 | Rubinstein | |

FOREIGN PATENT DOCUMENTS

| | | |
|---|---|---|
| EP | 2298394 A1 | 3/2011 |
| GB | 732313 | 6/1955 |
| WO | WO 02/09797 | 2/2002 |
| WO | WO 02/083205 | 10/2002 |
| WO | WO 03/066141 | 8/2003 |
| WO | WO 2004/069301 | 8/2004 |
| WO | WO 2004/069302 | 8/2004 |
| WO | WO 2004/110535 | 12/2004 |
| WO | WO 2006/029003 | 3/2006 |
| WO | WO 2009/039022 | 3/2009 |
| WO | WO 2009/148969 | 12/2009 |
| WO | WO 2009/154131 | 12/2009 |
| WO | WO 2010/019201 | 2/2010 |
| WO | WO 2011/162913 | 12/2011 |
| WO | WO 2012/166746 A1 | 12/2012 |

OTHER PUBLICATIONS

U.S. Appl. No. 13/448,156, filed Apr. 16, 2012, Rubinstein et al.
"BD Vacutainer® Passive Shielding Blood Collection Needle", BD Diagnostics, 2006, 4 pages.
Injectable Drug Delivery 2010: Devices Focus, ONdrugDelivery Series, Aug. 2010, www.ondrugdelivery.com.
Introducing the 8 mm and 5 mm BD Autoshield™ Pen Needles, www.bd.com/autoshield, May 2009, 2 pages.
Smiths Medical, "Smiths Medical Wins $30 Million in Contracts for Safety Devices", Paul Harris—Director Communications, available online at: (http://www.smiths-medical.com/plugins/news/200B/may/30-million-contract html), May 29, 2008.
Stoker, Ron, "Stuck at Work Use Safety Blood Draw Products to Avoid Needlestick Injuries", Managing Infection Control, Jan. 2007, 6 pages.
International Search Report and Written Opinion from PCT/US2012/039893, mailed Sep. 7, 2012, 10 pages.

* cited by examiner

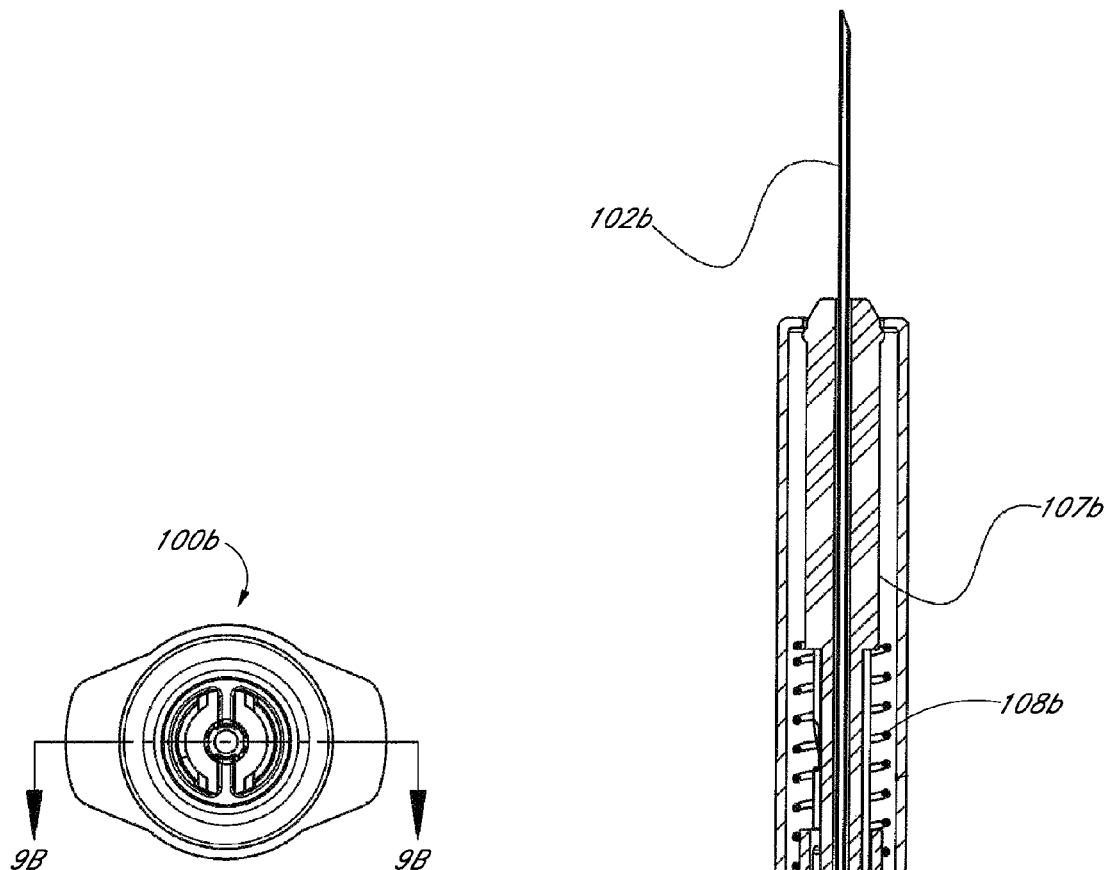
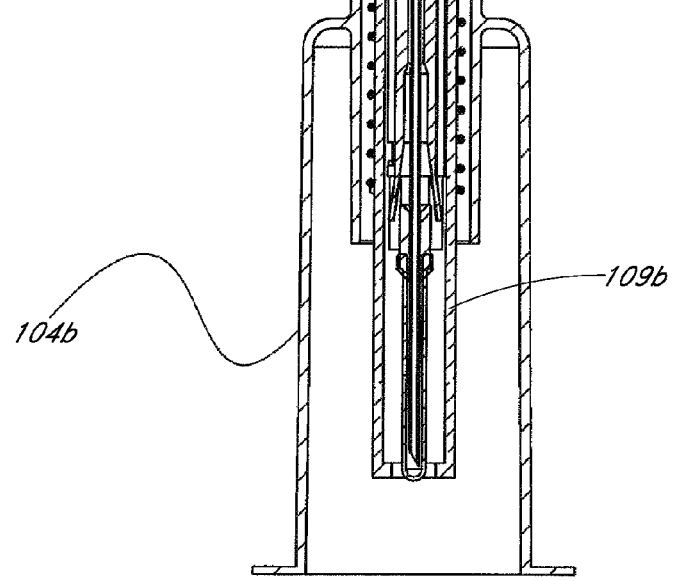
FIG. 9A
FIG. 9B

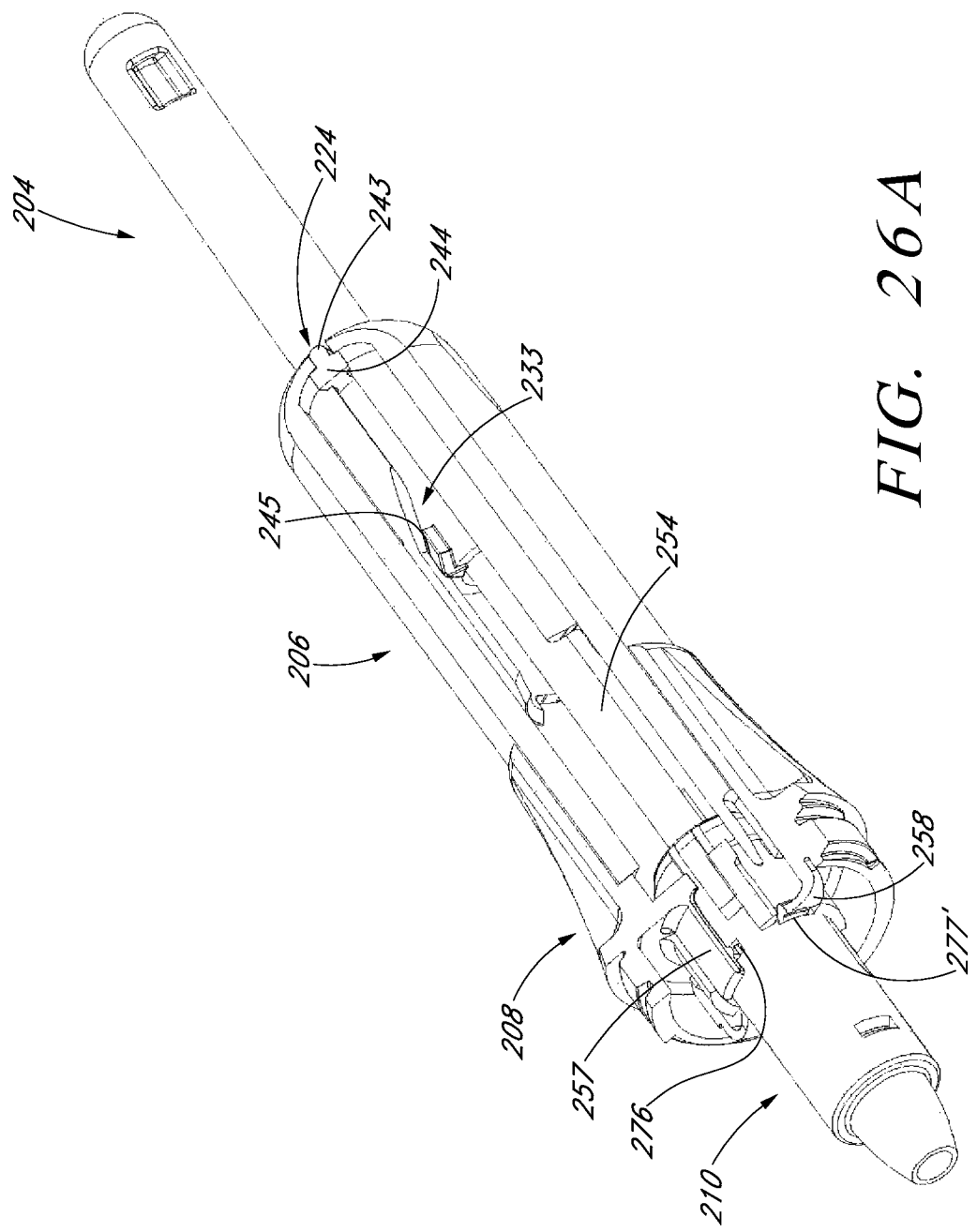

BLOOD COLLECTION SAFETY DEVICES AND METHODS OF USE AND MANUFACTURE

CROSS REFERENCE TO RELATED APPLICATIONS

This application claims the priority benefit under 35 U.S.C. §119(e) of U.S. Provisional Patent Application No. 61/491,830, filed May 31, 2011, U.S. Provisional Patent Application No. 61/596,684, filed Feb. 8, 2012, and U.S. Provisional Patent Application No. 61/615,783, filed Mar. 26, 2012, the entirety of each of which is incorporated herein by reference.

BACKGROUND

1. Field

Certain embodiments disclosed herein relate generally to blood collection devices and are particularly related to inhibiting accidental contact with needles in or on such devices.

2. Description of the Related Art

Blood analysis is an important diagnostic tool available to healthcare professionals. A significant aspect of modern medical care is the ability to collect samples of blood for analysis. In some cases, blood is collected by a syringe with a needle. The needle is inserted into a patient's vein and the plunger of the syringe is drawn back to aspirate a sample of blood into the syringe. However, operating the plunger while maintaining the needle in the vein can be difficult. Also, as the syringe can only hold a single sample, multiple needle insertions may be needed when more than one sample of blood is desired.

In other cases, blood is collected with a multi-sample sleeve, which usually includes two needle ends. The first needle end is inserted into the vein of a patient and the second needle end is configured to be inserted into a blood collection tube. Such blood collection tubes may have an evacuated chamber (e.g., containing a vacuum) and a self-sealing cap. When the blood collection tube is engaged with the second needle end, the needle pierces the self-sealing cap and the pressure difference between the evacuated tube and the vein causes blood to be aspirated into the tube. When the blood collection tube is removed from the second needle end, the self-sealing cap reseals the tube, thereby providing a sealed sample of blood. Furthermore, the first needle end can be maintained in the vein and additional blood collection tubes can be engaged with the second needle end to collect additional samples.

Due to the numerous potential hazards associated with the handling and manipulation of bodily fluids, and particularly blood, there are a number of safety features that can be incorporated into various types of blood collection devices. For example, some blood collection devices have needles that are provided with a removable cap that generally prevents needle sticks while the cover is in place. When the cap is removed, the needle is exposed. These caps are removed before a blood collection procedure and replaced after the procedure before discarding the needle. Among other concerns, this removal and replacement procedure creates a risk of accidental needle sticks.

Some blood collection devices have features that a user must activate in order to provide protection. For example, some blood collection devices include a hinged arm that the user can press to cause the arm to swing over the needle. Notably, such "active" safety mechanisms are not engaged unless and until the user takes an action to specifically engage the mechanism. In the stressful and fast-paced environment of many medical facilities, e.g., emergency rooms, users can neglect to trigger such active safety mechanisms, thereby rendering such mechanisms ineffective.

Blood collection devices are frequently configured to be disposable; that is, they are intended to be used only once and then thrown away. However, some blood collection devices fail to prevent reuse or other subsequent contact with the device, which can, for example, increase the likelihood of transferring blood or tissue-born diseases from one patient to another.

SUMMARY OF THE DISCLOSURE

In some embodiments, a first safety feature can provide selective covering and uncovering of a first needle. The first needle can be configured for insertion into a patient. The first safety feature can permit multiple needle exposures until such time as the first safety feature switches into a non-return closure mode. This mode can be actuated in multiple ways, such as when the needle has been fully exposed and then covered and/or when one or more other parts of the device have been actuated. In this non-return closure mode, the safety feature can lock permanently into place, preventing further needle exposure. A second safety feature can provide selective covering and uncovering of a second needle. The second needle can be configured for insertion into a blood-collection receptacle. The second safety feature can be configured to interact with and trigger an automatic deployment of a permanent closure mode for the first needle. In some embodiments, the actuation of either or both of the first and second safety features is automatic or passive in that the user of the device can be engaging in other aspects of using the device when the safety features are initiated by the device, thereby diminishing the risk of human error or neglect in deploying the safety features.

In some embodiments, a blood collection safety device has at least a first mode and a second mode. The device can include a housing comprising a chamber and a longitudinal axis. The device can also include a needle comprising a proximal tip and a distal tip, the proximal tip positioned in the chamber. The device can further include a plunger assembly configured to be received at least partly in the housing, the plunger assembly comprising a first needle cover and a second needle cover and a biasing member therebetween, the first needle cover and the second needle each configured to move along the longitudinal axis. In some cases, in the first mode the first needle cover and the second needle cover are at least partly nested along the longitudinal axis, and in the second mode the first needle cover and the second needle cover are spaced apart along the longitudinal axis. In some embodiments, the device is configured to engage a blood collection receptacle, e.g., a vial. In certain embodiments, in the second mode a portion of the first needle cover is positioned distal of the distal tip of the needle. In certain configurations, the first needle cover further includes an extension locking member.

In some embodiments, the first needle cover also has a rotational locking member and the housing also has a cam member. In some configurations, in the first mode the first needle cover longitudinally receives at least part of the second needle cover.

In certain configurations, the second needle cover has a plurality of tracks, and the first needle cover has a guide member configured to slide along the plurality of tracks. In certain cases, at least one of the tracks is an angled track. The track can be angled with respect to the longitudinal axis. In some cases, the sliding of the guide member in the angled track rotates the second needle cover.

In some embodiments, the housing has a needle support, such as a beam, connected with the needle and the second needle cover has a channel configured to slidingly receive the needle support.

In some embodiments, a blood collection safety device includes a housing comprising a chamber and a longitudinal axis. The device can also have a needle comprising a proximal tip and a distal tip, the proximal tip positioned in the chamber. Further, the device can have a proximal needle cover configured to move between an engaged position and a disengaged position. In some cases, the engaged position is at least partly distal of the disengaged position and the disengaged position is configured such that the proximal tip of the needle is positioned distal of a portion of the proximal needle cover. Additionally, the device can include a distal needle cover configured to move between a retracted position and an extended position. In some arrangements, the distal needle cover is positioned proximal of the distal tip of the needle in the retracted position and the distal needle cover is positioned distal of the distal tip of the needle in the extended position. Some configurations of the device have a locking member configured to retain the distal needle cover in the retracted position. In some cases, the locking member is released by the proximal needle cover moving to the engaged position.

In some embodiments, the locking member has an axially extending arm. In certain embodiments, the locking member is connected with a distal portion of the distal needle cover. In some configurations, the housing further includes a radially inwardly extending shoulder and a notch, and wherein the locking member engages the shoulder. In some embodiments, the locking member is released by rotation of the distal needle cover relative to the housing. Certain configurations also include a reuse prevention member configured to inhibit proximal movement of the distal needle cover after the distal needle cover has moved to the extended position.

In some embodiments, a method of manufacturing a blood collection safety device (such as a safety device having at least a first mode and a second mode) includes providing a housing having a longitudinal axis and a needle. In certain embodiments, the method also includes providing a first needle cover. Some configurations further include providing a second needle cover, the second needle cover configured to engage a blood collection vial, the second needle cover at least partly nested along the longitudinal axis with the first needle cover in the first mode. In some embodiments, the method also includes compressing a biasing member between the first needle cover and the second needle cover, the biasing member configured to encourage the first needle cover and the second needle cover to move to spaced apart positions along the longitudinal axis in the second mode.

In some embodiments, in the second mode a portion of the first needle cover is positioned distal of the distal tip of the needle. In certain embodiments, the first needle cover also includes an extension locking member. In some configurations, the first needle cover has a rotational locking member and the housing has a cam member. In some embodiments, in the first mode the first needle cover longitudinally receives at least part of the second needle cover.

In some embodiments, the housing further includes a needle support connected with the needle. Furthermore, in certain arrangements, the second needle cover also has a channel configured to slidingly receive the needle support.

In certain configurations, the second needle cover also includes a plurality of tracks, and the first needle cover also includes a guide member configured to slide along the plurality of tracks. In some cases, at least one of the tracks is angled with respect to the longitudinal axis. In some cases, the sliding of the guide member in the angled track rotates the second needle cover.

According to some embodiments, a method of using a blood collection safety device, which has a distal needle cover, a proximal needle cover, and a needle, includes positioning a distal end of the needle near or adjacent to a patient (e.g., against the patient's skin). The method can include applying an amount of distally-directed force on the blood collection safety device such that the distal end of the needle pierces the patient's skin. In certain implementations, the method includes engaging a blood collection vial with a proximal end of the needle, thereby placing the needle in fluid communication with the vial. Some embodiments include allowing blood to flow from the patient into the vial via the needle.

In certain variants, the method includes reducing the amount of distally-directed force such that the distal needle cover is moved distally of the blood collection safety device. For example, the distal needle cover can be moved by a biasing member. In some embodiments, the method includes removing the distal end of the needle from the patient (e.g., from the patient's skin). Certain implementations include disengaging the blood collection vial and the proximal end of the needle.

In certain embodiments, the method includes forming at least some of a protective enclosure around the needle. For example, in some embodiments, the protective enclosure is formed by positioning at least a portion of the distal needle cover distal of the distal end of the needle, thereby covering the distal end of the needle. In certain variants, the protective enclosure is formed by positioning at least a portion of the proximal needle cover proximal of the proximal end of the needle, thereby covering the proximal end of the needle. In some implementations, the protective enclosure is formed by passively securing the distal needle cover to prevent the distal end of the needle from moving distal of the portion of the distal needle cover. In some embodiments, the protective enclosure is formed by passively securing the proximal needle cover to prevent the proximal end of the needle from moving proximal of the portion of the proximal needle cover. Certain embodiments of the method include disposing of the blood collection safety device in a non-sharps waste receptacle.

In some embodiments, a method of using a blood collection safety device, which has a distal end, a proximal needle cover, and a needle, includes connecting the distal end of the blood collection device with a medical connector that is configured to be in fluid communication with a patient's blood. For example, the distal end of the blood collection device can include a medical connector interface. In some embodiments, the medical connector interface can comprise a male luer with a luer-lock shroud configured to be inserted into a corresponding female luer connector or another medical device, such as a catheter or shunt, connected to a patient. Many other structures and configurations can be used. For example, the medical connector interface can comprise a female luer connector configured to be attached to a male luer connector on another medical device. In some embodiments, the medical connector interface is threaded, configured to accept a Luer connector, or otherwise shaped to attach directly to a medical device or other instruments. In certain variants, the medical connector interface includes a passage or channel, such as a length of tubing. In some embodiments, the medical connector can be configured to engage with a needleless IV access device.

In certain implementations, the method includes placing the needle in fluid communication with the medical connector. Some variants of the method include engaging a blood collection vial with a proximal end of the needle, thereby placing the needle in fluid communication with the vial. In some embodiments, the method includes allowing blood to flow from the patient into the vial via the medical connector and the needle.

Certain implementations of the method include disengaging the blood collection vial and the proximal end of the needle. In some embodiments, the method includes forming at least some of a protective enclosure around the needle. For example, certain implementations of the method include positioning at least a portion of the proximal needle cover proximal of the proximal end of the needle, thereby covering the proximal end of the needle. Some implementations of the method include passively securing the proximal needle cover to prevent the proximal end of the needle from moving proximal of the portion of the proximal needle cover. According to some embodiments, the method includes disposing of the blood collection safety device in a non-sharps waste receptacle.

BRIEF DESCRIPTION OF THE DRAWINGS

Various embodiments are depicted in the accompanying drawings for illustrative purposes, and should in no way be interpreted as limiting the scope of the embodiments. In addition, various features of different disclosed embodiments can be combined to form additional embodiments, which are part of this disclosure.

FIG. 9A illustrates a bottom view of another embodiment of a blood collection safety device.

FIG. 9B illustrates a sectional view along the line 9B-9B of FIG. 9A.

FIG. 26A illustrates a rear perspective partial cross-sectional view of the device of FIG. 26, with the sleeve and biasing member not illustrated for clarity.

DETAILED DESCRIPTION OF CERTAIN EMBODIMENTS

A variety of examples of blood collection safety devices are described below to illustrate various examples that may be employed to achieve one or more desired improvements. These examples are only illustrative and not intended in any way to restrict the general inventions presented and the various aspects and features of these inventions. For example, although embodiments and examples are provided herein in the medical field, the inventions are not confined exclusively to the medical field and certain embodiments can be used in other fields. Furthermore, the phraseology and terminology used herein is for the purpose of description and should not be regarded as limiting. No feature, structure, or step disclosed herein is essential or indispensible.

Figure 1A:
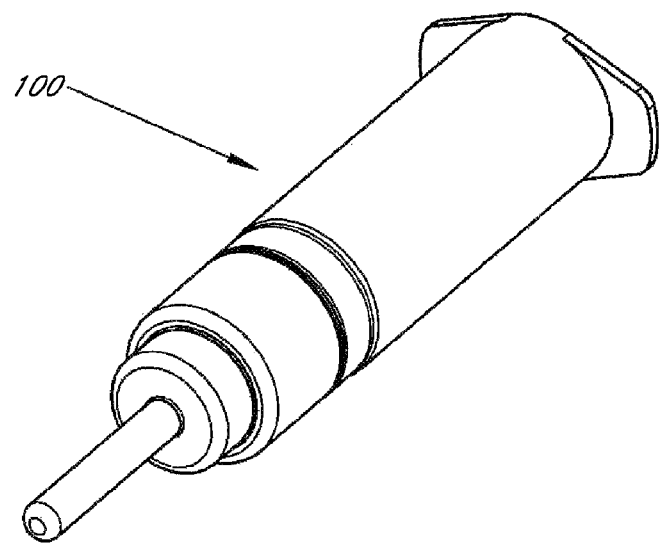
FIG. 1A illustrates a perspective view of an embodiment of a blood collection safety device.
Figure 1B:
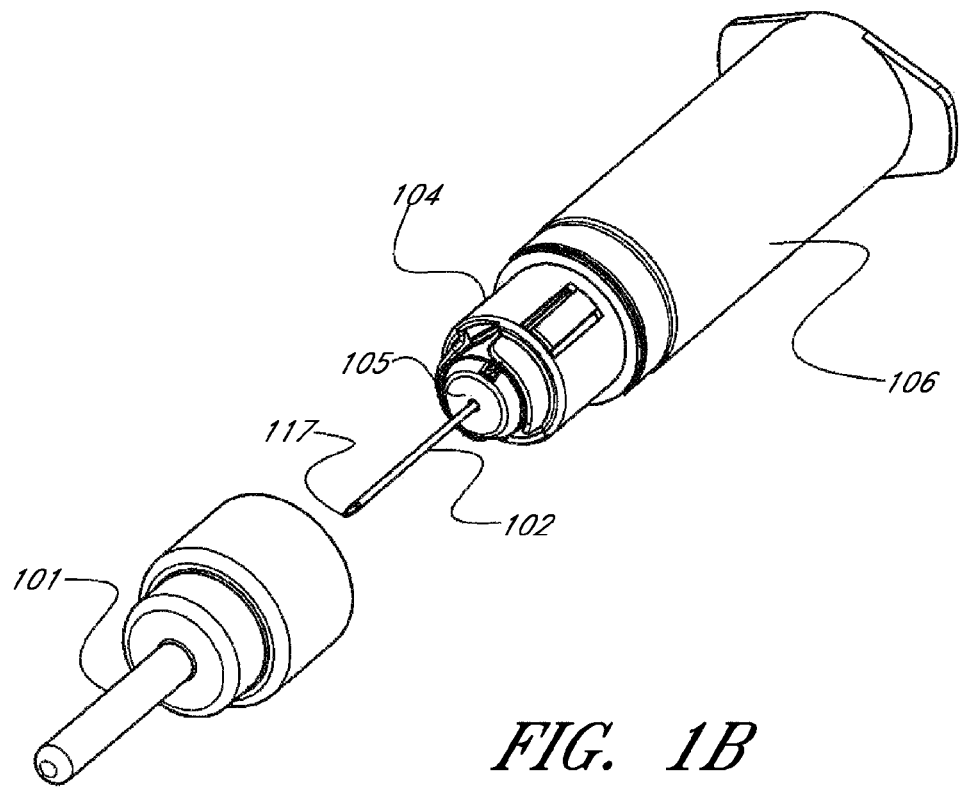
FIG. 1B illustrates a perspective view of the embodiment of FIG. 1A with a cap portion in a separated position.
Figures 2A, 2B:
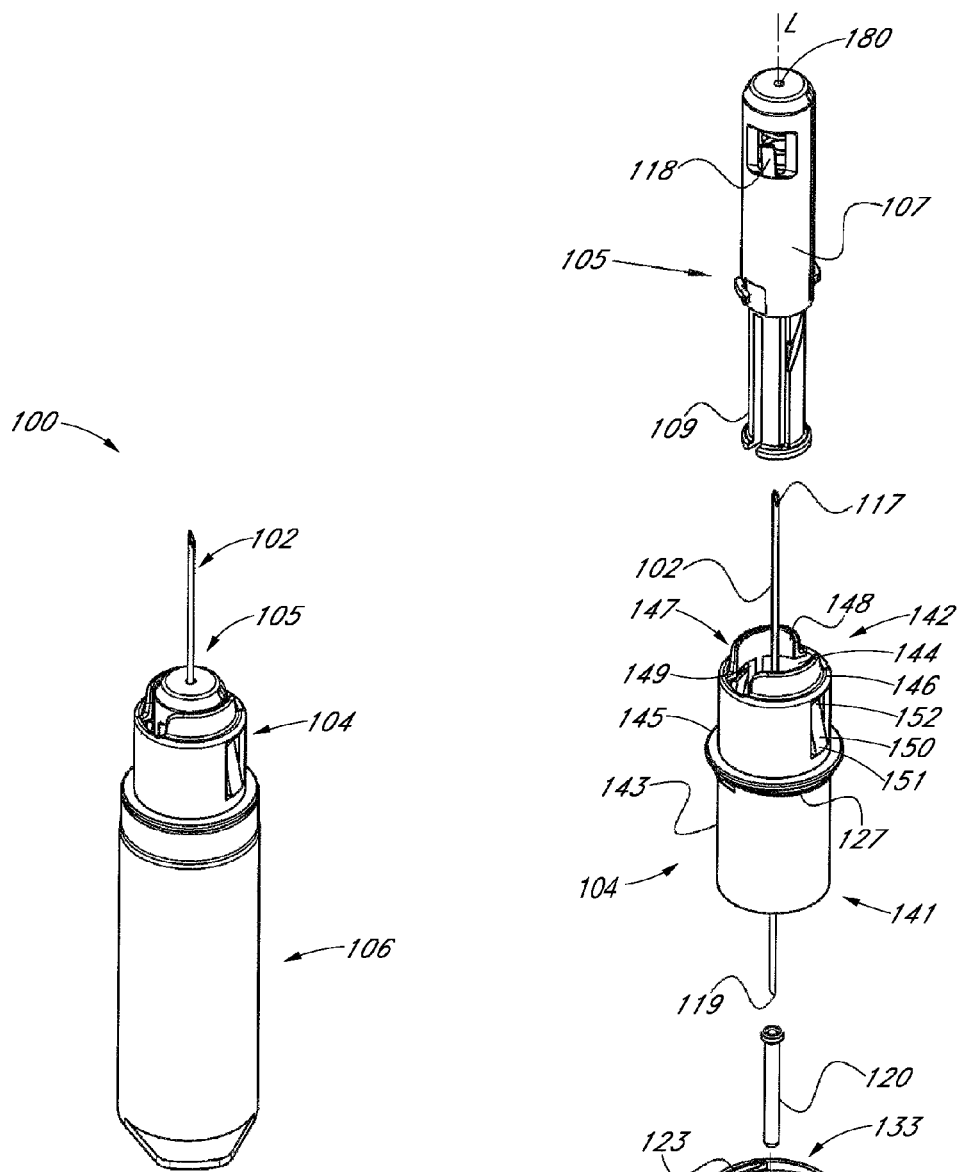
FIG. 2A illustrates a perspective view of the blood collection safety device of FIG. 1A in an upright position and without the cap portion.
FIG. 2B illustrates an exploded perspective view of the embodiment of FIG. 2A.

As illustrated in FIG. 1, in some embodiments, a blood collection safety device 100 includes a needle 102, housing 104, plunger assembly 105, a sleeve 106, and a longitudinal axis L. The needle 102 can include a distal end 117 and a proximal end 119 (FIG. 2B). As used herein, the term "distal," or any derivative thereof, refers to a direction toward the end of the blood collection safety device 100 that penetrates a patient's body; the term "proximal" refers to the opposite direction and is normally in the direction toward a user holding the blood collection safety device 100. Many kinds of medical needle (including needles for dentistry or veterinary procedures) can be used. Furthermore, although the needle 102 illustrated comprises a generally unitary tube, in other embodiments, the needle 102 comprises two distinct needle portions. In some embodiments, the two distinct needle portions extend in generally opposite directions. In some implementations, the two distinct needle portions are longitudinally spaced apart and are in fluid communication.

The blood collection safety device 100 can include features and components that automatically inhibit, prevent, or otherwise discourage using the device 100 multiple times or inadvertently inserting the needle into a second person, such as a health care professional or another patient. As used herein, the terms "automatically," "automatic," "passive," and "passively," and similar terms, are intended to have their ordinary meanings in the field. In some embodiments, as the context reflects, these terms refer to a mechanism or process that occurs in normal usage of a product and/or that occurs while the user is performing another process, without requiring an additional step or manipulation by the user (e.g., pressing a button, pushing a lever, triggering a switch, or otherwise) to achieve the desired result. For example, certain embodiments of the blood collection safety device 100 include a locking system that automatically or passively inhibits access to the distal end 117 of the needle 102 after a single use of the blood collection safety device 100. Such embodiments can, for example, reduce the likelihood of transferring blood or tissue-born diseases from one patient to another. The locking system and/or reuse-inhibition features of the blood collection safety device 100 could be used with many different types of medical and non-medical products.

Certain embodiments of the blood collection safety device 100 can include features and components that generally cover, obscure, extend beyond, protect, or hide at least the distal end 117 of the needle 102 after a single use of the blood collection safety device 100. In some embodiments, such configurations can, for example, reduce the likelihood of accidental contact with the distal end of the needle 117, e.g., unintentional needle sticks. Further, such configurations can reduce or alleviate at least some anxiety or fear that might otherwise be felt by certain patients or other individuals upon seeing the sharp distal end 117 being removed from their body. In some embodiments, both the distal end 117 and the proximal end 119 are covered, obscured, hidden, or protected by the blood collection safety device 100. Further details regarding some example embodiments of medical devices with automatically covering features that can be used with the devices disclosed herein are provided in U.S. Pat. No. 7,811,261, issued Oct. 12, 2010, and U.S. Patent Application Publication No. 2011/0319817, filed Jun. 23, 2010, each of which is incorporated herein by reference in its entirety.

In certain arrangements, a cap 101 is configured to mate with the housing 104 and/or cover the distal end 117 of the needle 102. In some instances, the cap 101 can include a distally extending casing that is closed at one end and configured to receive a portion of the needle 102 at the other end. The cap 101 can reduce or prevent contamination of the needle 102, for example during shipping and storage of the blood collection safety device 100. The cap 102 is generally removed just prior to a blood collection procedure, at which time the cap can be discarded. In certain embodiments, the cap is connected with the housing 104 by a hinge element, thereby allowing the cap 102 to be moved to expose the distal end 117 of the needle 102 yet remain connected with the housing 104. Such a configuration can, for example, provide for fewer discrete pieces for the user to monitor and keep track of.

As shown in FIG. 2B, the sleeve 106 can include a proximal end 131, a distal end 132, and an internal chamber 133. In certain configurations, the proximal end 131 includes projections 134, which can facilitate gripping or holding the blood collection safety device 100. As shown, the distal end 132 can include a distal opening 135, which can be configured to receive a portion of the housing 104. In some cases, the distal end 132 has threads 123. The chamber 133 is normally configured to receive a blood collection vial, such as a Vacutainer® blood collection vial or the like. The proximal end 131 of the sleeve 106 can include a proximal aperture 136 (FIG. 4A) to allow the blood collection vessel to be received into the chamber 133. In certain embodiments, the housing 104 and the sleeve 106 are monolithically formed.

The housing 104 can include a proximal body portion 141, a distal body portion 142, an outer surface 143, and an inner surface 144. In some cases, the needle 102 mounts with the housing 104, such as with an adhesive, sonic welding, or otherwise. In some embodiments, the housing 104 includes a needle support 181 (FIG. 4A), such as a beam, configured to maintain the needle 102 in a position generally along the longitudinal axis L. In some cases, the proximal end 119 of the needle 102 is positioned inside and covered with a resilient boot 120.

The proximal body portion 141 can be configured to couple with the housing 104. For example, in the embodiment shown in FIG. 2A, the proximal body portion 141 of the housing 104 is received by the distal end 132 of the sleeve 106. In certain cases, the outer surface 143 of the housing 104 includes threads 127 which can be configured to mate with the threads 123 of the sleeve 106. Also, in certain cases, the outer surface 143 of the housing 104 has a radially outwardly extending flange 145 which can, for example, limit the amount of insertion of the housing 104 into the sleeve 106.

As illustrated, the distal body portion 142 can have a radially inwardly extending shoulder 146 and a distal aperture 147. In some cases, the distal body portion 142 also includes one or more distally extending guides 148. Such guides can include a bearing surface 126 (FIG. 4B) and can, for example, provide radial support during movement of the plunger assembly 105, as will be discussed below. In certain configurations, the shoulder 146 includes one or more radial notches 149. As shown, the notches 149 can be positioned between the guides 148.

In certain embodiments, the distal body portion 142 includes one or more retraction locking members 150. In some cases, the retraction locking member 150 is positioned at least partially within a window 153 included in the distal body portion 142. As shown, a first end 151 of the retraction locking member 150 can be coupled with the distal body portion 142, while a second end 152 of the retraction locking member 150 can be disposed radially inwardly. In some embodiments, the retraction locking member 150 is generally resilient, so that the radially inwardly disposed second end 152 can flex and then return to its original position after the second end 152 has been radially outwardly deflected. In some embodiments, the first end 151 is larger than the second end 152, e.g. the retraction locking member 150 can taper from the first end 151 to the second end 152. In some embodiments, the retraction locking member 150 includes a latching member, such as a hook, clasp, detent, ratchet, or otherwise.

Figure 3A:
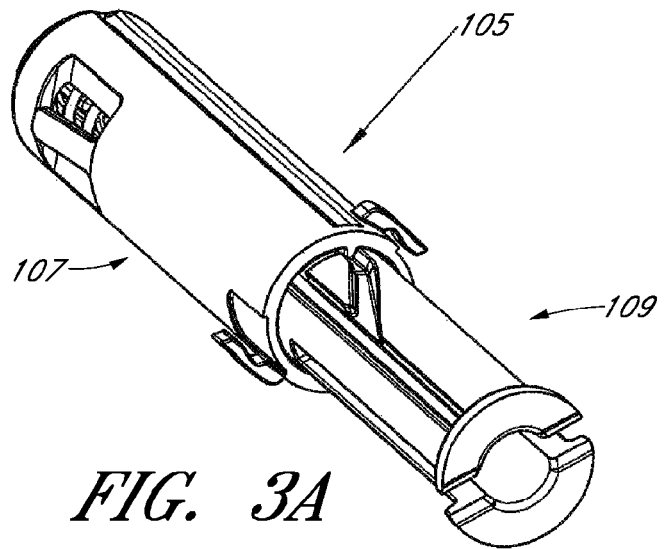
FIG. 3A illustrates a perspective view of an embodiment of a plunger assembly of the device of FIG. 1A.
Figure 3B:
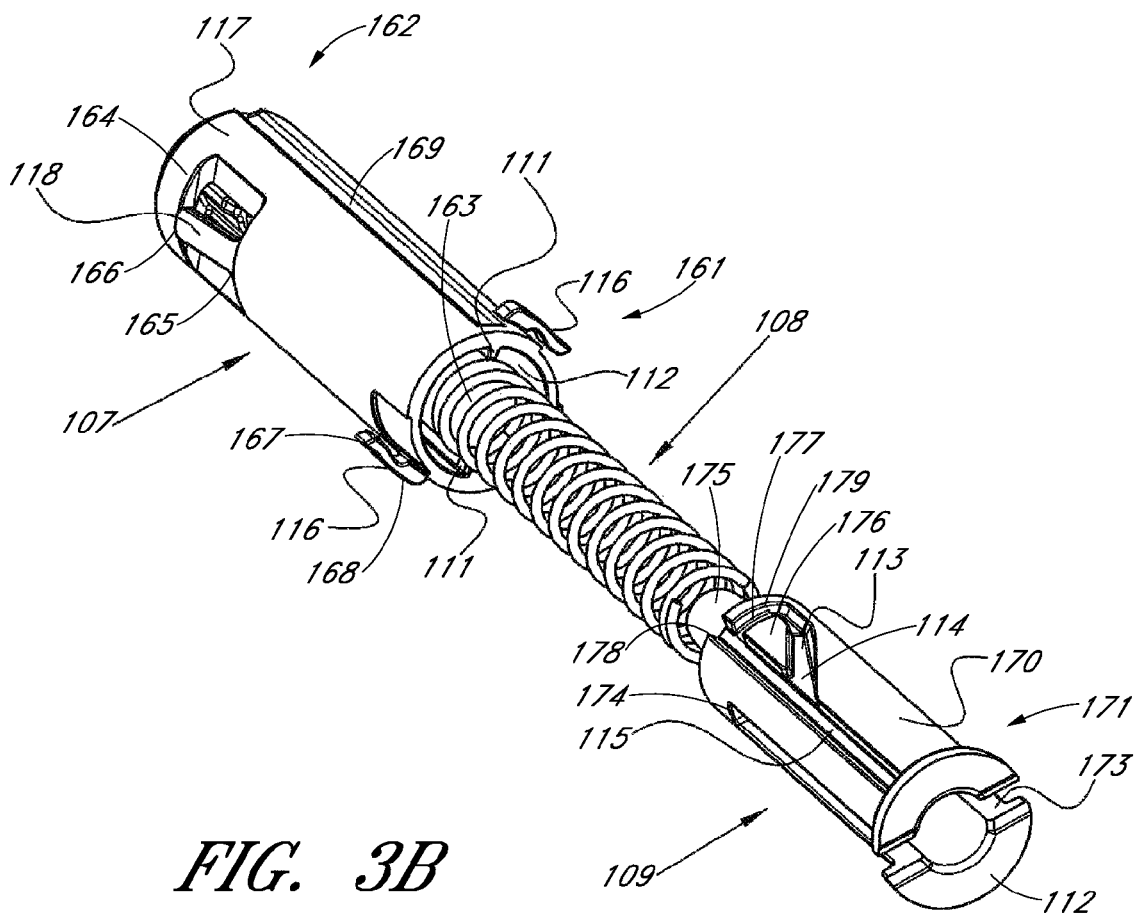
FIG. 3B illustrates a perspective exploded view of the plunger assembly of FIG. 3A.

With continued reference to FIG. 2B, as well as to FIGS. 3A and 3B, the plunger assembly 105 can include a sheath 107, a biasing member 108, and a piston 109. In various embodiments, at least part of the plunger assembly 105 is configured to be received in the housing 104 and in the sleeve 106.

The sheath 107 can have an elongate shape having a central lumen therethrough, a proximal end 161, and a distal end 162 with a distal aperture 180. In some cases, the sheath 107 includes a distally extending portion 163 configured to receive the biasing member 108. The distally extending portion 163 can have most any shape, such as annular, cylindrical, frustoconical, or otherwise. In certain cases, the sheath 107 has at least one radially inwardly extending guide member 111, which can be configured to mate with one or more portions of the piston 109, as discussed below. The central lumen and the distal aperture 180 can be configured to receive the distal end 117 of the needle 102 therethrough.

In some configurations, the sheath 107 has one or more extension locking members 118. For example, as shown, the sheath 107 includes a radially outwardly extending extension locking member 118. In certain configurations, the extension locking member 118 is sized to be received through the notch 149 along the longitudinal axis, as discussed below. In some embodiments, the extension locking member 118 is disposed in a window 164 of the sheath 107. In some cases, the window 164 opens into the central lumen of the sheath 107. In some configurations, the extension locking member 118 is substantially anchored to the sheath 107. For instance, in some cases the locking member 118 includes a radially projecting fin. In other configurations, only a portion of the extension locking member 118 is anchored to the sheath 107. For example, a first end 165 of the extension locking members 118 can be connected with the sheath 107 and a second end 166 of the extension locking members 118a can be angled radially outwardly.

In some embodiments, the extension locking member 118 is generally resilient. A resilient extension locking member 118 can allow the radially outwardly disposed second end 166 to flex and then return to its original position after the second end 166 has been radially inwardly deflected. In some embodiments, the first end 165 is larger than the second end 166, e.g., the extension locking member 118 can taper from the first end 165 to the second end 166. In some embodiments, the extension locking member 118 includes a latching member, such as a hook, clasp, detent, ratchet, or otherwise.

In certain configurations, the sheath 107 has one or more rotational locking members 116. For example, in certain embodiments the sheath 107 includes two rotational locking members 116, equally spaced about the periphery of the sheath 107. As shown in FIG. 3B, the rotational locking members 116 can be located near the proximal end 161 of the sheath 107. However, in other configurations, the rotational locking members 116 are positioned in other locations, such as near the distal end 162 of the sheath 107.

The rotational locking member 116 can include a projection that extends circumferentially, radially, axially, or a combination thereof. For example, in the embodiment of FIG. 3B, the rotational locking member 116 projects radially outward from, and along a portion of the circumference of, the sheath 107. The rotational locking member 116 can be generally resilient, to allow the rotational locking member 116 to return to its original position after having been deflected radially inwardly. In some aspects, the rotational locking member 116 also includes an intermediate narrowed portion 168, which can facilitate such flexing of the rotational locking member 116.

In certain configurations, the rotational locking member 116a has a cantilevered end 167. In some cases, the cantilevered end 167 is tapered, such that the radial width of the cantilevered end 167 decreases. In some cases, the cantilevered end 167 includes a radially outwardly extending wedge, such that the radial width of the cantilevered end 167 increases. In certain aspects, the cantilevered end 167 is flat.

Some embodiments of the sheath 107 include one or more grooves 169. For example, as shown in FIG. 3B, the sheath 107 includes a groove 169 that extends substantially longitudinally. In some embodiments, such a groove 169 is configured to mate with a corresponding projection in the housing 104 or piston 109 to guide the longitudinal movement of the sheath 107. In some configurations, the groove 169 extends substantially the entire length of the sheath 107. In other configurations, the groove 169 extends along only a portion of the length of the sheath 107. In some cases, the groove 169 extends circumferentially or helically along a portion of the sheath 107.

In some embodiments, such as in the illustrated embodiment, the biasing member 108 engages and extends between the sheath 107 and the piston 109. The biasing member 108 illustrated is a conical spring, but many types of biasing member 108 can be employed, such as a helical spring, wavespring, belleville washers, or otherwise. In some embodiments, the biasing member 108 is a conical coil spring having a free length of about 100 mm and a spring rate of at least about 0.12 N/mm through the linear portion of the spring's deflection. Other constructions can include softer or stiffer springs depending on the application, and can be constructed of substantially any suitable material. Progressive springs and/or multiple springs of varying lengths can also be used, for example, to provide a variable effective spring rate.

In some configurations, the biasing member 108 is configured to facilitate extension of the sheath 107 after a blood collection vial has been engaged with the blood collection safety device 100. Further, the biasing member 108 can be configured to facilitate movement of the sheath 107 distally without distal force by the user. For example, when the user is moving the blood collection safety device 100 proximally (such as during extraction of the distal end 117 of the needle 102 from a patient's body), the biasing member 108 can be configured to encourage the sheath 107 distally relative to the housing 104.

In certain embodiments, the piston 109 has a generally elongate body 170 and a proximal flange 171. The elongate body 170 can include a central lumen extending the length of the piston 109 and configured to allow passage of the proximal end 119 of the needle 102 therethrough. The proximal flange 171 can include a radially outwardly extending proximal surface 172, which can be configured to mate with the distal end of a blood collection vial. As shown in FIG. 3B, the piston 109 can include a longitudinally extending channel 173. In some cases, the channel 173 does not extend the entire longitudinal length of the piston 109. Accordingly, in certain configurations, the channel 173 terminates in a stop 174. In some cases, the piston 109 includes a distally extending portion 175 which can receive the biasing member 108.

With continued reference to FIGS. 3A and 3B, the piston 109 can include an initial track 113, a transfer track 114, and an engagement track 115 to aid in, for example, directing movement of the sheath 107. As shown, the tracks 113-115 can be located on an external surface of the piston 109. However, other track locations are contemplated, such as on the inside of the sheath 107 or on the inside of the housing 104. In many arrangements, the tracks are configured to slidingly receive the guide member 111 of the sheath 107. Accordingly, the tracks 113-115 can be configured to have a similar cross-sectional shape as the guide member 111, e.g., generally rectangular, generally T-shaped, generally circular sector, or otherwise. For instance, the illustrated guide member 111 and the tracks 113-115 are generally trapezoidal in cross sectional shape.

In some embodiments, the initial track 113 and the engagement track 115 are generally parallel to the longitudinal axis. In some cases, the initial track 113 extends along only a portion of the longitudinal length of the piston 109 and the engagement track 115 extends along substantially all of the longitudinal length of the piston 109. For example, in some cases, the initial track 113 extends along at least about 20% of the longitudinal length of the piston 109 and the engagement track 115 extends along at least about 90% of the length of the piston 109. In some configurations, a separation member 176 separates the initial and engagement tracks 113, 115 throughout at least a portion of their length.

The transfer track 114 can be positioned in a middle or intermediate region along the length of the piston 109 and at an angle relative to the longitudinal axis (e.g., non-parallel to the axis), and can intersect the initial and engagement tracks 113, 115. The transfer track 114 can thus connect the initial and engagement tracks 113, 115 to permit the guide member 111 to shift between the initial track 113 and the engagement track 115 as will be discussed in further detail below. In some embodiments, the transfer track 114 is generally straight and non-curvilinear to facilitate smooth travel along the transfer track 114. In the example illustrated, the intersection of the transfer track 114 and the engagement track is positioned in about the longitudinal middle of the piston 109. In some embodiments, the intersection of the transfer track 114 and the initial track 113 is distal to the intersection of the transfer track 114 and the engagement track 115. In some embodiments, the length of the transfer track 114 is generally substantially less than the longitudinal length of the piston 109. In the illustrated embodiment, the transfer track 114 does not constitute a portion of, or a continuation of, either of the initial or engagement tracks 113, 115; rather, the transfer track 114 extends away from the tracks 113, 115 at a point on each track 113, 115 that is spaced between the beginning and end of the tracks 113, 115 (e.g., at an intermediate or middle region of the tracks 113, 115). In certain embodiments, the engagement track 115 terminates in a distal open notch 178.

In some embodiments, the piston 109 includes an assembly track 177. The assembly track 177 can be configured to be inclined in the direction from the engagement track 115 toward the initial track 113 and terminate in a generally flat face 179 at the intersection between the initial track 113 and the assembly track 177. Such a track 177 can facilitate, for example, assembly of the guide member 111 into the initial track 113. For example, during assembly of come embodiments of the blood collection safety device 100, the guide member 111 of the sheath 107 is inserted through the distal open notch 178 of the engagement track 115 and then into the assembly track 177. As the guide member 111 is moved along the assembly track 177 the guide member 111 rides up the incline of the assembly track 177 until reaching the generally flat face 179, at which point the guide member 111 can snap to the bottom of the initial track 113. Thereafter, the flat face 179 can inhibit or prevent disassembly of the sheath 107 from the piston 109 by presenting a barrier or impediment to the guide member 111 returning along the assembly track 177.

The blood collection safety device 100 can have many different sizes, to accommodate the various sizes of blood collection vials and types of blood collection procedures. In some embodiments, the blood collection safety device 100 can have an overall length of at least about 25 mm and/or less than or equal to about 200 mm, a sleeve 106 with an outside diameter of at least about 6 mm and/or less than or equal to about 50 mm, a housing 104 with an outside diameter of at least about 5 mm and/or less than or equal to about 45 mm and a sheath 107 with an outside diameter of at least about 3 mm and/or less than or equal to about 20 mm. In some embodiments, the sheath 107 is longitudinally longer than the piston 109. In some embodiments, the sheath 107 is longer than the housing 104 (not including the needle 102). In some embodiments, the needle 102 has a gauge of at least 15 (nominal outside diameter of about 1.83 mm) and/or less than or equal to 34 (nominal outside diameter of about 0.18 mm).

The blood collection safety device 100, and components thereof, can be formed using many manufacturing processes sufficient to provide the desired shape of the components. In some embodiments, one or more components are made by a molding process, such as, injection molding, compression molding, blow molding, transfer molding, or similar. In some embodiments, one or more components are formed by forging, machining, casting, stamping, extrusion, a combination thereof, or otherwise.

In many embodiments, the blood collection safety device 100 is constructed from a generally non-corroding, bio-stable material. For example, in some arrangements, one or more of the components of the blood collection safety device 100 are plastic (e.g., polyetheretherketone) or metal (e.g., aluminum, titanium, stainless steel, or otherwise). In some embodiments, the sleeve 106, housing 104, and/or the sheath 107 are constructed of materials that are translucent, opaque, or otherwise optically distortive, such that some portion (e.g., the distal tip 117) or all of the needle 102 is generally covered after the blood collection procedure has been completed and the needle 102 has been removed from the patient.

Figure 4A:
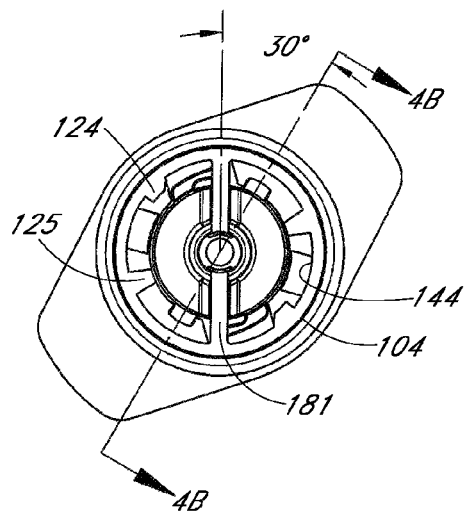
FIG. 4A illustrates a bottom view of the device of FIG. 3A in an initial position.

With reference to FIG. 4A, which illustrates a bottom view of the blood collection safety device 100, the housing 104 can further include the needle support 181 and an inner chamber 184. In certain cases, the needle support 181 extends from one side of the housing 104 to the other side thereof. For example, as shown, the needle support 181 can extend diametrically across the diameter of the housing 104. The needle support 181 can connect with the needle 102, such as by an adhesive. In certain embodiments in which the needle 102 comprises two distinct needle portions, the two distinct needle portions are mounted to the needle support 181.

In some cases, the inner surface 144 of the housing 104 includes a radially inwardly extending rib 125. Such a rib 125 can, for example, provide support for, and inhibit kinking of, the plunger assembly 105 during movement of the sheath 107. In some cases, the rib 125 extends radially inward but does not inhibit longitudinal movement of the sheath 107. The rib 125 can extend along a portion or substantially all of the longitudinal length of the housing 104.

In certain configurations, the housing 104 includes a generally wedge-shaped cam member 124 that extends radially inwardly from the inner surface 144 of the housing 104. The cam member 124 can include a generally flat face 182 and an inclined face 183. In the variant shown, the inclined face 183 is configured to be in the circumferentially opposite direction as the flat face 184. The cam member 124 can extend along a portion or substantially all of the longitudinal length of the housing 104.

Figure 4C:
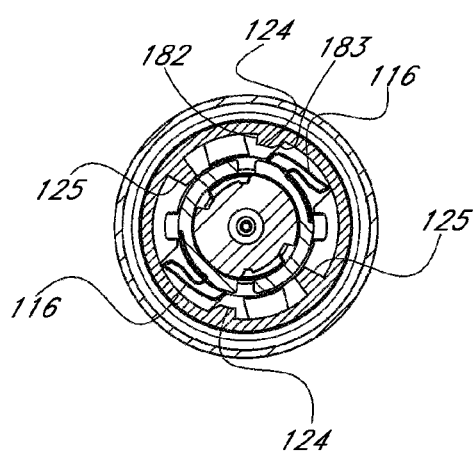
FIG. 4C illustrates a sectional view along the line 4C-4C of FIG. 4B.

As shown in FIG. 4C, in the rotational locking members 111 of the sheath 107 can be circumferentially disposed between the rib 125 and the inclined face 183 of the cam member 124. In certain configurations, the cantilevered end 167 of the rotational locking member 111 points away from the inclined face 183 of the cam member 124.

Figure 4B:
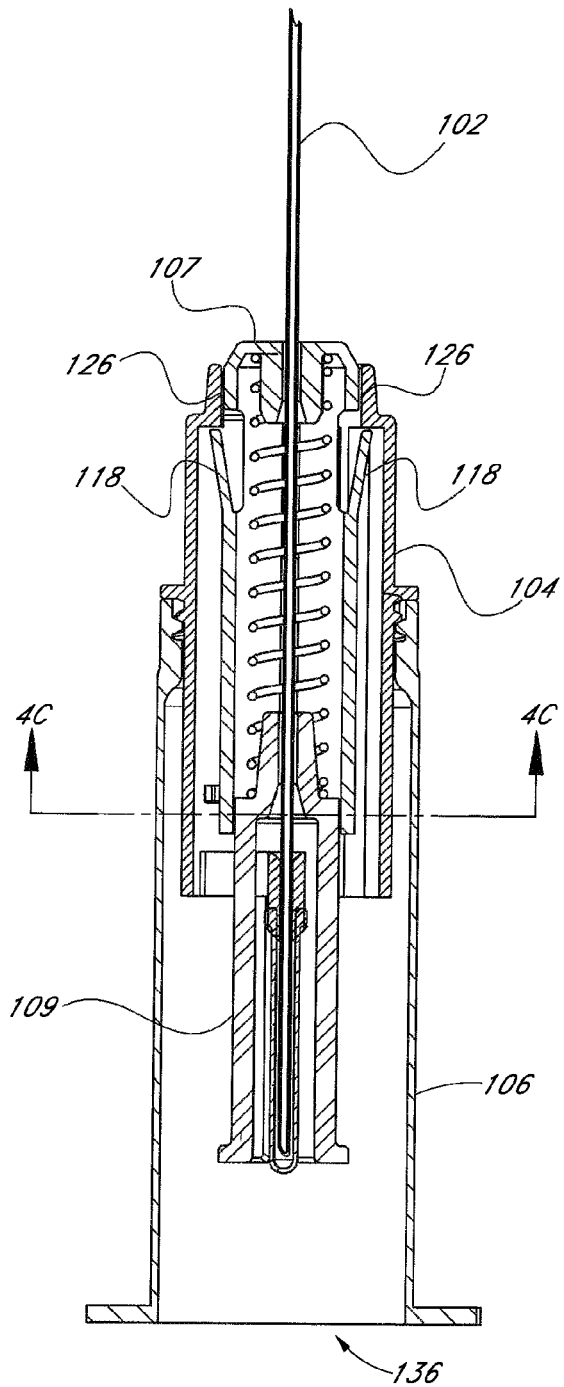
FIG. 4B illustrates a sectional view along the line 4B-4B of FIG. 4A.

In FIGS. 4A-4C, the blood collection safety device 100 is illustrated in an initial and ready-to-operate mode. The plunger assembly 105 is received in the housing 104, which in turn is mated with the sleeve 106. The sheath 107 is in a first position, which exposes the distal end 117*a* of the needle 102*a*, and the piston 109 is covering the proximal end 119 of the needle 102. The needle support 181 of the housing 104 is received in the channel 173 of the piston 109 and is abutted with the stop 174. The extension locking member 118 of the sheath 107 is received in the inner chamber 184 of the housing 104 and, as shown in this initial position, abuts against the radially inwardly extending shoulder 146 of the housing 104. Accordingly, although the bias of the biasing member 108 tends to drive the plunger 109 and the sheath 107 apart, the needle support 181 abutting the stop 174 inhibits proximal movement of the piston 109 and the shoulder 146 abutting the extension locking member 118 inhibits distal movement of the sheath 107. Thus, in this initial and ready-to-operate configuration, the sheath 107 and the piston 109 are held in a stable first position relative to each other. In certain embodiments, in the first position of the sheath 107 and the piston 109, the sheath 107 receives at least some of the longitudinal length of the piston 109. For example, as shown a portion of the piston 109 can be received into the central lumen of the sheath 107. Furthermore, as shown in FIG. 3A, in the initial and ready-to-operate mode the guide member 111 of the sheath 107 is disposed in the initial track 113 of the piston 109.

During a blood collection procedure, after removing the cap 101 (if used) and taking surface prepatory steps (if appropriate, e.g. applying a disinfectant to the surface), the distal end 117 of the needle 102 can be placed against the patient's skin at the desired penetration site.

After the distal end 117 of the 102 is inserted into the patient, e.g., in a vein, the blood collection portion of the procedure generally begins. A distal end a blood collection vial (not shown) can be abutted with the proximal surface 172 of the piston 109. The user generally applies distal force to the blood collection vial, which in turn applies distal force to the piston 109 against the bias of the biasing member 108 (which, in certain embodiments, has been biasing the piston 109 proximally into abutment with the stop 174). The distal force on the piston 109, if sufficiently large, can overcome the bias of the biasing member 108 and move the piston 109 distally, which can expose the proximal end 119 of the needle 102 and allow engagement of the blood collection vial with the proximal end 119 of the needle 102.

In certain configurations, as the piston 109 moves distally, the guide member 111 of the sheath 107 slides along the initial track 113 until the guide member 111 reaches the intersection of the initial track 113 and the transfer track 114. Upon reaching the intersection of the initial and transfer tracks 113, 114, further distal movement of the piston 109 encourages the guide member 111 into the angled transfer track 114.

As the blood collection vial is continued to be moved distally, thereby moving the piston 109 further distally, the guide member 111 traverses the transfer track 114 thereby encouraging the sheath 107 to rotate about the longitudinal axis by approximately the number of degrees (e.g., at least about 10° and/or less than or equal to about 120°) that separate the initial and engagement tracks 113, 115. In contrast, rotation of the piston 109 (relative to the housing 104) can be inhibited by the needle support 181 passing through the channel 173 of the piston 109.

Rotation of the sheath 107 in turn rotates the rotational locking member 116. In certain embodiments, the rotational locking member 116 rotates toward the inclined face 183 of the cam member 124. Continued rotation of the rotational locking member 116 of the sheath 107 slidably engages the rotational locking member 116 (e.g., the cantilevered end 167) with the inclined face 183, thereby deflecting the rotational locking member 116 radially inward and producing a slight but noticeable resistance. In some embodiments, as illustrated, the circumferential length of the rotational locking member 116 can be generally about the same as or shorter than the length of the transfer track 114.

With further distal movement of the blood collection vial, and in turn the piston 109, the guide member 111 exits from the transfer track 114 into the engagement track 115, thus continuing to rotate the sheath 107 with respect to the piston 109. Such continued rotation can rotate the rotational locking member 116 beyond the circumferential width of the cam member 124, thereby allowing the rotational locking member 116 to deflect radially outward to about its original radial position shown in FIG. 4C. In this configuration, the generally flat face 182 presents a physical stop thereby inhibiting counter-rotation of the rotational locking member 116, and in turn the sheath 107. As the sheath 107 is inhibited from counter-rotating, the guide member 111 is inhibited from returning into the transfer track 114. In some embodiments, the outward deflection of the rotational locking member 116 produces a tactile vibration and/or an audible sound, e.g. "snap," which can provide verification that the rotational locking member 116 has been locked and counter-rotation is prevented.

In certain configurations, rotation of the sheath 107 can rotate the extension locking member 118 into longitudinal alignment with the notch 149 in the shoulder 146 of the housing 104. For example, about when the guide member 111 of the sheath 107 enters the engagement track 115, the extension locking member 118 rotates into longitudinal alignment with the notch 149. In some cases, about when the rotational locking member 116 of the sheath 107 rotates past the cam member 124, the extension locking member 118 rotates into longitudinal alignment with the notch 149.

In some embodiments, when the extension locking member 118 is aligned with the notch 149, the extension locking member 118 no longer abuts the shoulder 146. Rather, in such embodiments, the extension locking member 118 is allowed to pass distally through the notch 149. Accordingly, when the extension locking member 118 aligned with the notch 149, the sheath 107 can be moved distally by the bias of the biasing member 108. In some such cases, the sheath 107 moves distally into abutment with the surface being penetrated by the needle 102 (e.g., the skin of the patient).

In various embodiments, if additional samples of blood are desired, additional blood collection vials can be engaged with the proximal end 119 of the needle 102. Once the desired number of samples has been collected, the user generally moves the blood collection safety device 100 proximally, thereby extracting the distal end 117 of the needle 102 from the patient. In some embodiments, as the distal end 117 of the needle 102 is extracted proximally, the sheath 107 is automatically moved distally (relative to the distal end 117) by the bias of the biasing member 108. As the biasing member 108 can automatically move the sheath 107, the user does not need to remember to trigger or otherwise activate such a feature.

In certain configurations, after the distal end 117 of the needle 102 is removed from the patient, the sheath 107 covers the distal end 117. Such configurations can reduce the likelihood of accidental contact with the distal end of the needle 117, e.g., unintentional needle sticks. For example, a portion of the sheath 107 can be moved to a position distal of the distal end 117 of the needle 102. In some cases, the sheath 107 is moved such that the distal aperture 180 is distal of the distal end 117.

In some embodiments, rotation of the sheath 107 can rotate the rotational locking member 116 into longitudinal alignment with the retraction locking member 150 in the housing 104. For example, in certain cases, about when the guide member 111 of the sheath 107 enters the engagement track 115, the rotational locking member 116 rotates into longitudinal alignment with the retraction locking member 150. In some cases, when the rotational locking member 116 rotates past the cam member 124, it also rotates into longitudinal alignment with the retraction locking member 150.

In some configurations, as the sheath 107 is moved distally by the biasing member, the rotational locking member 116 of the sheath 107 engages the retraction locking member 150. For example, in some cases, the rotational locking member 116 directly contacts the retraction locking member 150. In some cases, the rotational locking member 116 can deflect the retraction locking member 150 radially outwardly. As the sheath 107 continues to move distally, the rotational locking member 116 can continue to increase the outward deflection of the retraction locking member 150.

Figure 5A:
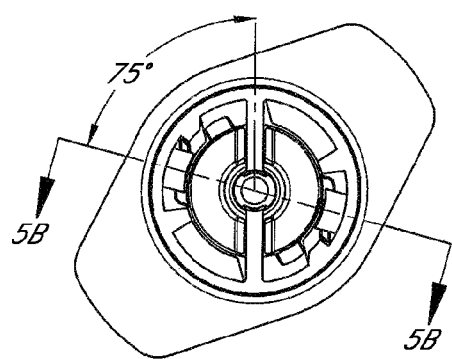
FIG. 5A illustrates a bottom view of the device of FIG. 3A in an extended and locked position.
Figure 5C:
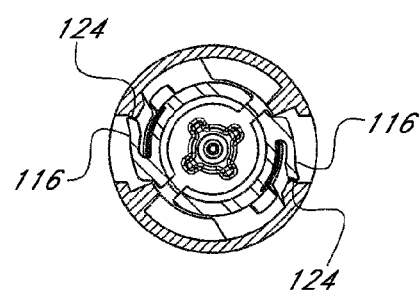
FIG. 5C illustrates a sectional view along the line 5C-5C of FIG. 5B.
Figure 5B:
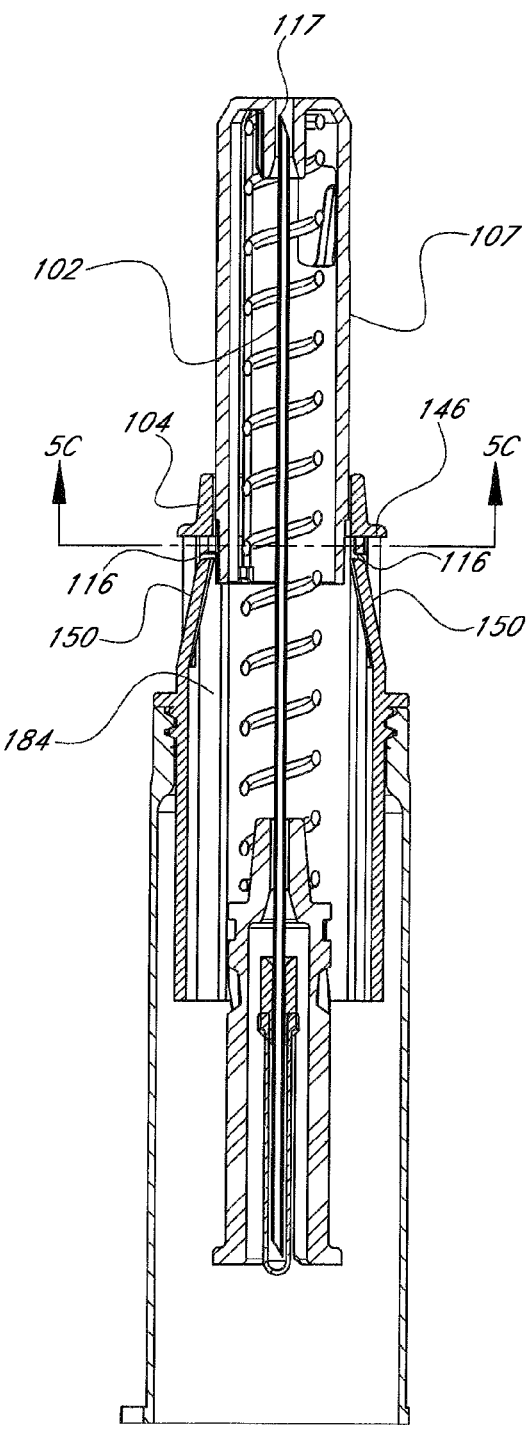
FIG. 5B illustrates a sectional view along the line 5B-5B of FIG. 5A.

With regard to FIGS. 5A-C, the blood collection safety device 100 is illustrated in an extended and locked position. In the embodiment shown, the rotational locking member 116 has moved distal of the retraction locking member 150 and into abutment with the shoulder 146. As the rotational locking member 116 is no longer deflecting the retraction locking members 150, the retraction locking members 150 have deflected radially inward again (e.g., to about their original position). In such a configuration, the retraction locking member 150 presents an interference that inhibits proximal movement of the rotational locking member 116. Thus, proximal movement of the sheath 107 is inhibited by the retraction locking member 150 and distal movement of the sheath 107 is inhibited by the shoulder 146, thereby rendering the sheath substantially locked and/or immobile. Further, as the sheath 107 can be configured to extend distal of the distal end of the needle 102, the locked sheath 107 renders the needle 102 generally inaccessible. Such a configuration can discourage or prevent re-use of the needle 102 and can reduce the chance of or substantially prevent unintentional contact with the needle 102.

FIGS. 6A-8D illustrate another embodiment of a blood collection safety device 100a. Several features and components of the blood collection safety device 100a are identical or similar in form and function to those described above with respect to the blood collection safety device 100, and have been provided with like numerals, with the addition of "a" (e.g., 100a rather than 100). To the extent that parts of the blood collection safety device 100a differ from those of the blood collection safety device described above, some of those differences are described and explained herein. Any features and/or components of the disclosed embodiments can be combined or used interchangeably.

Figure 6A:
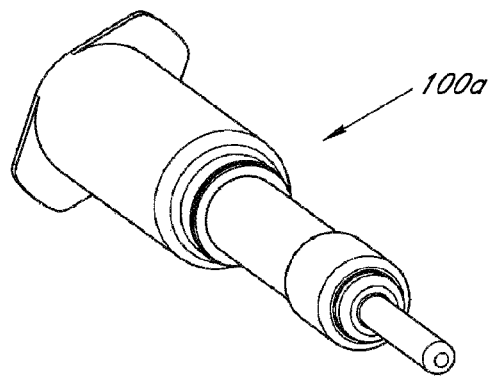
FIG. 6A illustrates a perspective view of another embodiment of a blood collection safety device.
Figure 6B:
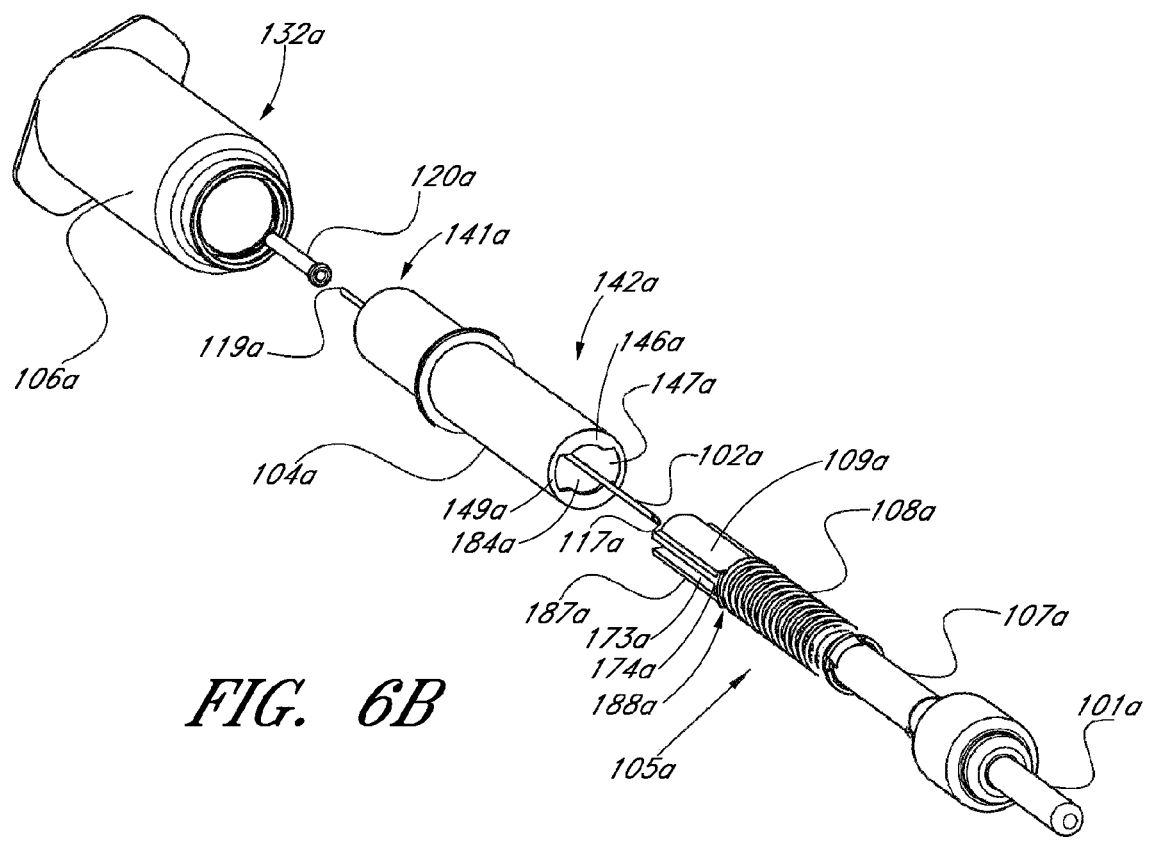
FIG. 6B illustrates a perspective exploded view of the device of FIG. 6A.

In the embodiment illustrated in FIGS. 6A and 6B, the blood collection safety device 100a includes a needle 102a, sleeve 106a, plunger assembly 105a, and housing 104a, and a longitudinal axis La. The needle can include a distal end 117a and a proximal end 119a. In some cases, a resilient boot 120a covers the proximal end 119a of the needle 102a. In certain arrangements, a removable cap 101a is configured to mate with the housing 104a and/or cover the needle 102a. As discussed in further detail below, the blood collection safety device 100a can be configured to protect and cover the distal and proximal ends 117a, 119a of the needle 102a after the distal end 117a has been removed from a patient. Such a configuration can reduce the likelihood of unintentional contact with distal end 117a as well as with the proximal end 119a.

In certain embodiments, the housing 104a can include a proximal body portion 141a, a distal body portion 142a, and an inner chamber 184a. The proximal body portion 141a can be received into and engage with a distal end 132a of the sleeve 106a. The distal body portion 142a can have a radially inwardly extending shoulder 146a and a distal aperture 147a, which can be configured to receive the plunger assembly 105a. For example, as shown, the distal aperture 147a can include notches 149a, which can be configured to accept corresponding portions of the plunger assembly 105a. Some embodiments of the housing 104a also include a needle support 181a (FIG. 7A), which can connect with the needle 102a and maintain the needle 102a substantially along the longitudinal axis.

In some embodiments, the plunger assembly 105a includes a sheath 107a, a biasing member 108a, and a piston 109a. In various embodiments, at least part of the plunger assembly 105a is configured to be received in the housing 104a and in the sleeve 106a.

Certain configurations of the sheath 107a have an elongate shape with a central lumen therethrough, a proximal end 161a, and a distal end 162a with a distal aperture 180a. The sheath 107a can also have a flange 185a, which can seat against the biasing member 108a. For example, the flange 185a can extend radially outward. In some cases, the flange 185a is continuous, e.g., an annular ring. In other cases, the flange 185a is discontinuous, e.g., one or more discrete radial projections. As shown in FIG. 7C, the sheath 109a can include a guide member 111a. In some cases, the guide member 111a extends radially inwardly. In some embodiments, the sheath 107a has an extension locking member 118a. In some configurations, the sheath 107a includes a retraction locking member 150a.

Figure 7A:
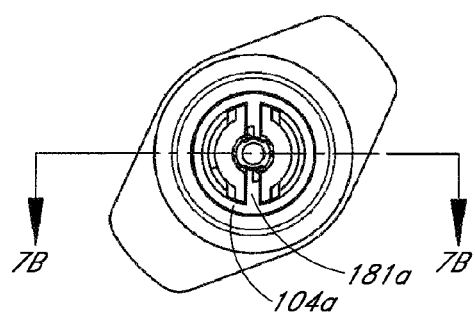
FIG. 7A illustrates a bottom view of the device of FIG. 6A in an initial position.
Figure 7C:
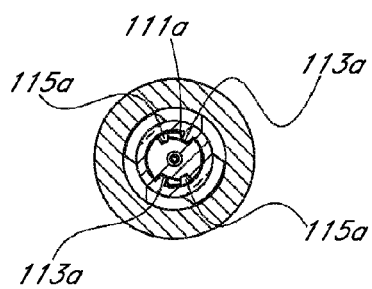
FIG. 7C illustrates a sectional view along the line 7C-7C of FIG. 7B.
Figure 7B:
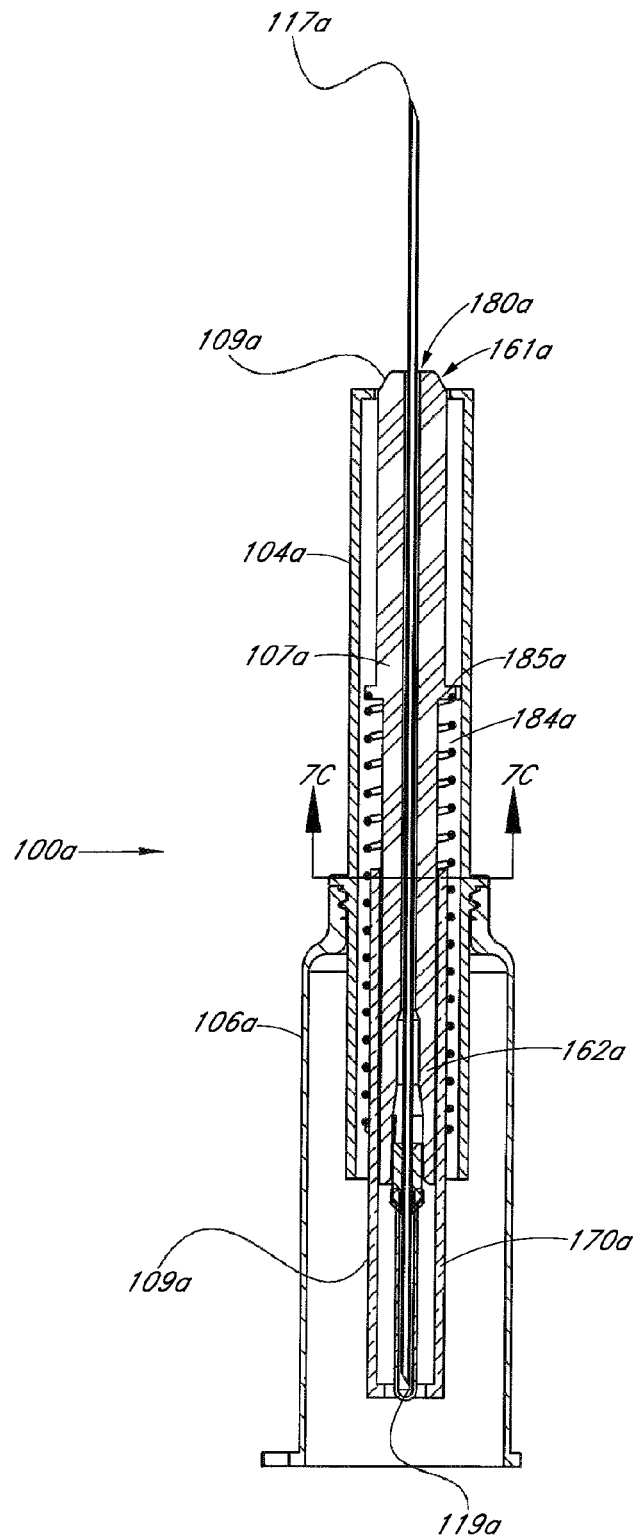
FIG. 7B illustrates a sectional view along the line 7B-7B of FIG. 7A.

As shown in FIG. 7B, the proximal end 161a can be configured to be received in the piston 109a. In some embodiments, the proximal end 161a includes one or more biased fingers 186a. For example, the fingers can be biased radially outward. However, in certain states of certain embodiments, such as is illustrated in FIG. 7B, the biased fingers 186a can be deflected radially inward within the piston 109a.

Figure 8A:
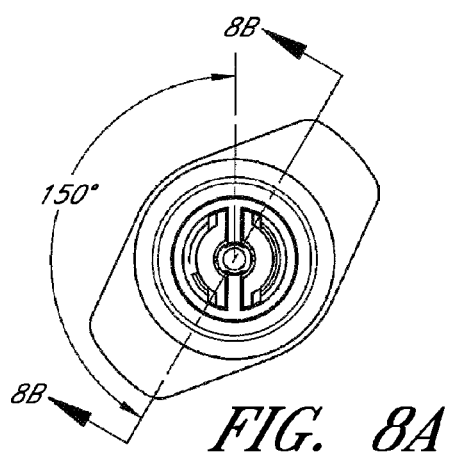
FIG. 8A illustrates a bottom view of the device of FIG. 6A in an extended and locked position.
Figure 8C:
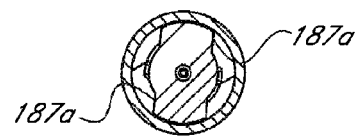
FIG. 8C illustrates a sectional view along the line 8C-8C of FIG. 8B.
Figure 8D:
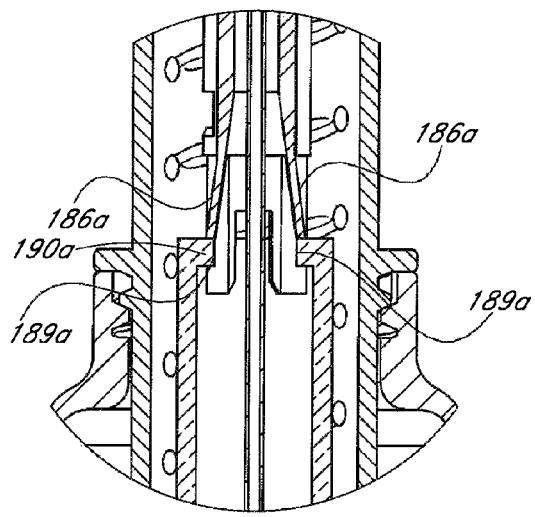
FIG. 8D illustrates a focused view of a portion of FIG. 8B.
Figure 8B:
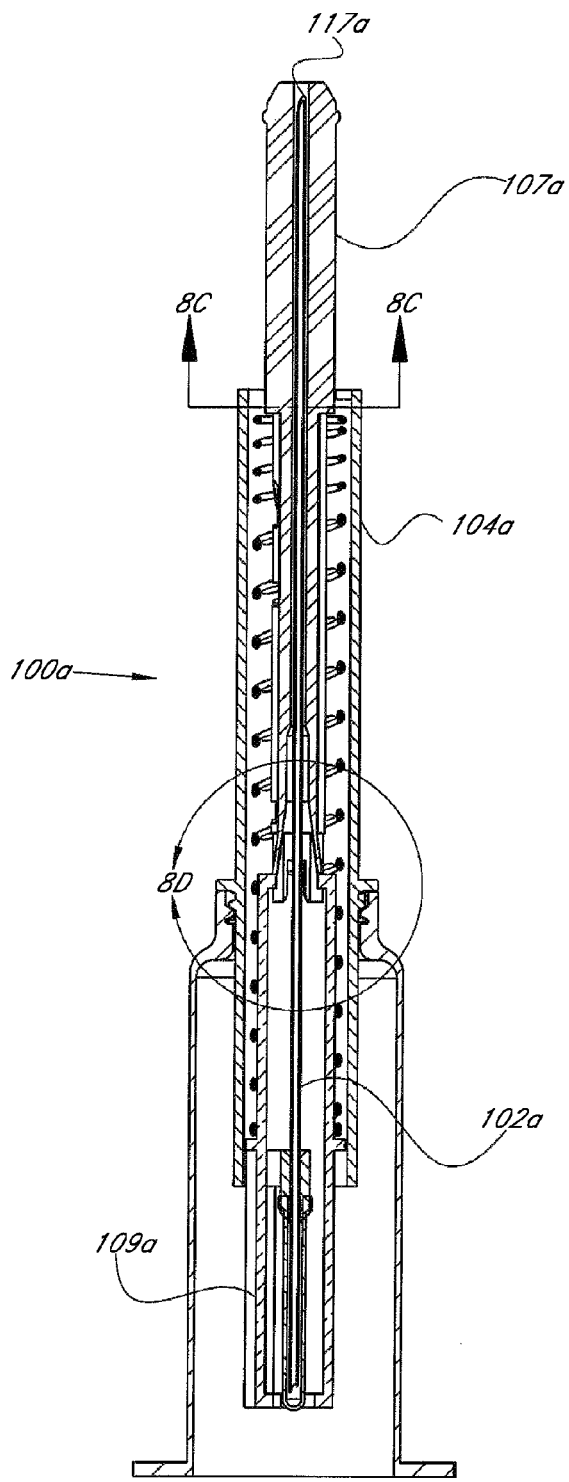
FIG. 8B illustrates a sectional view along the line 8B-8B of FIG. 8A.
Figure 10:
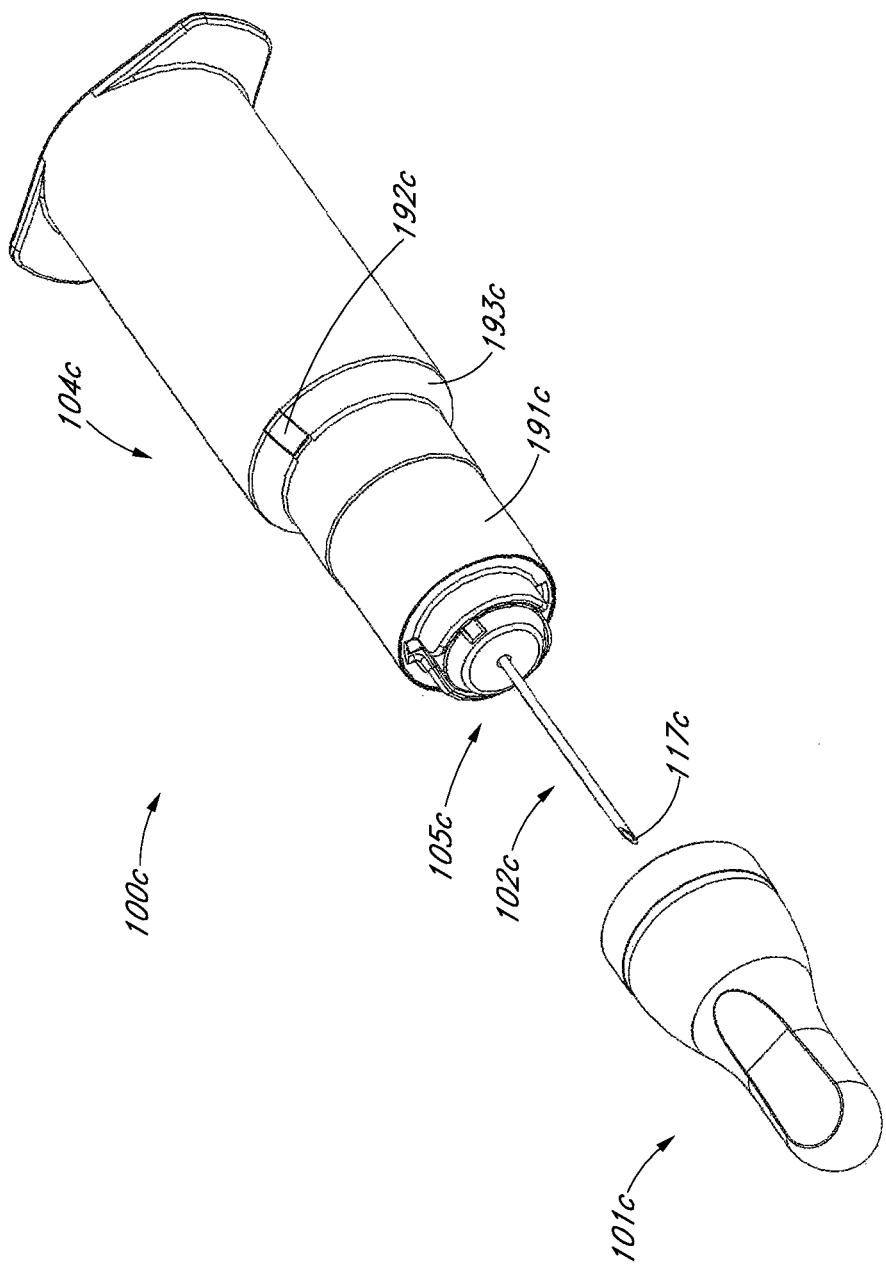
FIG. 10 illustrates a perspective view of another embodiment of a blood collection safety device, with a cap portion in a separated position.

Some embodiments of the proximal end 161a have a locking tooth 189a. As shown in FIG. 8D, the locking tooth 189a can extend radially outward. The locking tooth 189a can be configured to abut with a shoulder 190a of the piston 109a. Thus, in certain embodiments, the locking tooth 189a can inhibit distal removal of the sheath 107a from the piston 109a.

The piston 109a can include a generally elongate body 170a and a proximal flange 171a. The elongate body 170a can include a central lumen extending the length of the piston 109a, which is configured to allow passage of the distal end 117a of the needle 102a therethrough. In some embodiments, the elongate body 170a has radially extending wings 187a. In some configurations, the radially extending wings 187a extend substantially transverse to the locking tooth 189a. In certain configurations, the radially extending wings 187a terminate in a seat 188a for the biasing member 108a.

In some embodiments, the proximal flange 171a includes a radially inwardly extending proximal surface 172a, which can be configured to abut with the distal end of a blood collection vial. As shown in FIG. 6B, the piston 109a can include a longitudinally extending channel 173a that terminates in a stop 174a. The channel 173a can be configured to receive a portion of the needle support 181a of the housing 104a.

In some embodiments, the piston 109a has tracks similar to the tracks 113-115 of the piston 109 of the blood collection safety device 100. For example, the piston 109a can include an initial track 113a, a transfer track 114a, and an engagement track 115a. In some arrangements, the tracks 113a-115a are located on an external surface of the piston 109a. The tracks 113a-115a can be configured to slidingly receive the guide member 111a of the sheath 107a and can have a similar cross-sectional shape as the guide member 111a.

With reference to FIGS. 7A-7C, the blood collection safety device 100a is illustrated in an initial and ready-to-operate mode. The plunger assembly 105a is received in the housing 104a, which in turn is mated with the sleeve 106a. As shown, the sheath 107a is in a first position, which exposes the distal end 117a of the needle 102a, and the piston 109a is covering the proximal end 119a of the needle 102a. The needle support 181a of the housing 104a is received in the channel 173a of the piston 109a and is abutted with the stop 174a. The extension locking member 118a of the sheath 107a is received within the inner chamber 184a of the housing 104a and abuts against the shoulder 146a of the housing 104a. Thus, in the state of the embodiment shown, the biasing member 108a is compressed between the sheath 107a and the piston 109a, which are held in a stable first position relative to each other.

When a blood collection vial is distally pressed against the proximal flange 171a of the piston 109a, the piston 109a is moved distally. Similar to the discussion above concerning the tracks 113-115 of the blood collection safety device 100, the guide member 111a can be moved from the initial track 113a, to the transfer track 114a, and then to the engagement track 115a. The movement of the guide member 111a along the angled transfer track 114a can rotate the sheath 107a (relative to the piston 109a and the housings 104a, 106a).

The rotation of the sheath 107a can rotate the extension locking member 118a. In certain embodiments, rotation of the sheath 107a rotates the extension locking member 118a into longitudinal alignment with the notch 149a in the shoulder 146a of the housing 104a. In such cases, when the extension locking member 118a is aligned with the notch 149a, the extension locking member 118a can be allowed to pass distally through the notch 149a. The sheath 107a can thus be moved distally by the bias of the biasing member 108a.

With regard to FIGS. 8A-8D, the blood collection safety device 100a is illustrated in an extended and locked position. As shown, the sheath 107a has moved distally. In some cases, the flange 185a abuts with the shoulder 146a, thereby inhibiting further distal movement. Normally, after the distal end 117a of the needle 102a is removed from the patient, the sheath 107a covers the distal end 117a of the needle 102a.

In some embodiments, the sheath 107a moves distally such that the finger 186a is distal of the piston 109a, thereby permitting the bias of the finger 186a to deflect a portion of the finger 186a, e.g., radially outwardly. In the deflected position, the finger 186a can present an interference with the distal shoulder 190a of the piston 109a. Thus, the outwardly deflected finger 186a can inhibit the sheath 107a from being deflected proximally with respect to the piston 109a. For example, the finger 186a can inhibit the sheath 107a from being re-received into the piston 109a.

In some embodiments, the sheath 107a moves distally such the tooth 189a abuts the distal shoulder 190a of the piston 109a. In some such embodiments, the tooth 189a can inhibit the sheath 107a from being deflected distally with respect to the piston 109a.

In embodiments having both the finger 186a and the tooth 189a, when the finger 186a and the tooth 189a are engaged with the shoulder 190a, the plunger 105a assembly is locked, e.g., the sheath 107a and the piston 109a are substantially constrained relative to each other. In such configurations, the flange 185a abutting the shoulder 146a inhibits distal movement of the plunger assembly 105a and the needle support 181a abutting the stop 174a inhibits proximal movement of the plunger assembly 105a. Such embodiments of the blood collection safety device are therefore locked at both ends and can provide, for example, a further impediment or reduction in the opportunity to accidentally contact either end 117a, 119a of the needle 102a. For example, both the sheath 107a covering the distal end 117a and the piston 109a covering the proximal end 119a are substantially locked, e.g., cannot be moved along the longitudinal axis to expose the ends 117a, 109a.

FIGS. 9A and 9B illustrate a further embodiment of a blood collection safety device 100b. Several features and components of the blood collection safety device 100b are identical or similar in form and function to those described above with respect to the blood collection safety devices 100, 100a, and have been provided with like numerals, with the replacement of "a" with "b". To the extent that parts of the blood collection safety device 100b differ from those of the blood collection safety devices described above, some of those differences are described and explained herein. Any features and/or components of the disclosed embodiments can be combined or used interchangeably.

As shown, the blood collection safety device 100b can include an outer housing 104b that is unitary, rather than two discrete portions (e.g., a distal housing and a proximal housing). Such a configuration can, for example, assist in manufacturability and/or assembly of the blood collection safety device 100b. In some embodiments, the housing 104b is monolithically formed, such as by molding.

FIGS. 10-14 illustrate a further embodiment of a blood collection safety device 100c. Several features and components of the blood collection safety device 100c are identical or similar in form and function to those described above with respect to the blood collection safety devices 100-100b, and have been provided with like numerals, with the addition of "c" (e.g., 100c rather than 100 or 100a). To the extent that parts of the blood collection safety device 100c differ from those of the blood collection safety devices described herein, some of those differences are described and explained below. Any features and/or components of the disclosed embodiments can be combined or used interchangeably.

The blood collection safety device 100c can include a removable cap 101c, a needle 102c with a distal end 117c, an outer housing 104c, and a plunger assembly 105c. In some embodiments, the outer housing 104c includes a gap 192c. For example, the gap 192c can be disposed in a radially reducing shoulder 193c of the outer housing 104c. In some cases, the gap 192c is a through-hole between the outside and the inside of the outer housing 104c.

Figure 11:
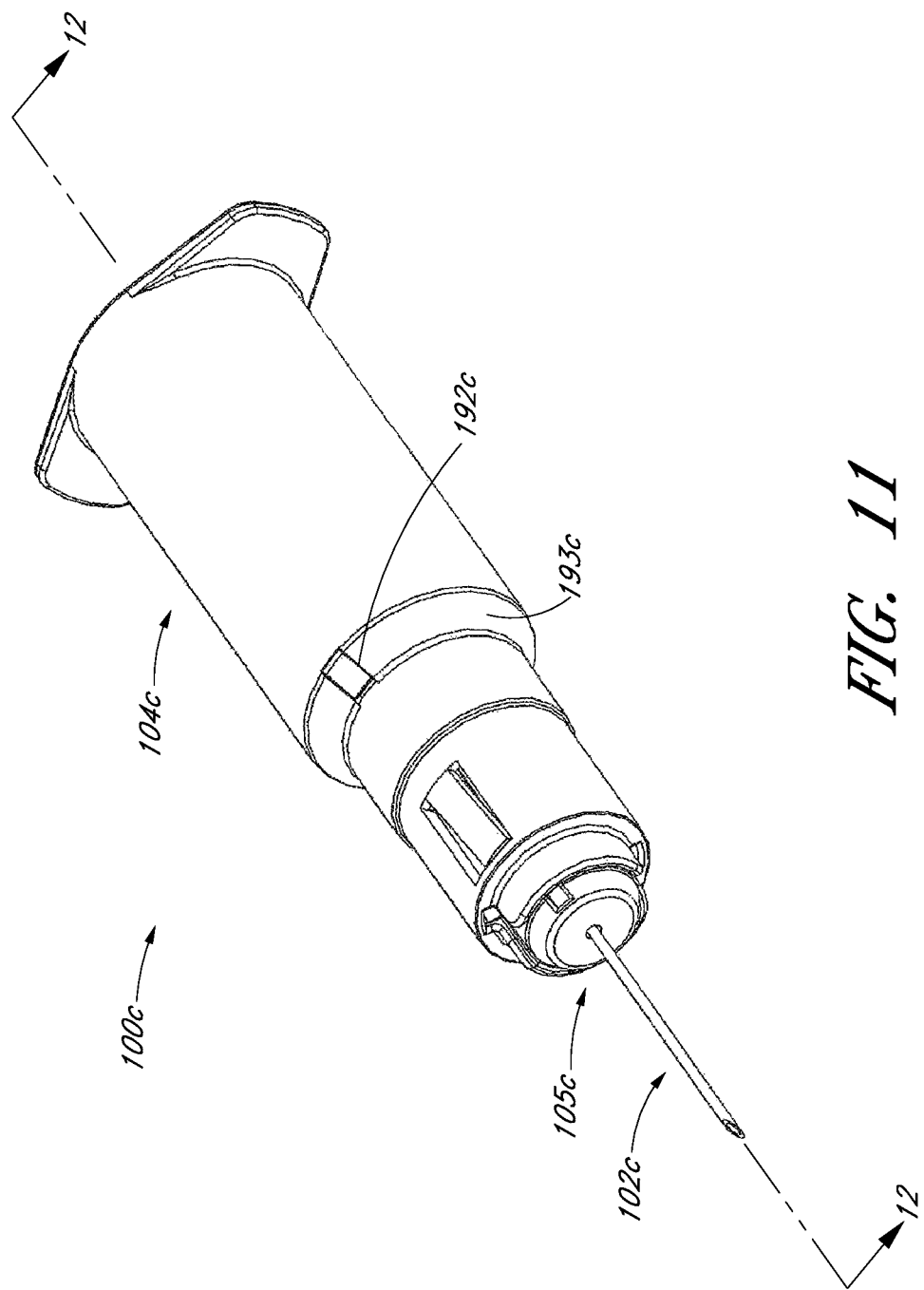
FIG. 11 illustrates a perspective view of the device of FIG. 10 with a label removed.

In some embodiments, the blood collection safety device 100c includes a tamper-resistant label 191c. For example, the label 191c can be adhered to the housing 104c and the cap 101c. In some configurations, the label 191c is configured to rip, break, crease, or otherwise provide an indication upon the cap 101c being separated from the housing 104c. In some cases, the label 191c provides an area for the user to mark, e.g., the user can use ink to note the patient name, date of use of the device, etc. In certain configurations, the label 191c is removable from the housing 104c (FIG. 11).

Figure 12:
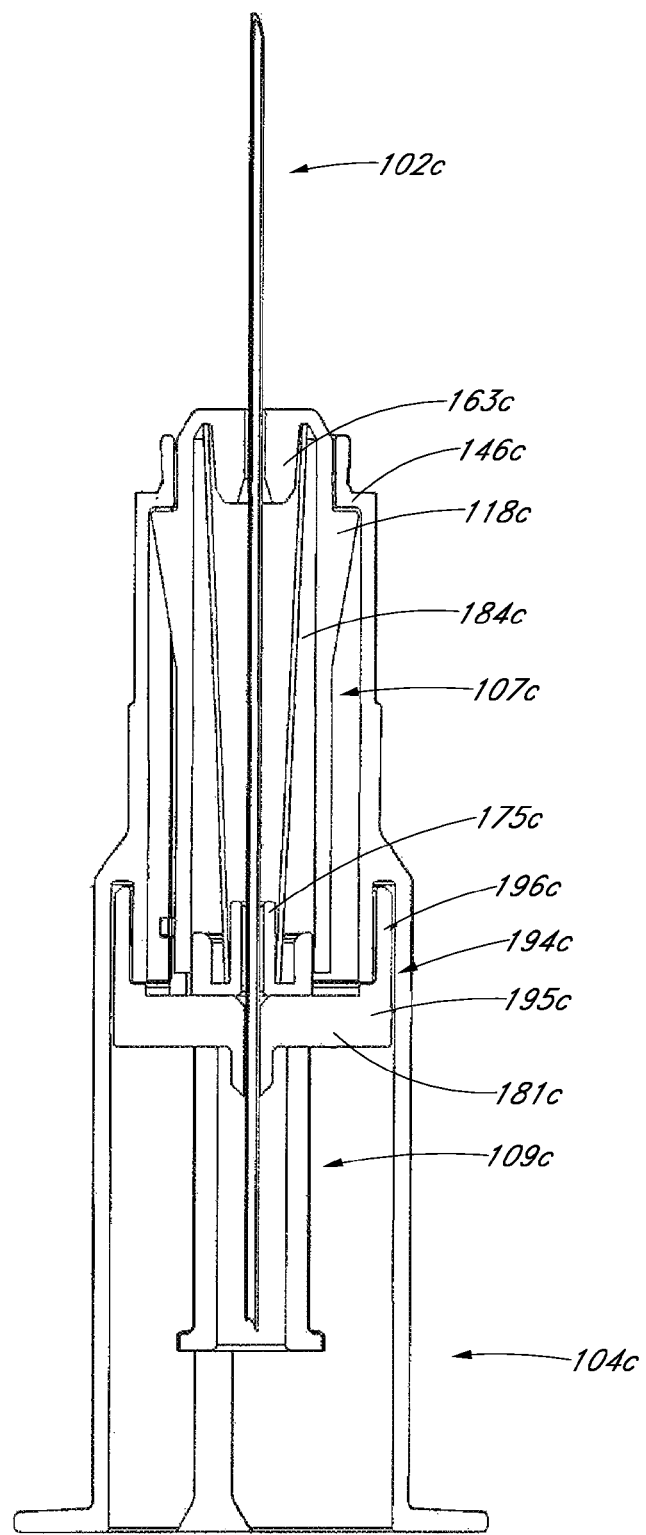
FIG. 12 illustrates a sectional view along the line 12-12 of FIG. 11.

As shown in FIG. 12, in some embodiments, the blood collection safety device 100c includes a hub 194c. The hub 194c can connect, e.g., by adhesive, with the needle 102c through a central passage. The hub 194c can include a needle support 181c, an annular portion 195c, and a distally extending arm 196c. In some cases, the distally extending arm 196c is configured to engage the gap 192c of the outer housing 104c. For example, in certain cases the arm 196c includes a wedge, tab, tooth, or otherwise, which can snap into the gap 192c, thereby coupling the hub 194c with the outer housing 104c. In certain arrangements, such coupling is generally permanent, e.g., the hub 194c is not removed from outer housing 104c during normal and intended use of the blood collection safety device 100c.

Figure 13:
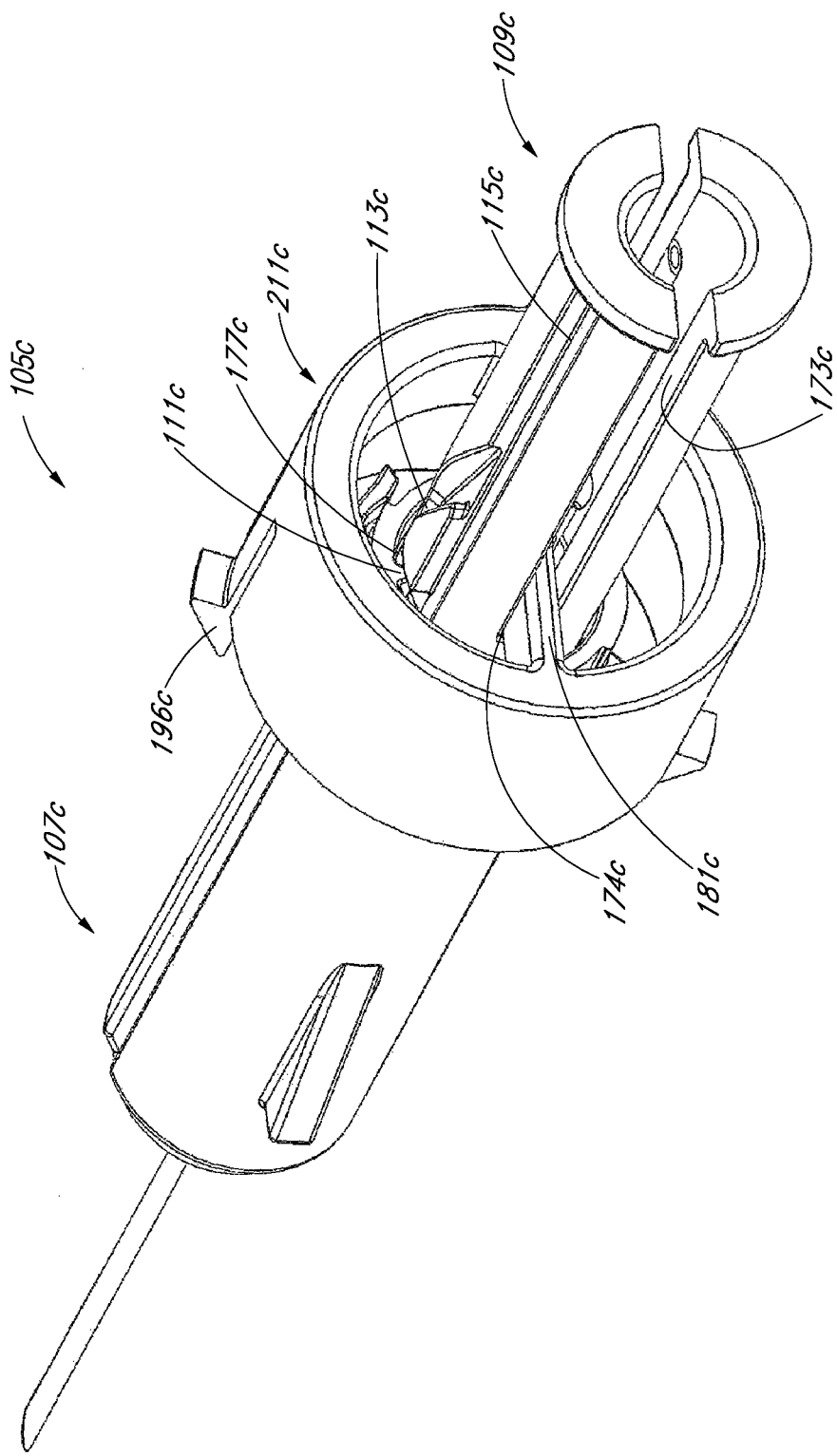
FIG. 13 illustrates a perspective view of a plunger assembly for the device of FIG. 10.
Figure 14:
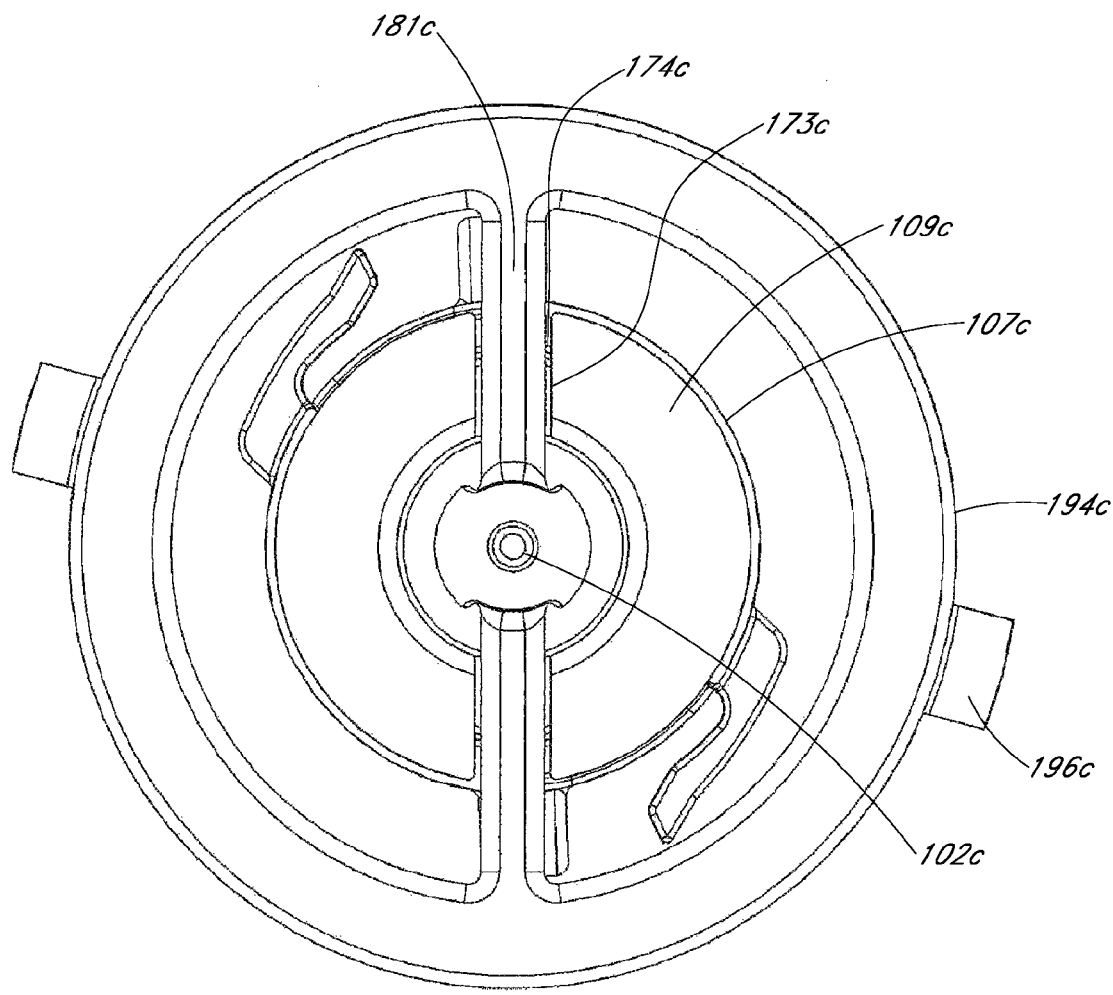
FIG. 14 illustrates a bottom view of the plunger assembly of FIG. 13.

In some embodiments, such a configuration can facilitate assembly of the blood collection safety device 100c. For example, as shown in FIGS. 13 and 14, in some cases the needle 102c, plunger assembly 105c, and the hub 194c are assembled as a separate inner unit, then that inner unit is mated with the outer housing 104c. In some such embodiments, the piston 109c is mated with the hub 194c. For example, the needle support 181c of the hub 194c can be received in a channel 173c of the piston. A proximal portion of the biasing member 108c can be seated on a distally extending portion 175c of the piston 109c. The biasing member can be received into the central lumen of the sheath 107c and can be seated on the distally extending portion 163c. The sheath 107c can be moved toward the piston 109c (or the piston 109c can be moved toward the sheath 107c), thereby compressing the biasing member 108c. A guide member 111c of the sheath 107c can be received through a distal open notch 178c (not shown) in the engagement track 115c of the piston 109c.

In some embodiments, the sheath 107c can be rotated with respect to the piston 109c (or the piston 109c can be rotated with respect to the sheath 107c) such that the guide member 111c is received in an assembly track 177c. In some embodiments, the guide member 111c rides up the incline of the assembly track 177c until reaching a generally flat face 179c (not shown), at which point the guide member 111c can snap to the bottom of the initial track 113c. In such a condition, the sheath 107c and the piston 109c are held generally stable against the bias of the biasing element 108c. For example, distal movement of the sheath 107c and proximal movement of the piston 109c can be inhibited by a proximal wall of the initial track 113c of the piston 109c abutting the guide member 111c of the sheath 107c.

In some embodiments, the inner unit (e.g., needle 102c, plunger assembly 105c, and hub 194c) is received into the housing 104c. The distally extending arm 196c can be coupled with the gap 192c. The extension locking member 118c can be received in the inner chamber 184c and can abut the shoulder 146c. In some such configurations, the plunger assembly 105c is thus retained by the housing 104c. In some embodiments, the sleeve 106c is mated with the housing 104c.

FIGS. 15-27 illustrate yet a further embodiment of a blood collection safety device 200. Several features and components of the blood collection safety device 200 are identical or similar in form and function to those described above with respect to the blood collection safety devices 100-100c. To the extent that parts of the blood collection safety device 200 differ from those of the blood collection safety devices described herein, some of those differences are described and explained below. Any features and/or components of the disclosed embodiments can be combined or used interchangeably.

Figure 15:
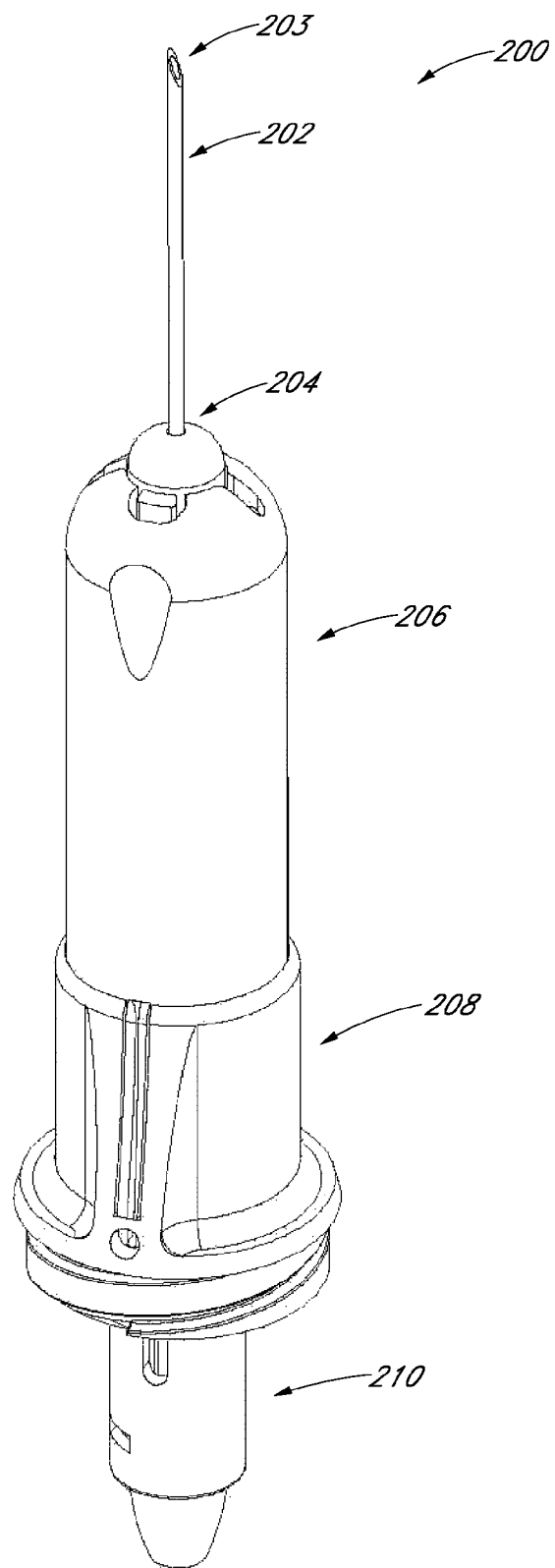
FIG. 15 illustrates a perspective view of another embodiment of a blood collection safety device having a housing, sheath, intermediate member, and piston.
Figure 15A:
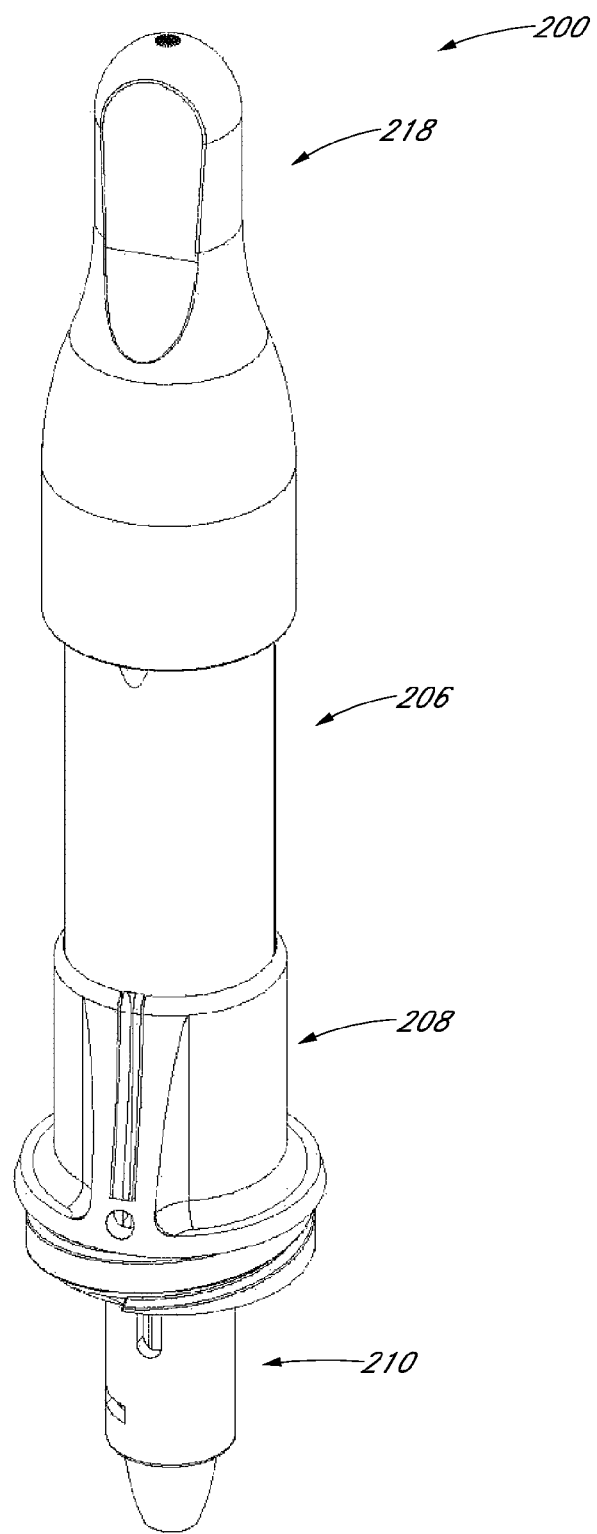
FIG. 15A illustrates a perspective view of the device of FIG. 15 coupled with a cap.
Figure 15B:
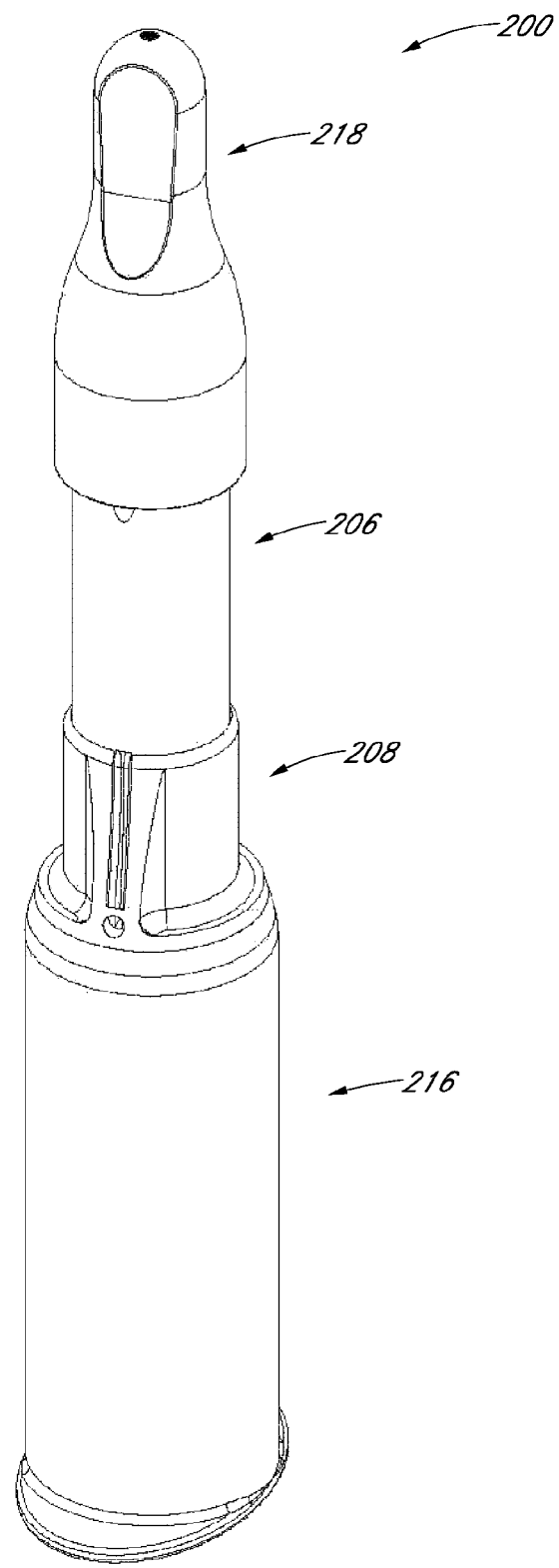
FIG. 15B illustrates a perspective view of the device of FIG. 15A coupled with a sleeve.
Figure 15C:
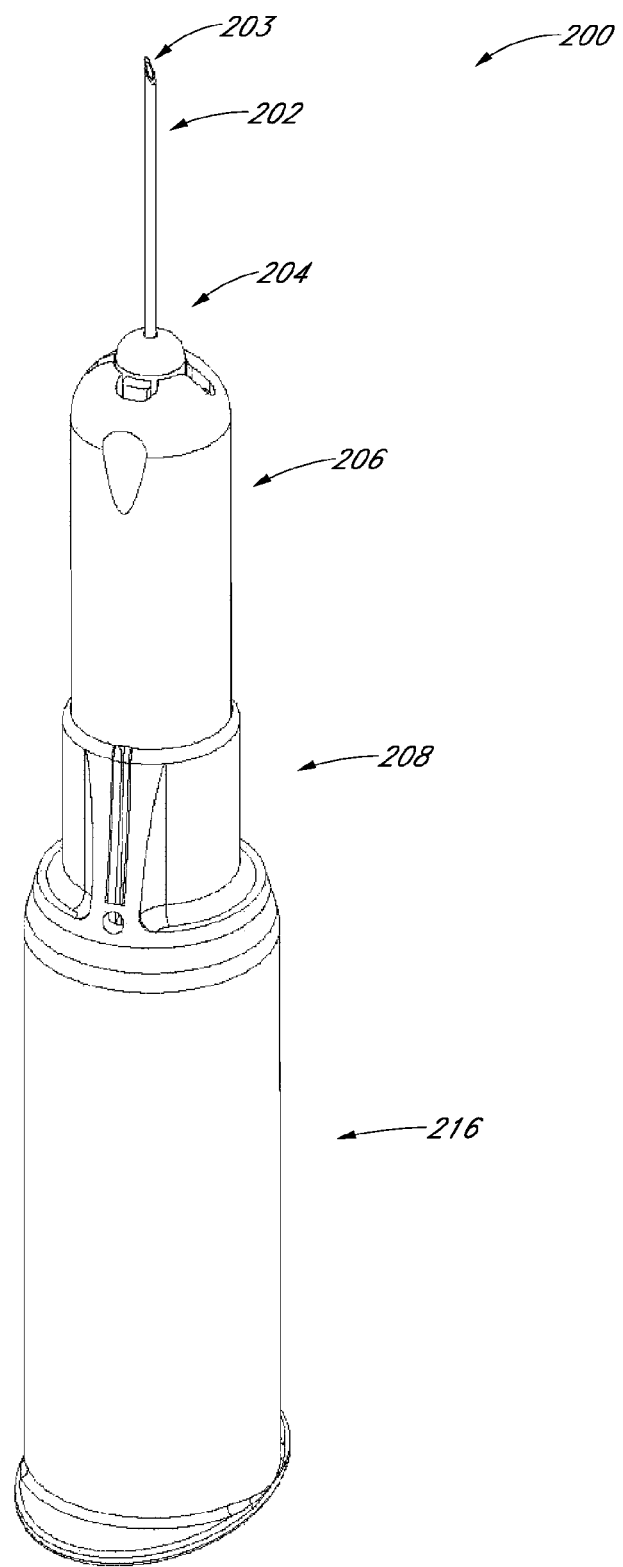
FIG. 15C illustrates a perspective view of the device of FIG. 15B with the cap removed.
Figure 16:
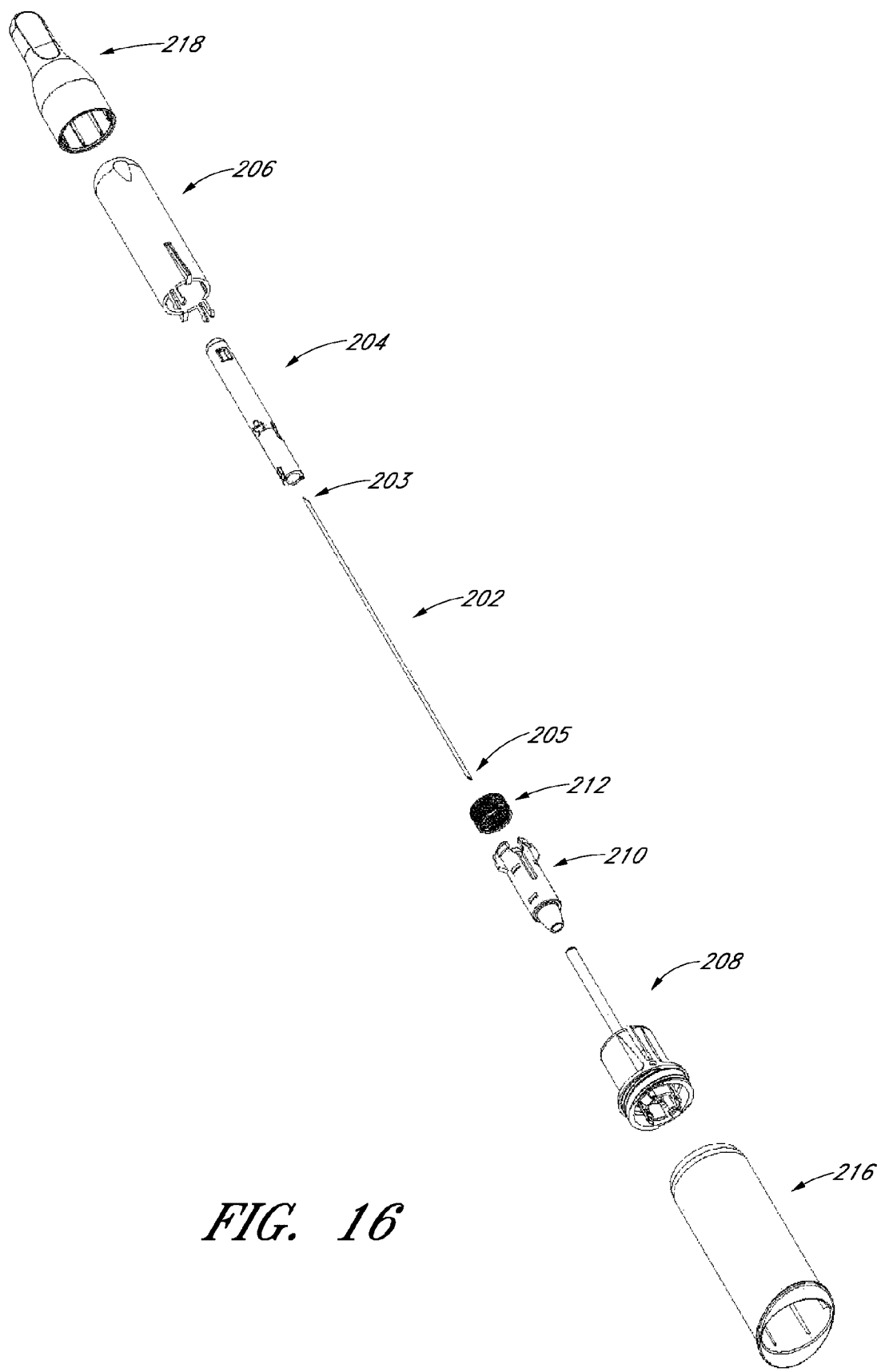
FIG. 16 illustrates a perspective exploded view of the device of FIG. 15, including the cap and the sleeve.

With reference to the assembled views of FIGS. 15-15C, as well as the exploded view of FIG. 16, an embodiment of the blood collection safety device 200 is illustrated. In certain configurations, the device 200 can be configured to mate with a blood collection vial or other container or adaptor (not shown). As illustrated, some embodiments of the device 200 include a needle 202, a sheath 204, and a housing 206 that are generally aligned along a longitudinal axis L. Certain implementations further include an intermediate member 208 and a piston 210, which can also be generally aligned along the axis L. Some embodiments include a biasing member 212, such as a spring. In certain variants, the device 200 includes a resilient boot 214. In some implementations, the device 200 includes a sleeve 216.

The blood collection safety device 200 can comprise features and components that automatically inhibit, prevent, or otherwise discourage using the device 200 multiple times, or inadvertently inserting the needle 202 into a second person, such as a healthcare worker or another patient. For example, certain embodiments of the blood collection safety device 200 include a locking system that automatically or passively inhibits access to the distal end 203 of the needle 202 after a single use of the device 200. Such embodiments can, for example, reduce the likelihood of transferring blood or tissue-born diseases from one patient to another. The locking system and/or reuse-inhibition features of the device 200 could be used with many different types of medical and non-medical products.

In certain embodiments, the device 200 includes a cap 218. The cap 218 can be configured to couple with the sheath 204, housing 206, or intermediate member 208. Some variants of the cap 218 can receive at least a portion of the needle 202, such as the distal end 203. Certain variants of the cap 218 can reduce or prevent contamination of the needle 202, for example, during shipping and storage of the device 200. Typically, the cap 218 is removed prior to a blood collection procedure, at which time the cap 218 can be discarded.

In some implementations, the needle 202 includes a distal end 203 and a proximal end 205, each of which can comprise a sharp end. The needle 202 can have an intermediate aperture 207 (not shown) that extends radially through a side of the needle 202. In certain variants, fluid passing through the needle 202 can exit the needle 202 via the intermediate aperture 207.

The sheath 204 can be configured to expose the distal end 203 of the needle 202 in certain modes of the device 200. In other modes, the sheath 204 can be configured to cover (e.g., include a portion that extends distally beyond) the distal end 203 of the needle 202. In some embodiments, as will be discussed in further detail below, the sheath 204 can be configured to reciprocate, telescope, or otherwise be at least partly received within the housing 206. In some embodiments, the sheath 204 is configured to rotate with respect to the housing 206.

The piston 210 can be configured to expose the proximal end 205 of the needle 202 in certain modes of the device 200. In other modes, the piston 210 can be configured to cover (e.g., include a portion that extends proximally beyond) the proximal end 205 of the needle 202. In some embodiments, as will be discussed in greater detail below, the piston 210 can be configured to reciprocate, telescope, or otherwise be at least partly received within the intermediate member 208.

Figure 17:
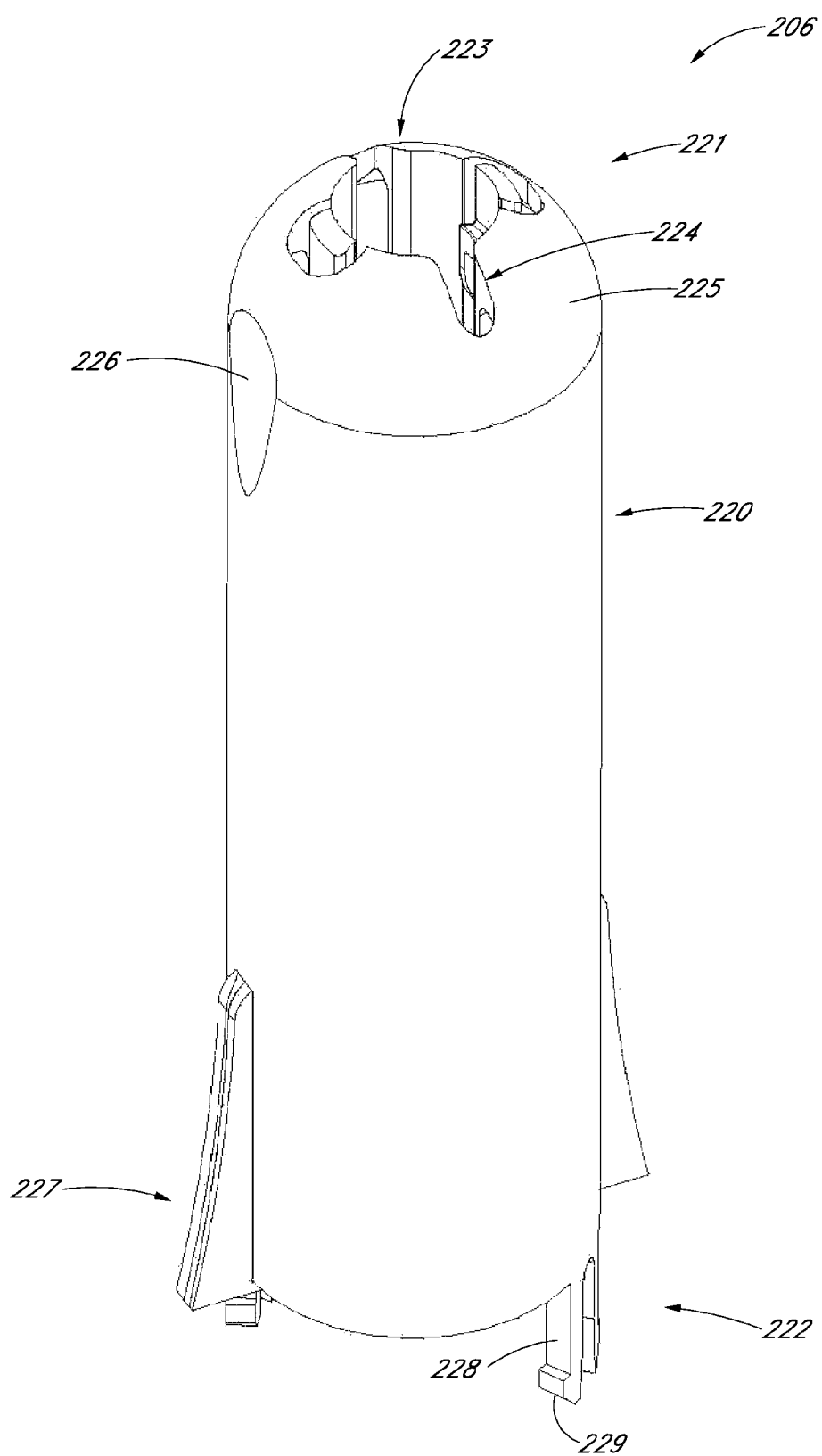
FIG. 17 illustrates a perspective view of an embodiment of the housing of the device of FIG. 15.
Figure 17A:
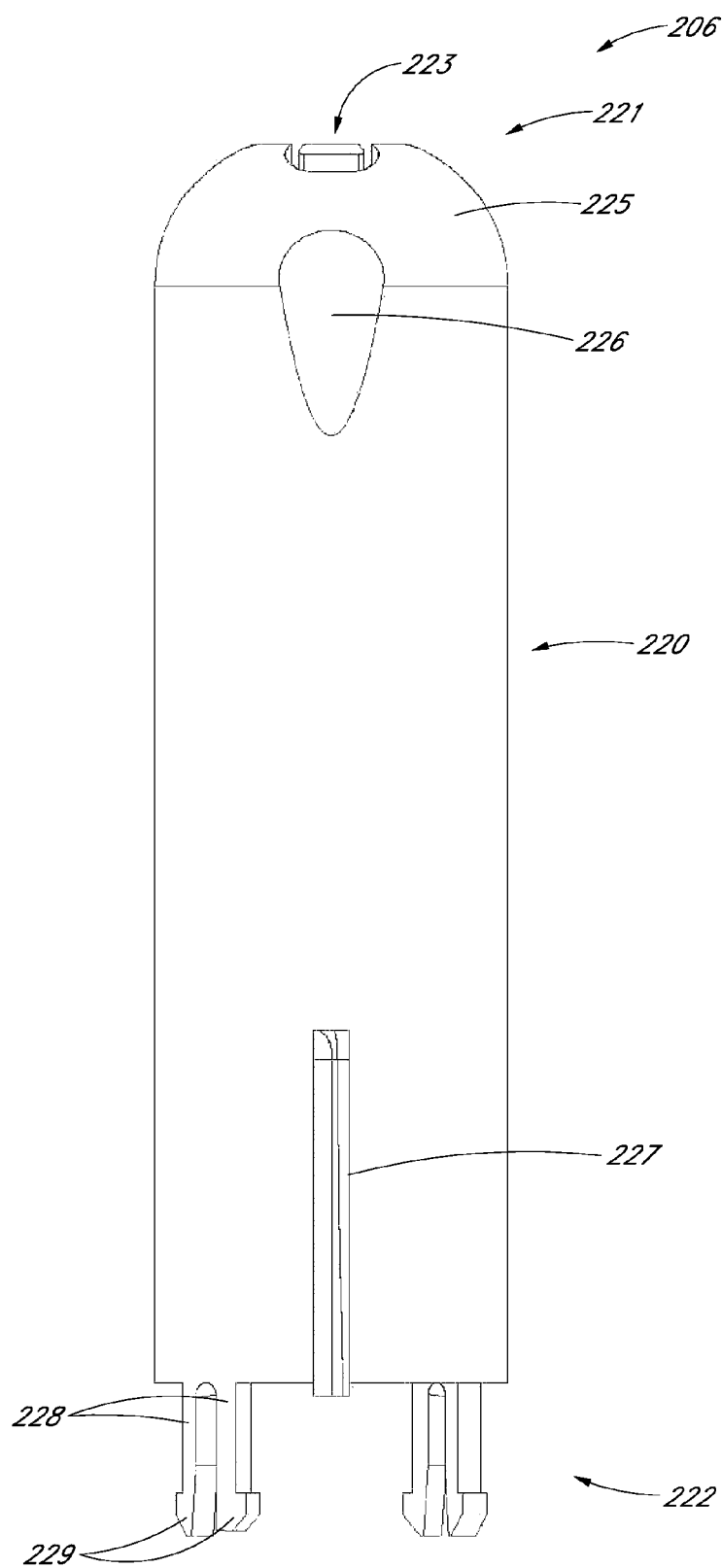
FIG. 17A illustrates a front view of the housing of FIG. 17.
Figure 17B:
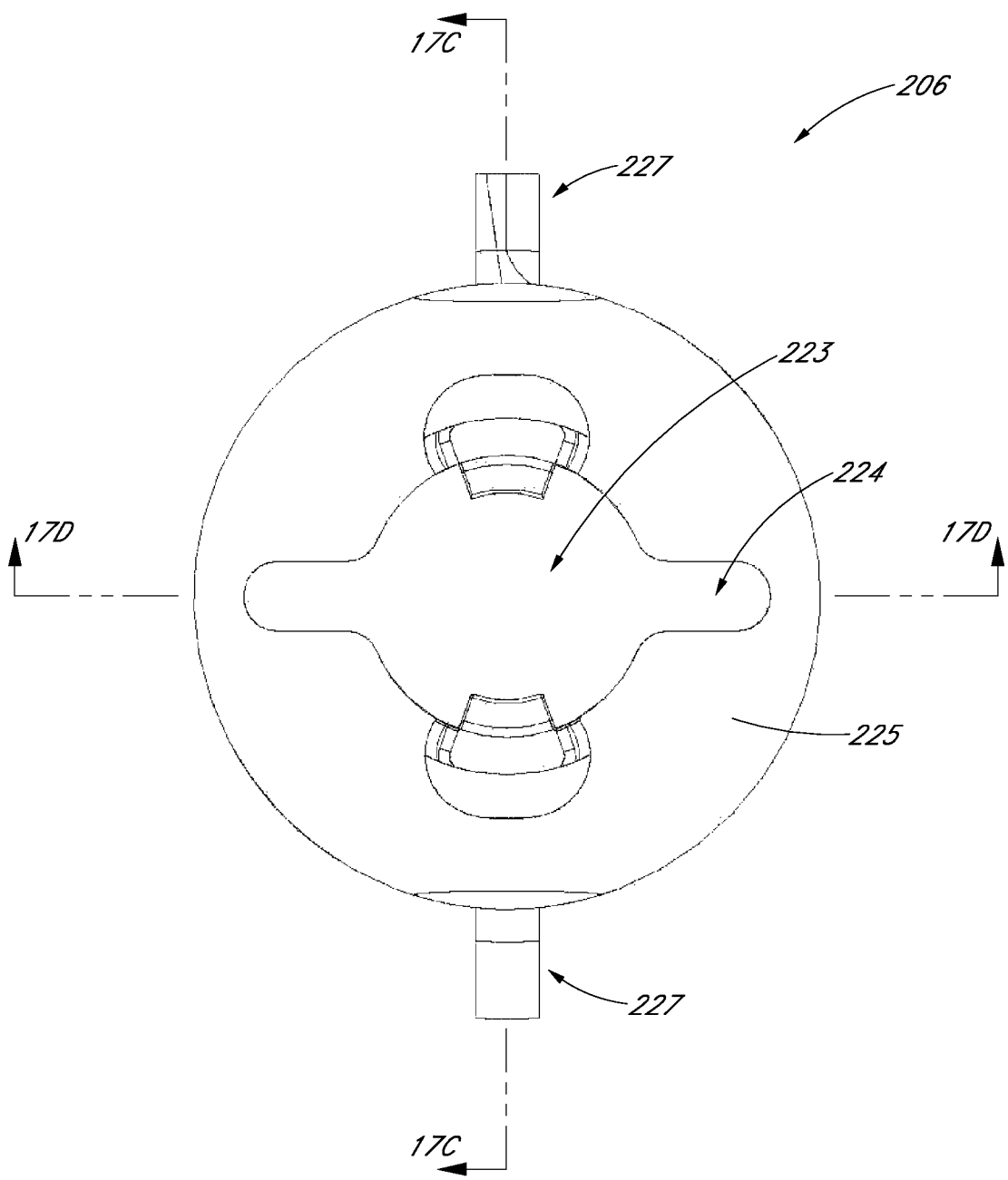
FIG. 17B illustrates a top view of the housing of FIG. 17.
Figure 17C:
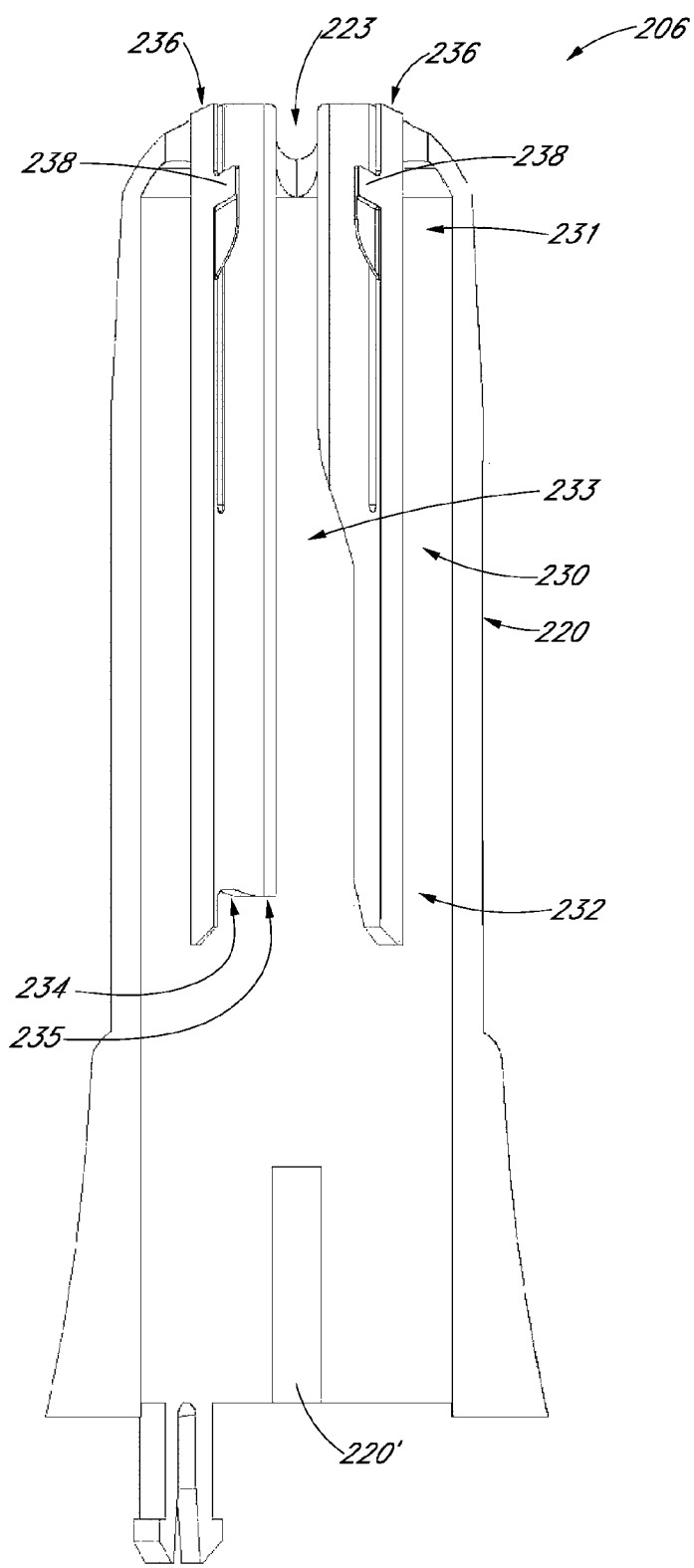
FIG. 17C illustrates a cross-sectional view along the line 17C-17C of FIG. 17B.
Figure 17D:
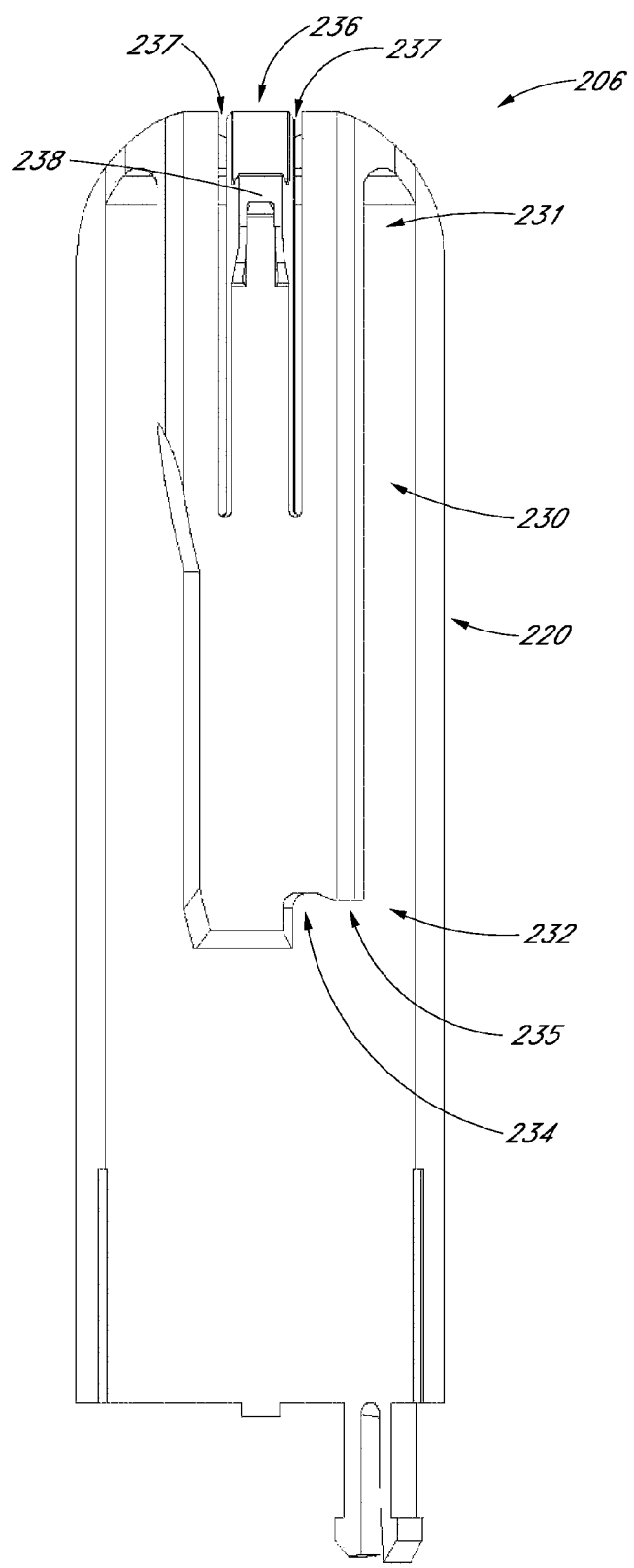
FIG. 17D illustrates a cross-sectional view along the line 17D-17D of FIG. 17B.

With regard to FIGS. 17-17D, an embodiment of the housing 206 is illustrated. In some implementations, the housing 206 includes an elongate hollow body 220, a distal end 221, and a proximal end 222. The housing 206 can also include a distal aperture 223. In certain embodiments, the distal aperture 223 includes one or more indication channels 224. As illustrated, some embodiments of the indication channels 224 extend radially outwardly. Certain embodiments include a radially inwardly extending shoulder 225. For example, the shoulder 225 can have a generally conical or generally hemispherical shape. Some implementations have a recess 220' (FIG. 17C) on an inner wall of the body 220.

In some embodiments, the body 220 includes an indication element, such as an indication face 226. In certain variants, the indication face 226 comprises a pointed, flattened, or recessed portion. In some embodiments, the indication face 226 comprises an indicia, such as an arrow or line (e.g., applied with paint or ink). In certain implementations, the indication face 226 is generally aligned with the bevel of the distal end 203 of the needle 202, thereby providing a visual and/or tactile indication of the orientation of the needle bevel. In some embodiments, a user is able to readily discern the orientation of the bevel, which can be helpful in performing certain blood draw procedures.

In some implementations, the housing 206 includes one or more long and narrow generally radially extending positioning members, such as prongs 227. In certain embodiments, the prongs 227 extend radially outwardly from the body 220 and have a generally sloped shape. In some variants, the housing 206 has long and narrow generally longitudinally extending members, such as tabs 228, that extend proximally from the body 220. The tabs 228 can include one or more securing members, such as clasps 229.

As illustrated in FIGS. 17C and 17D, some embodiments of the housing 206 include a frame 230 within the body 220. In certain implementations, the frame 230 includes a distal end 231, a proximal end 232, and a longitudinal conduit 233. In some embodiments, the proximal end 232 includes first and second movement regulating members, such as a valley 234 and a ramp 235. As will be discussed in more detail below, in some embodiments, the longitudinal conduit 233, valley 234, and ramp 235 are configured to interface with features of the sheath 204 to restrain and/or allow distal movement of the sheath 204. The longitudinal conduit 233 can be generally aligned with the indication channel 224.

Certain implementations of the frame 230 have at least one resilient flexing member, such as a leg 236. Typically, the leg 236 is configured to flex, e.g., radially outward. In certain implementations, the housing 206 is configured to facilitate flexing the leg 236. For example, some embodiments have longitudinal gaps 237 with the leg 236 disposed therebetween. In some variants, the distal aperture 231 includes a recessed portion configured to allow for movement of the leg 236 (see FIG. 17C). In some embodiments, the leg 236 includes an interference member, such as a tooth 238, edge, ledge, or the otherwise. Some variants of the tooth 238 have a curved or sloped face. As illustrated, in some embodiments, the tooth 238 is angled toward the distal end 221.

Figure 18:
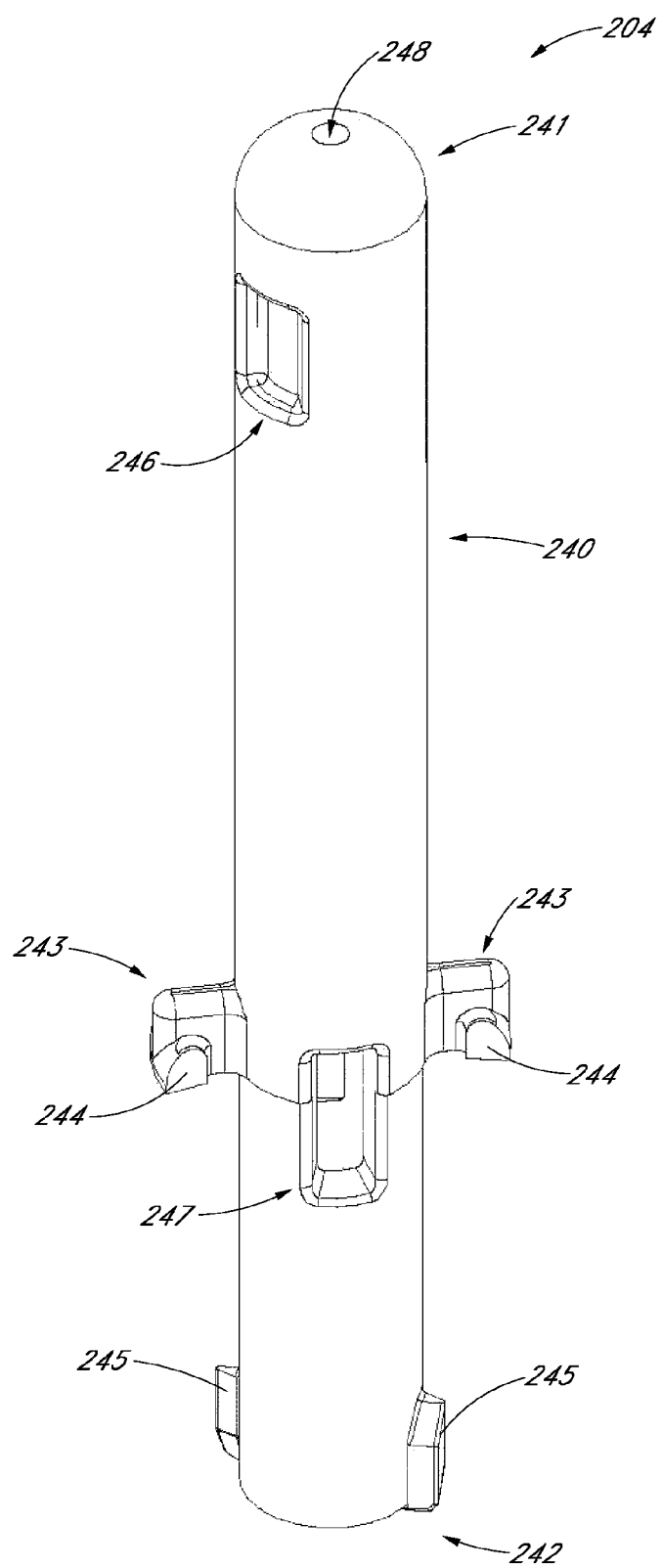
FIG. 18 illustrates a perspective view of an embodiment of the sheath of the device of FIG. 15.
Figure 18A:
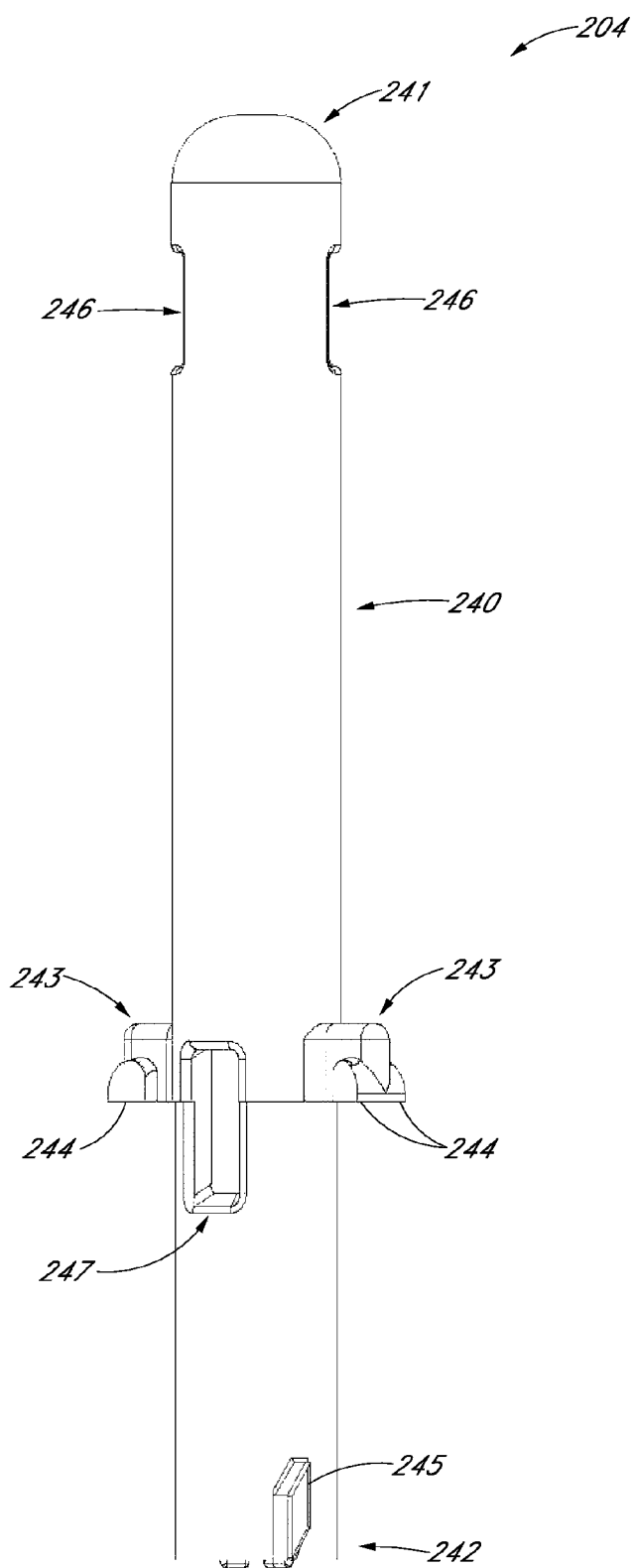
FIG. 18A illustrates a front view of the sheath of FIG. 18.
Figure 18B:
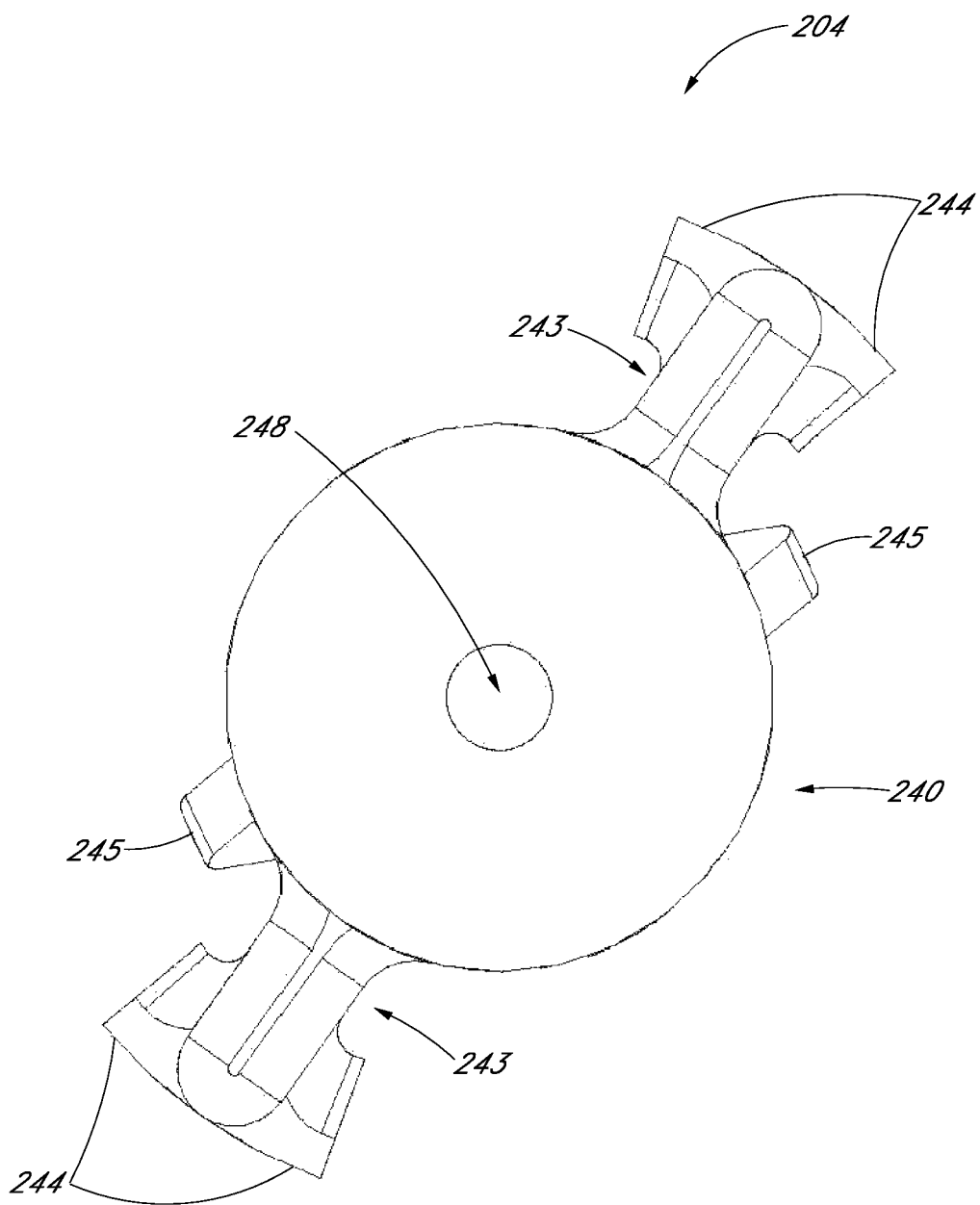
FIG. 18B illustrates a top view of the sheath of FIG. 18.

With reference to FIGS. 18-18B, an embodiment of the sheath 204 is illustrated. In some embodiments, the sheath 204 includes a hollow casing 240, a distal end 241, and a proximal end 242. Typically, at least some of the distal end 241 of the sheath 204 is sized and shaped to be able to pass through the distal aperture 223 of the housing 206. In some embodiments, the sheath 204 has a longitudinal length that is less than a longitudinal length of the housing 206.

As illustrated, certain implementations of the sheath 204 include a distal hole 248, which can be configured to allow a portion of the needle 202 to pass therethrough. In some embodiments, the distal hole 248 is sized so as to reduce the chance of, or generally avoid, the escape of blood through the distal hole 248 (e.g., in case blood leaks from the needle 202 after the blood collection procedure). For example, in some embodiments, a diameter of the distal hole 248 is about equal to an outside diameter of the needle 202. In some embodiments, the diameter of the distal hole 248 is substantially less than an outside diameter of the sheath 204. For example, in certain embodiments, the ratio of the diameter of the distal hole 248 to the outside diameter of the sheath 204 is less than or equal to about ⅓, about ¼, about ⅛, about 1/16, values in between, or otherwise.

In some embodiments, the sheath 204 includes radially extending guide members, such as wings 243, that extend radially outward from the casing 240. Some embodiments of the wings 243 extend in generally opposite directions. In certain implementations, the wings 243 include circumferentially extending guide members, such as winglets 244. In certain embodiments, the winglets extend circumferentially, relative to the casing 240. In some variants, the winglets 244 extend generally perpendicular to the wings 243. In certain implementations, the sheath 204 includes at least one base guiding member, such as a foot 245 (e.g., at the proximal end 242). In some embodiments, the foot 245 extends generally radially outward from an outer surface of the casing 240. In certain variants, the foot 245 has one or more slanted surfaces. In some embodiments, the wings 243 extend radially outward further than the foot 245.

In some embodiments, the sheath 204 includes a distal opening 246. In certain variants, the sheath 204 includes a proximal opening 247. As illustrated, in some embodiments, the distal and/or proximal openings 246, 247 are radial openings in the casing 240. As will be discussed in greater detail below, in certain embodiments, the distal opening 246 and the proximal opening 247 can be configured to interface with features of the housing 206 to inhibit certain movements of the sheath 204.

Some implementations of the sheath 204 have a longitudinally tapered configuration. For example, the proximal end 242 of the sheath 204 can be radially thicker than the distal end 241 of the sheath 204. In some embodiments, the distal end 241 is radially thicker than the proximal end 242. A tapered configuration can, for example, facilitate manufacturability. For example, a tapered configuration can aid in removing the sheath 204 from molds, dies, tooling, or otherwise.

Figure 19:
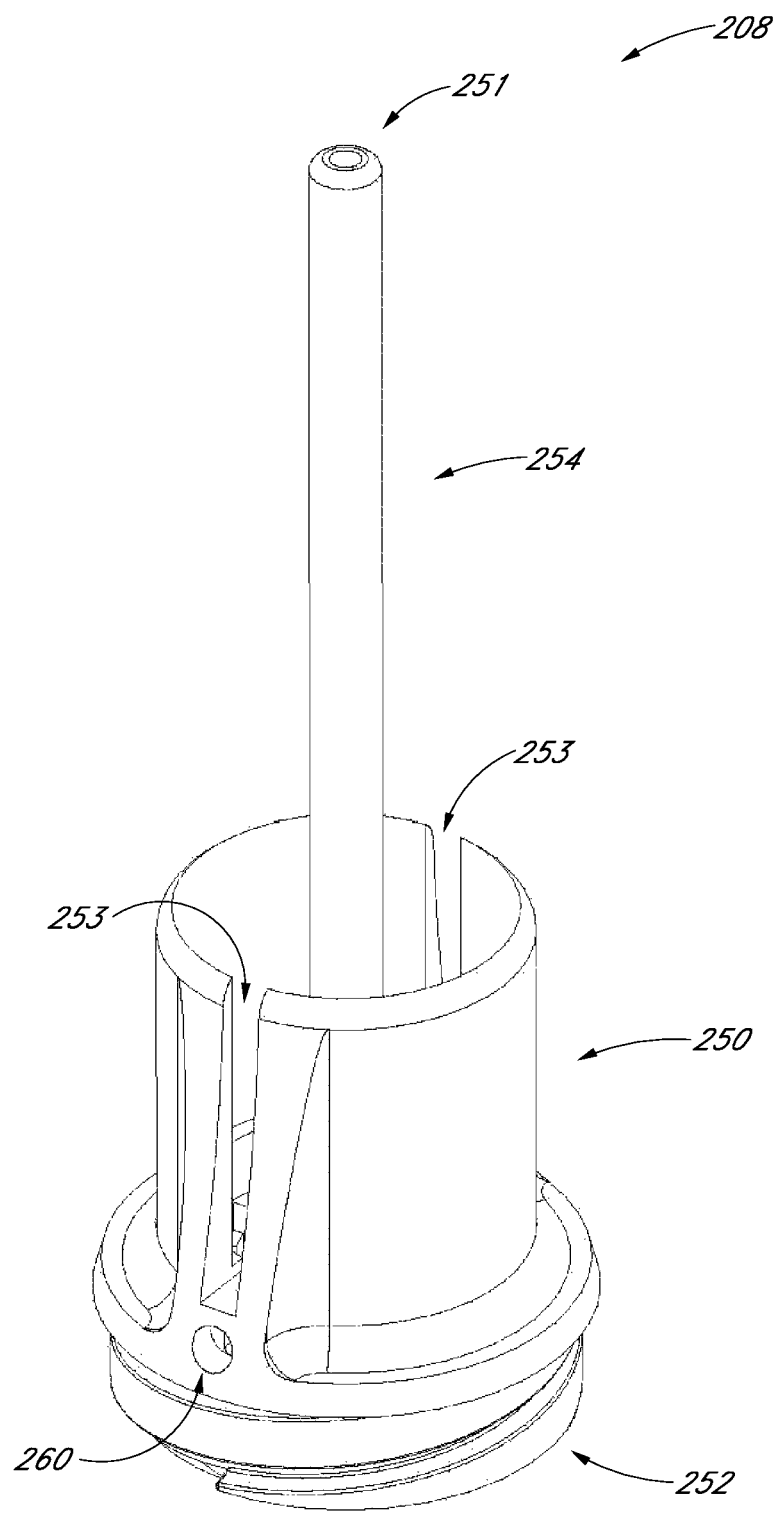
FIG. 19 illustrates a perspective view of an embodiment of the intermediate member of the device of FIG. 15.
Figure 19A:
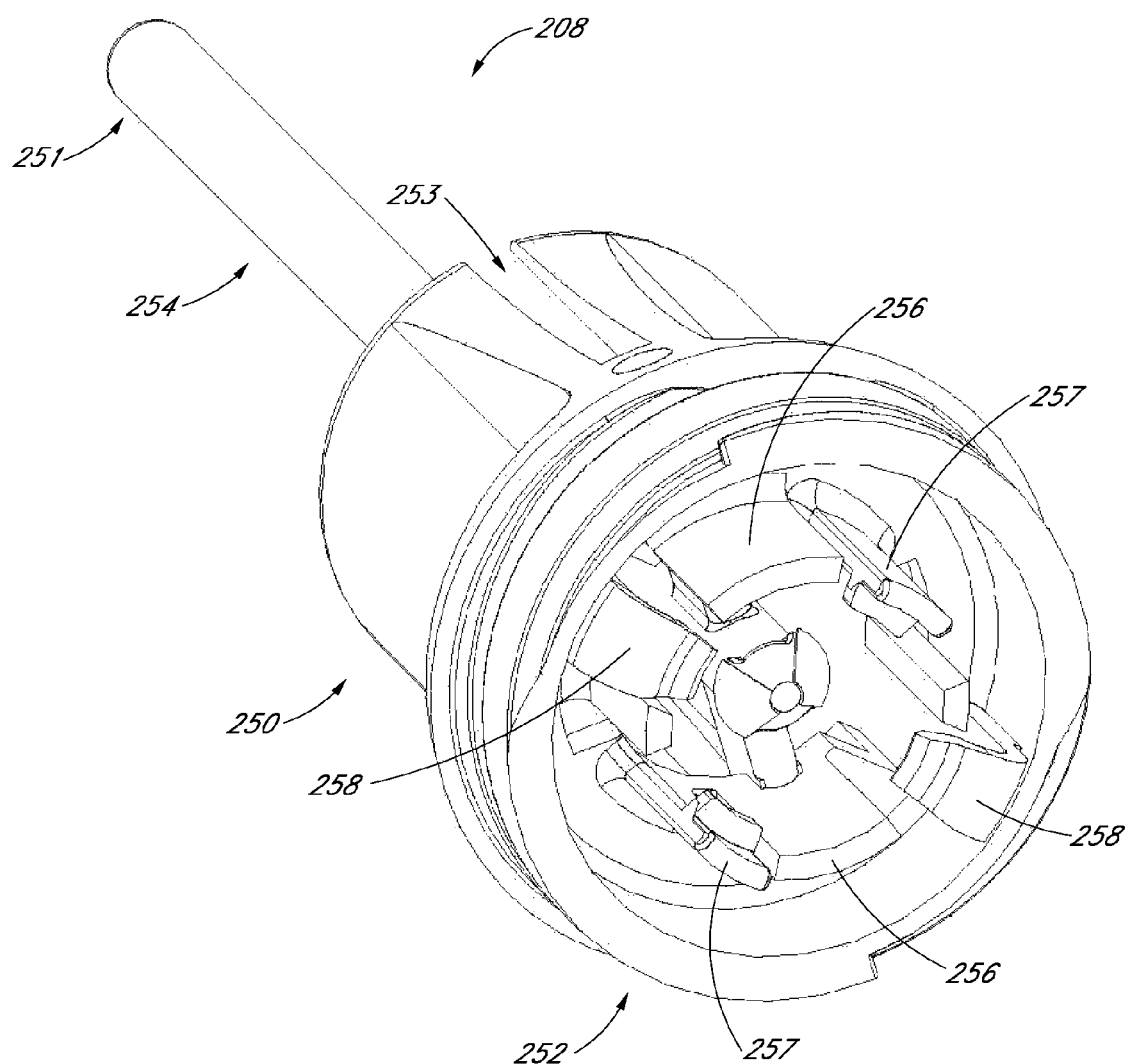
FIG. 19A illustrates a rear perspective view of the intermediate member of FIG. 19.
Figure 19B:
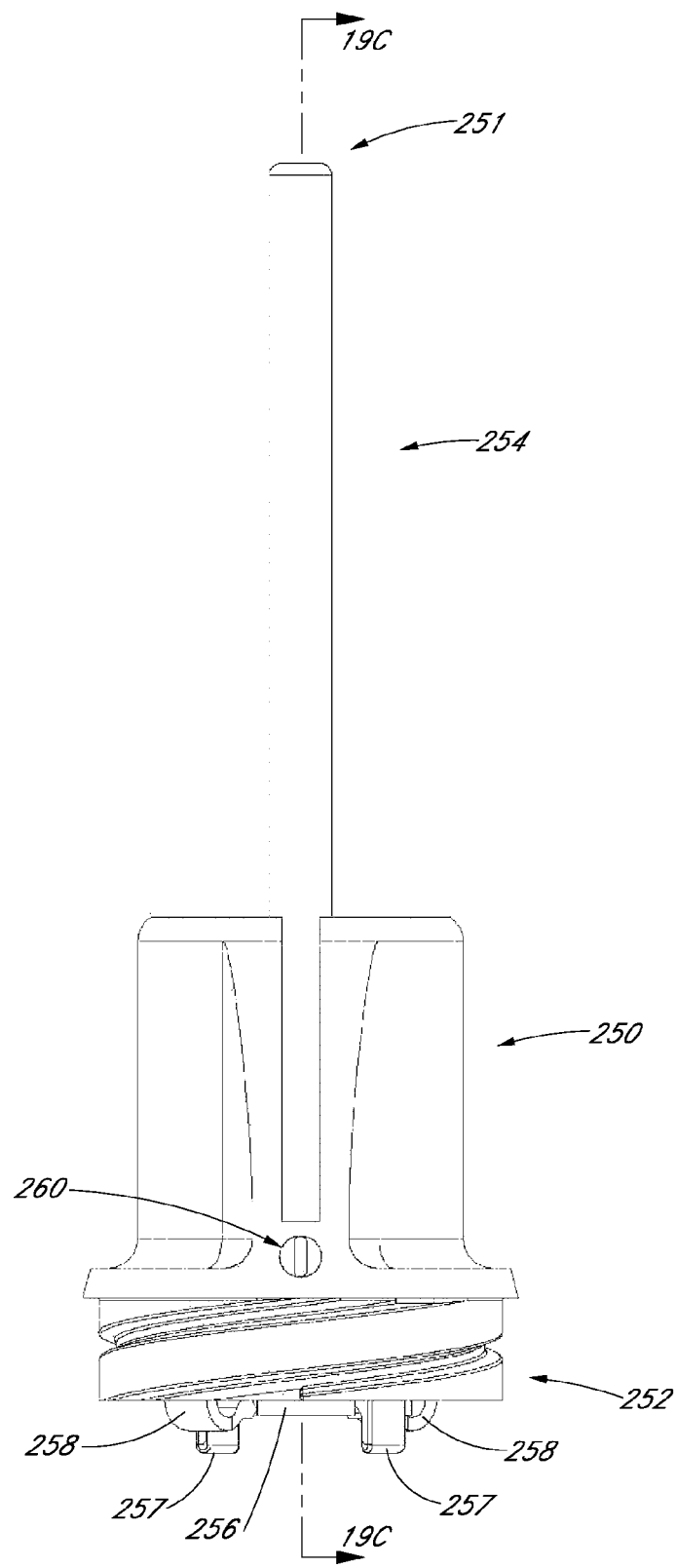
FIG. 19B illustrates a front view of the intermediate member of FIG. 19.
Figure 19C:
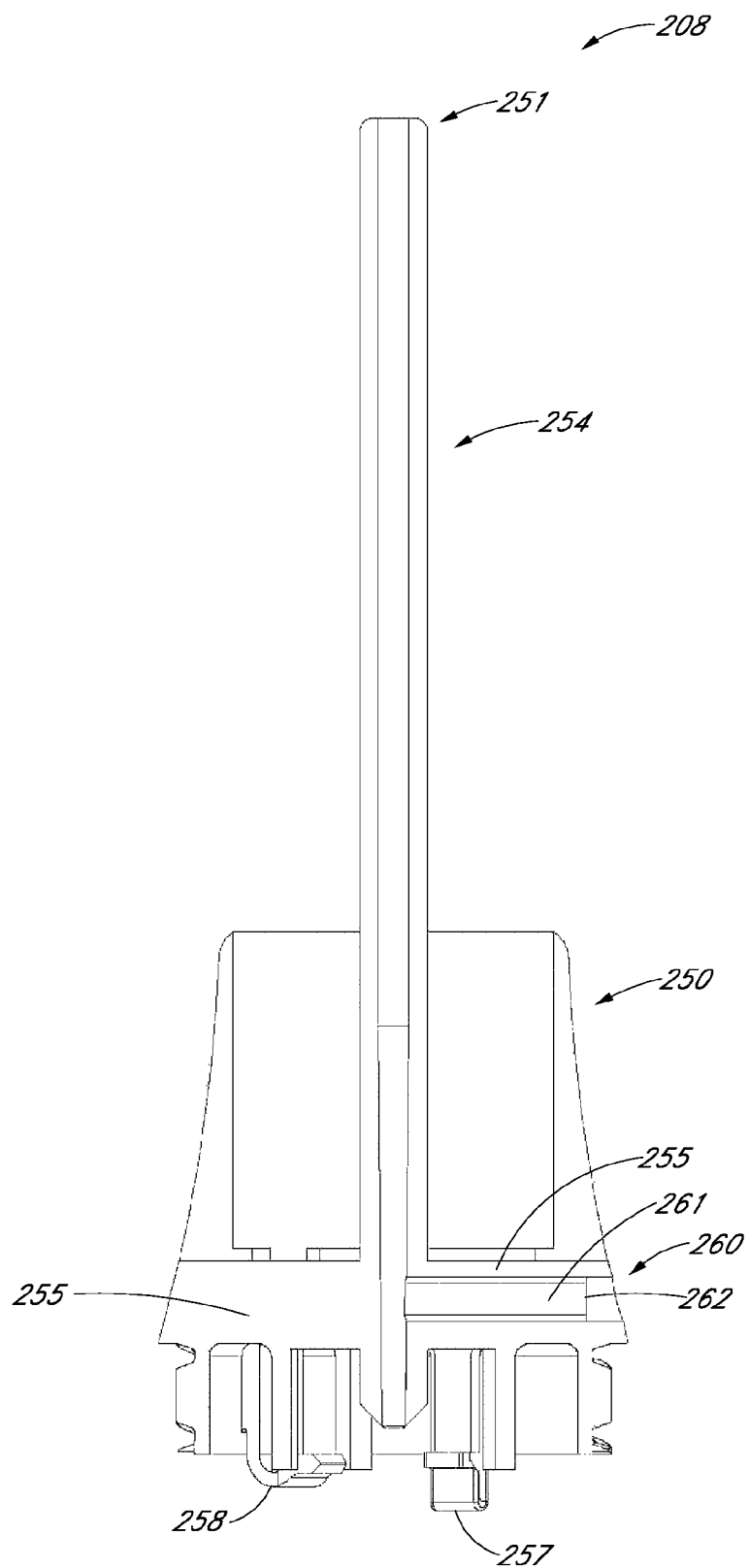
FIG. 19C illustrates a cross-sectional view along the line 19C-19C of FIG. 19B.
Figure 19D:
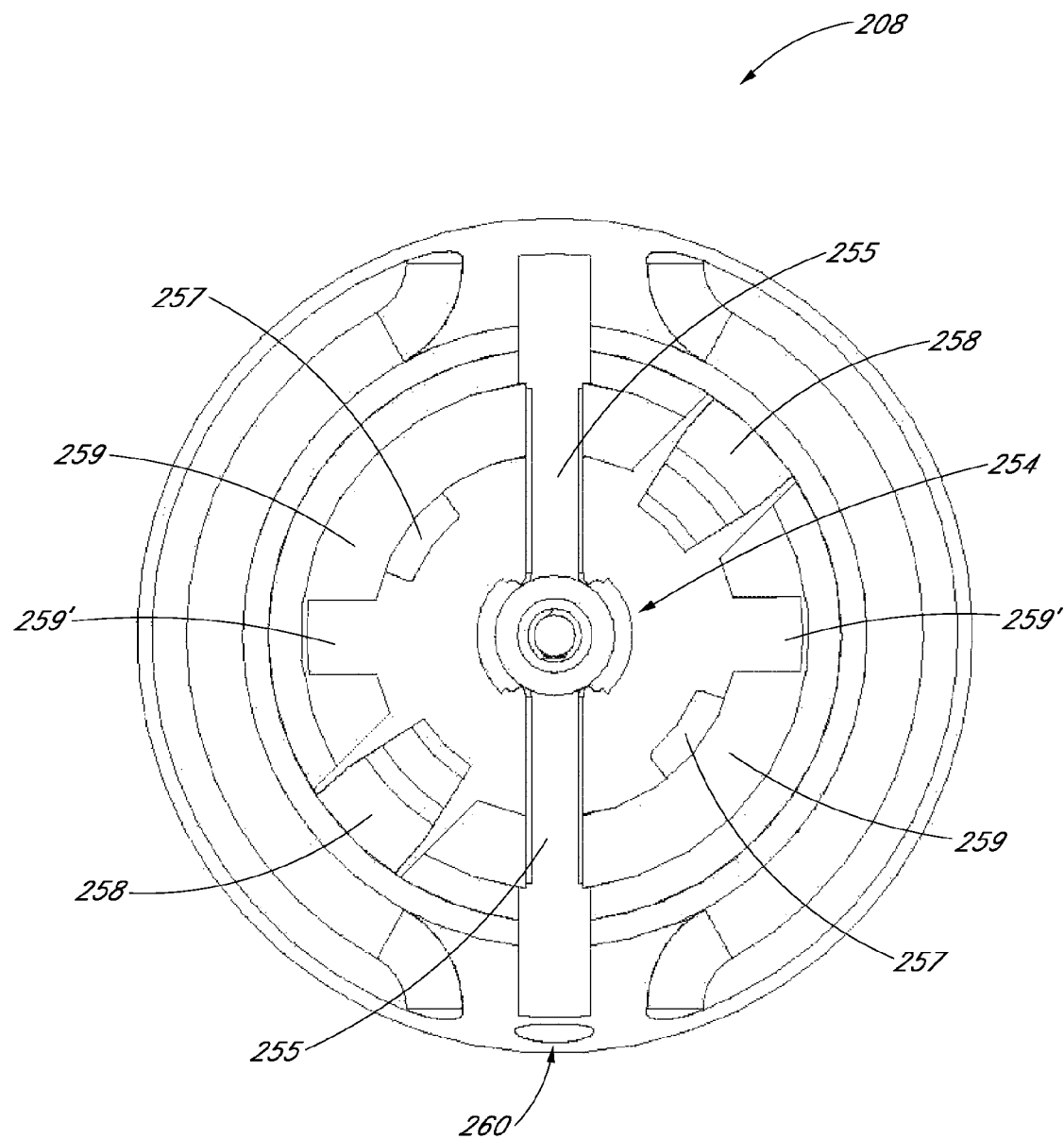
FIG. 19D illustrates a top view of the intermediate member of the intermediate member of FIG. 19.

With regard to FIGS. 19-19D, an embodiment of the intermediate member 208 is illustrated. Some embodiments of the intermediate member 208 include a body portion 250, distal end 251, and proximal end 252. In certain variants, the proximal end 252 comprises a connection member, such as threads. In some embodiments, the body portion 250 includes an engagement structure, such as longitudinal slots 253.

In certain implementations, the intermediate member 208 includes a movement facilitating member, such as a hollow rail 254. In some implementations, the rail 254 has a longitudinal length that is greater than the longitudinal length of the sheath 204. In some embodiments, the rail 254 is coupled with the body portion 250 via one or more arms 255 that extend radially outward from the rail 254 (see FIG. 19D). In certain implementations, the arms 255 extend in generally opposite directions. In some embodiments, the body portion 250 includes a radially inwardly extending movement limiting member, such as a shoulder 259. In some variants, the shoulder 259 includes a movement enabling structure, such as one or more spaces 259'.

In some embodiments, the body portion 250 and the rail 254 are a single unitary component. For example, the body portion 250 and the rail 254 can be molded as a monolithic item. Such a configuration can, for example, facilitate assembly of the device 200. In some embodiments, the body portion 250 and the rail 254 are separate components. Such a configuration can, for example, facilitate molding or otherwise forming each of these components. For example, in some implementations, the slots 253 include key receiving portions and the arms 255 include keyed ends, which can be configured to engage with the key receiving portions. In certain such embodiments, the key receiving portions have a generally triangular or keystone shape, and the keyed ends have a corresponding shape.

In some implementations, the rail 254 has a longitudinally tapered configuration. For example, a proximal end of the rail 254 can be radially thicker than a distal end of the rail 254. In some embodiments, the distal end of the rail 254 is radially thicker than the proximal end of the rail 254. As noted above, a tapered configuration can, for example, facilitate manufacturability. For instance, a tapered configuration can aid in removing the rail 254 from molds, dies, tooling, or otherwise.

In some embodiments, the rail 254 is configured to facilitate movement of the sheath 204 along, or adjacent to, at least a portion of the rail 254, as will be discussed in more detail below. For example, the rail 254 can be configured to facilitate sliding movement of the sheath 204 along the rail 254. Such a configuration can, for example, reduce the likelihood of misalignment (e.g., kinking, bending, or other movement askew from the longitudinal axis L) of the sheath 204 during use of the device 200. In some embodiments, an inner surface of the sheath 204 contacts or is positioned adjacent to a radially outer surface of the rail 254. In certain embodiments, at least some of the rail 254 is received in the sheath 204. For example, in some implementations, regardless of the position of the sheath 204, at least about ⅛, about ¼, about ⅓, about ½, or values in between, of the longitudinal length of the sheath 204 receives a portion of the rail 254.

In certain embodiments, the distal end 251 of the intermediate member 208 extends beyond the distal end 221 of the housing 206. For example, in some embodiments, the rail 254 extends beyond the distal end 221 of the housing 206. Such a configuration can, for example, further reduce the chance of, or generally avoid, misalignment of the sheath 204.

As illustrated in FIG. 19A, the proximal end 252 of the intermediate member 208 can include abutment members 256. As shown, the abutment members 256 can extend proximally and can be configured to engage the sleeve 216 (e.g., the partition 283), for example, to limit the distal movement of the sleeve 216 relative to the intermediate member 208. In some embodiments, the intermediate member 208 includes a plurality of first engagement members, such as resilient struts 257, which can include a radially inwardly extending portion. In certain variants, the intermediate member 208 includes a plurality of second engagement members, such as resilient arms 258. As shown, the resilient arms 258 can include a radially inwardly extending portion. As will be discussed in more detail below, the resilient struts 257 and the resilient arms 258 can be configured to engage and/or disengage with features of the piston 210.

With reference to FIG. 19C, in some embodiments, the intermediate member 208 includes a flash assembly 260 configured to signal the presence of blood, which can indicate that the needle 202 is properly placed in the patient. In some implementations, the flash assembly 260 includes a conduit 261 in fluid communication with the intermediate aperture 207 of the needle 202. Some embodiments of the conduit 261 can be disposed within one or more of the arms 255 of the intermediate member 208. In some embodiments, the conduit 261 is disposed generally perpendicular to the needle 202. In certain implementations, the conduit 261 extends radially outward from the rail 254.

In some embodiments, the flash assembly 260 includes a filter 262. In certain implementations, the filter 262 is an air pass filter, which can be configured to allow air and other gases to pass therethrough, but inhibit or prevent the passage of blood therethrough. For example, the filter 262 can include a hydrophobic material, such as polytetrafluoroethylene. In certain variants, the filter 262 is visible from on the exterior of the device 200. For example, as shown, the intermediate member 208 can include a recess or window through which the filter 262 can be observed. As will be discussed in further detail below, in some configurations, the filter 262 can be contacted by blood via the needle 202 and the conduit 261.

In some embodiments, the filter 262 is configured to change state after contacting liquid, such as blood. For example, in some cases, the filter 262 is configured to change color. In some implementations, the filter 262 changes color from white to blue. Of course, various other initial and changed color states of the filter 262 are contemplated (e.g., pink to green, black to white, orange to grey, purple to yellow, combinations thereof, or otherwise). In some embodiments, the initial color of the filter 262 is darker than the changed color of the filter 262. In other embodiments, the initial color of the filter 262 is lighter than the changed color of the filter 262. In certain implementations, the filter 262 is configured to change color in a period of less than or equal to: about 0.5 seconds, about 1 second, about 1.5 seconds, about 2 seconds, about 3 second, values in-between, or otherwise. In some embodiments, the filter 262 includes a porous material, such as Porex™ material available from the Prorex Corporation.

In certain embodiments, employing a filter 262 configured to change color can provide a more readily visible indication than, for example, viewing blood directly in a flash chamber. For example, the filter 262 can be configured to change to a color (e.g., bright blue or bright green) that can, in certain embodiments, be easier to discern than the dark magenta color that is typical for blood. Thus, in certain embodiments, the filter 262 can provide a more easily recognized indicator, which in turn can, for example, reduce the likelihood of erroneous readings (e.g., interpreting the flash chamber to indicate the presence of blood (and thus that the needle is properly placed), when in fact blood is not present).

Furthermore, a color changing filter 262 can, for example, inhibit or avoid potential undesirable reactions. Some people experience anxiety, nausea, fainting, or other reactions at the sight of blood. Thus, in conventional devices that have a flash indicator in which blood is viewed directly (e.g., through transparent or translucent portions of the device and/or windows in the device), such undesirable reactions could be provoked. However, in some embodiments, the filter 262 is at least partly opaque, thereby reducing or eliminating the sight of blood in the flash assembly 260. In certain such embodiments, the presence of blood in the flash assembly 260 is indicated indirectly (e.g., by the color change of the filter 262), not directly, thereby inhibiting or avoiding certain undesirable reactions.

In some embodiments, the portion of the flash assembly 260 that is externally visible is configured to be generally hidden from the patient during some or all of the blood collection procedure. For example, the device 200 can include a generally opaque screening member that blocks or otherwise inhibits the patient from viewing the flash assembly 260. In some embodiments, the portion of the flash assembly 260 that is externally visible is relatively small (e.g., has a diameter that is less than or equal to: about 2.0 mm, about 4.0 mm, about 6.0 mm, about 8.0 mm, about 10.0 mm, about 12.0 mm, values in between, or otherwise) compared to the distance from the penetration sight to the patient's eyes, which can reduce the ability of the patient to see the flash assembly 260. In certain implementations, the portion of the flash assembly 260 that is externally visible has a diameter that is less than the diameter of the sheath 204.

In certain embodiments, the sleeve 216 is configured to reduce or avoid the sight of blood. For example, because some vials are transparent, some or all of the sleeve 216 can be least partly opaque. Further, certain variants of the sleeve 216 have sufficient length to receive some or all of the length of the vial. For example, certain embodiments of the sleeve 216 have a length parallel to the axis L of at least about 60 mm, about 65 mm, about 70 mm, about 75 mm, about 80 mm, about 85 mm, about 90 mm, about 100 mm, about 105 mm, values in between, or otherwise. Some variants of the sleeve 216 have sufficient length to receive at least about 75% of the axial length of the vial. In certain embodiments, the sleeve 216 has a window (not shown) configured to permit person using the device 200 to view the amount of blood in the vial (e.g., to discern when to remove the vial from the device 200). In some such embodiments, the window is disposed so as to inhibit the ability of the patient to view blood in the vial through the window. For example, in certain variants, when the sleeve 216 is attached with the intermediate member 208, the window is generally not aligned with the indication face 226 of the housing 206. Such a configuration can reduce the chance of the patient seeing though the window in those embodiments in which the indication face 226 is faced toward the patient during the blood collection procedure.

Some embodiments of the device 200 include other flash detection structures and methods. For example, some embodiments are configured to allow air or other gases within the needle 202 to escape into the ambient environment by passing between the needle 202 and the boot 214. Such evacuation of air in the needle 202 can, for example, facilitate blood from a vessel flowing into the needle 202 (e.g., by the pressure in the vessel). Certain embodiments of the device 200 are configured to allow the visual detection of such blood. For example, the needle 202 can include distinct and spaced-apart needle portions in fluid communication. Further, at least some of the device 200 can be transparent or translucent, which can allow visual detection of blood between the needle portions or in other portions of the device (e.g., a viewing window).

Some embodiments also include a porous vent (not shown). The vent can be configured to permit the passage of air therethrough, yet prevent or inhibit the passage of blood therethrough. For example, the vent can comprise a hydrophobic material, such as polytetrafluoroethylene. In certain variants, the vent is disposed at or near a distal end of the boot 214. Further details regarding some example embodiments of flash detection structures and methods that can be used with the devices disclosed herein are provided in U.S. Pat. Nos. 7,160,267; 7,226,432; 7,396,343; and 7,530,967; each filed May 3, 2004, each of which is incorporated herein by reference in its entirety.

Figure 20:
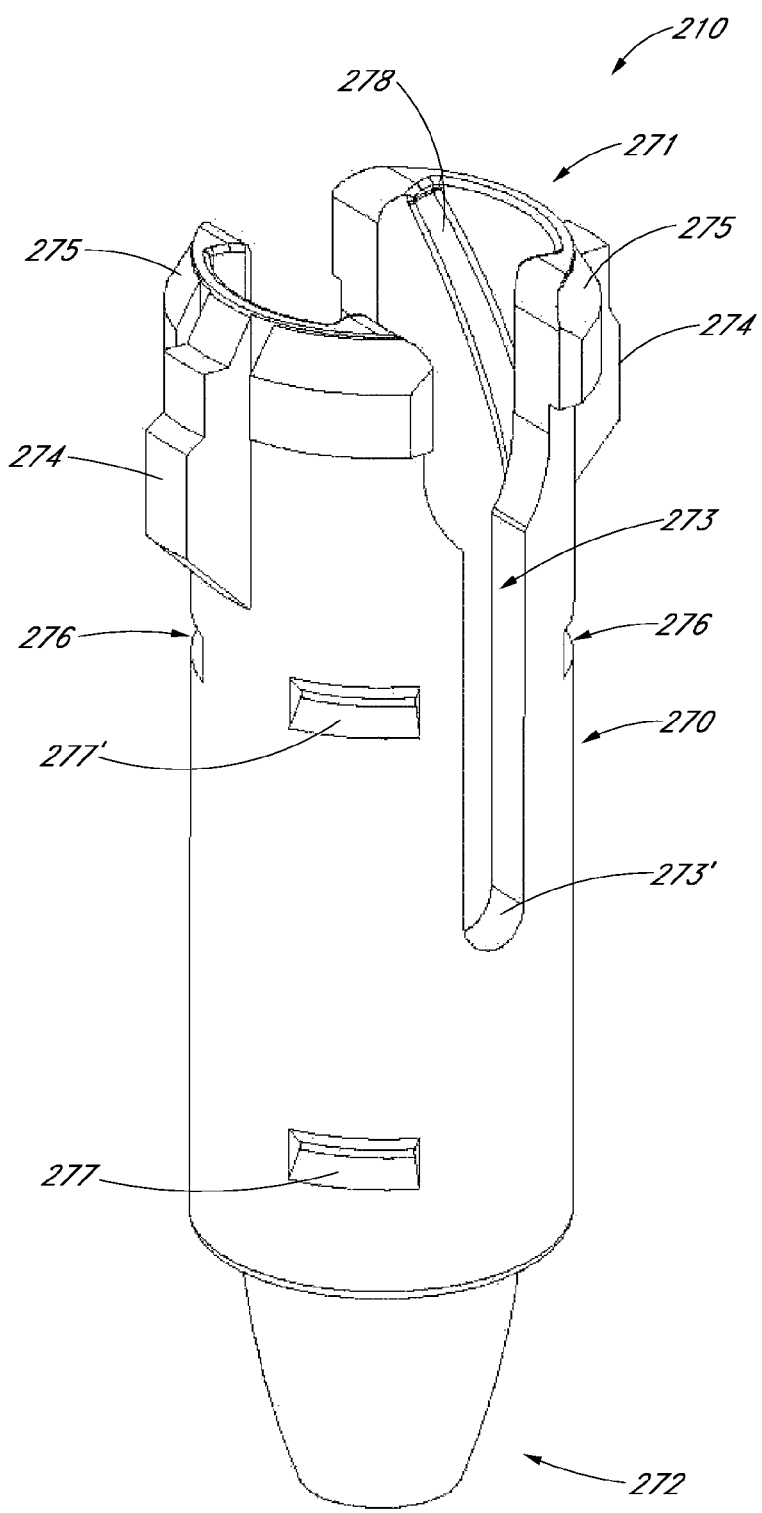
FIG. 20 illustrates a perspective view of an embodiment of the piston of the device of FIG. 15.
Figure 20A:
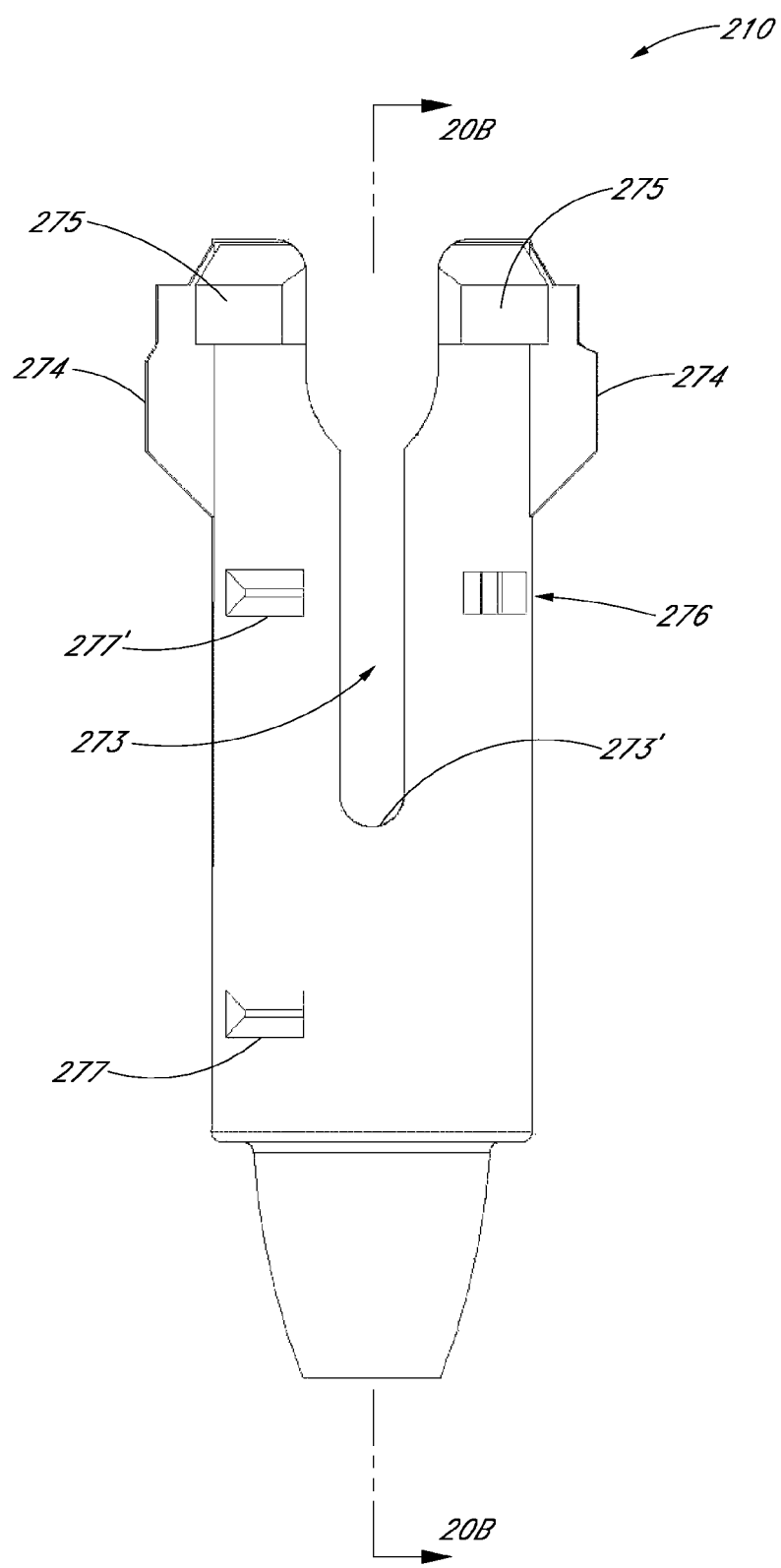
FIG. 20A illustrates a front view of the piston of FIG. 20.
Figure 20B:
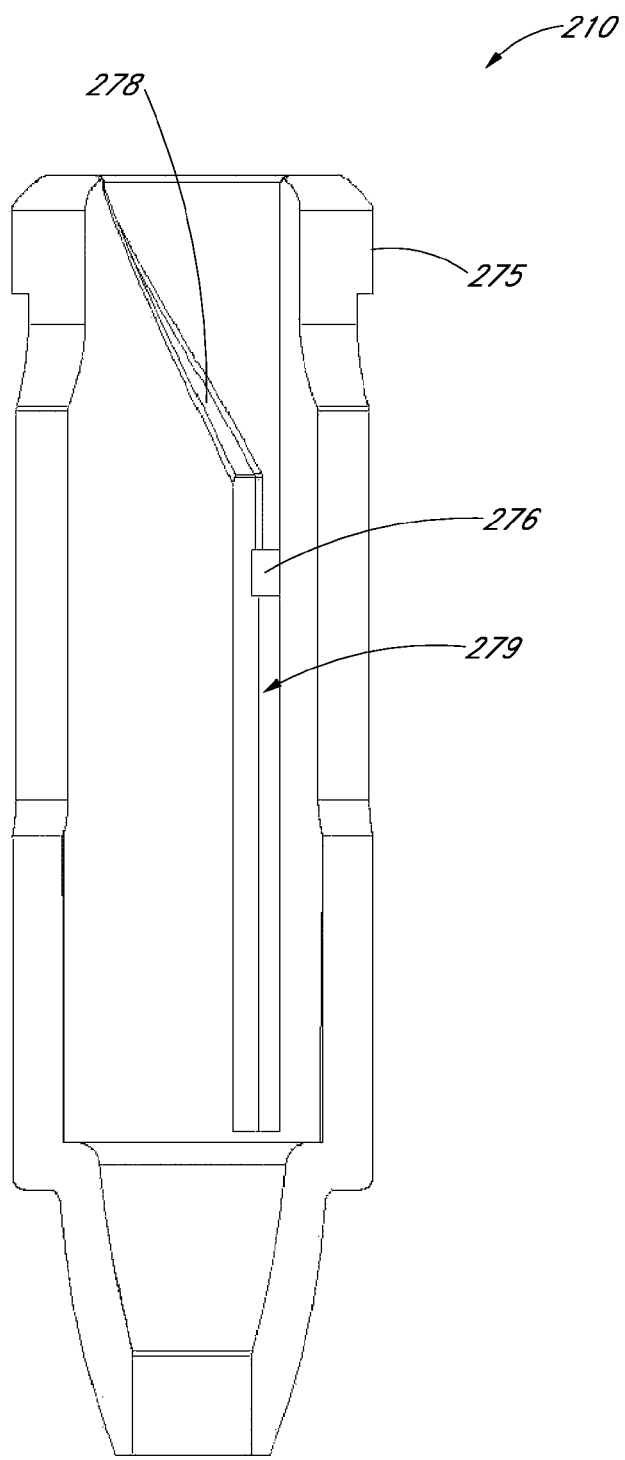
FIG. 20B illustrates a cross-sectional view along the line 20B-20B of FIG. 20A.

With reference to FIGS. 20-20B, an embodiment of the piston 210 is illustrated. Certain embodiments of the piston 210 include a hollow tube 270, a distal end 271, and a proximal end 272. In some variants, the proximal end 272 has a generally rounded shape and/or has a smaller diameter than the hollow tube 270. Such a configuration can, for example, assist in mating with the blood collection vial (e.g., can facilitate a substantially air-tight seal between the proximal end 272 and the vial). In some embodiments, the proximal end 272 is generally flat. Certain implementations of the piston 210 are configured to receive at least some of the proximal end 242 of the sheath 204. For example, an inside diameter of the hollow tube 270 can be greater than the outside diameter of the sheath 204.

In some embodiments, the piston 210 includes one or more guiding structures, such as channels 273 that extend longitudinally and terminate in stops 273'. Some variants have channels 273 with an increased width at the distal end 271, which can, e.g., facilitate assembly. In certain embodiments, the distal end 271 of the piston 210 includes one or more engagement structures, such as protrusions 274 and/or flanges 275. As illustrated, certain variants of the protrusions 274 and/or flanges 275 extend radially outward from the hollow tube 270. Some embodiments include one or more windows 276. In certain embodiments, the windows 276 are recesses in the hollow tube 270. In other implementations, the windows 276 fully extend through the width of the hollow tube 270.

In certain implementations, the piston 210 includes one or more engagement structures, such as notches 277 (e.g., wedge-shaped recesses), at or near the proximal end 272. In certain variants, the piston 210 includes one or more notches 277' positioned distal of the notches 277. The notches 277, 277' can be generally circumferentially aligned (e.g., such that the notches 277, 277' are generally collinear on a line generally parallel with the axis L). The notches 277, 277' can be configured to engage one or more features of the housing 206 or intermediate member 208 to inhibit unintentional proximal movement of the piston 210.

In some embodiments, the piston 210 includes a plurality of tracks. For example, the piston 210 can include a ramp track 278 and a longitudinal track 279. In certain implementations, the longitudinal track 279 extends generally parallel with the axis L. In some embodiments, the ramp track 278 has a non-longitudinal orientation, such as an angle, helix, spiral, curve, or other shape relative to the axis L. As will be discussed in greater detail below, in certain embodiments, the tracks 278, 279 can be configured to engage the foot 245 of the sheath 204, which can encourage rotation of the sheath 204 relative to the piston 210, which in turn can facilitate distal movement of the sheath 204.

Figure 21:
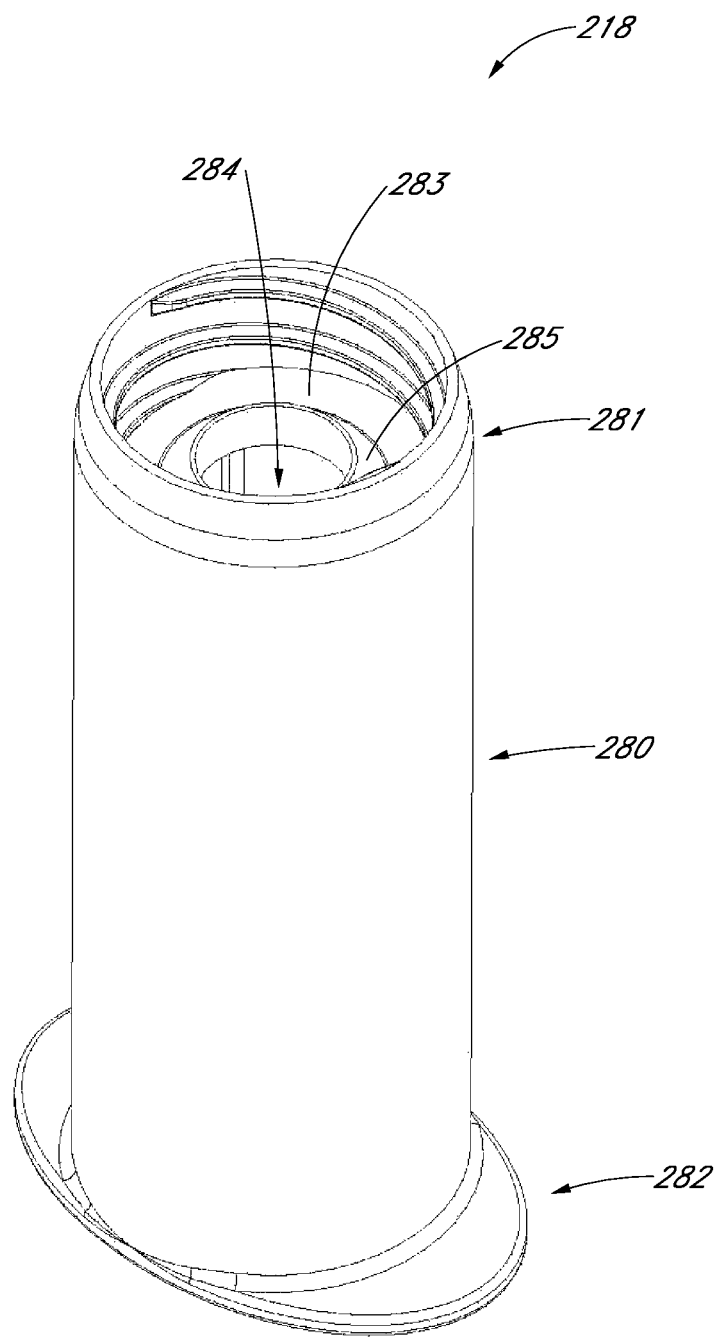
FIG. 21 illustrates a perspective view of an embodiment of the sleeve of the device of FIG. 15B.
Figure 21A:
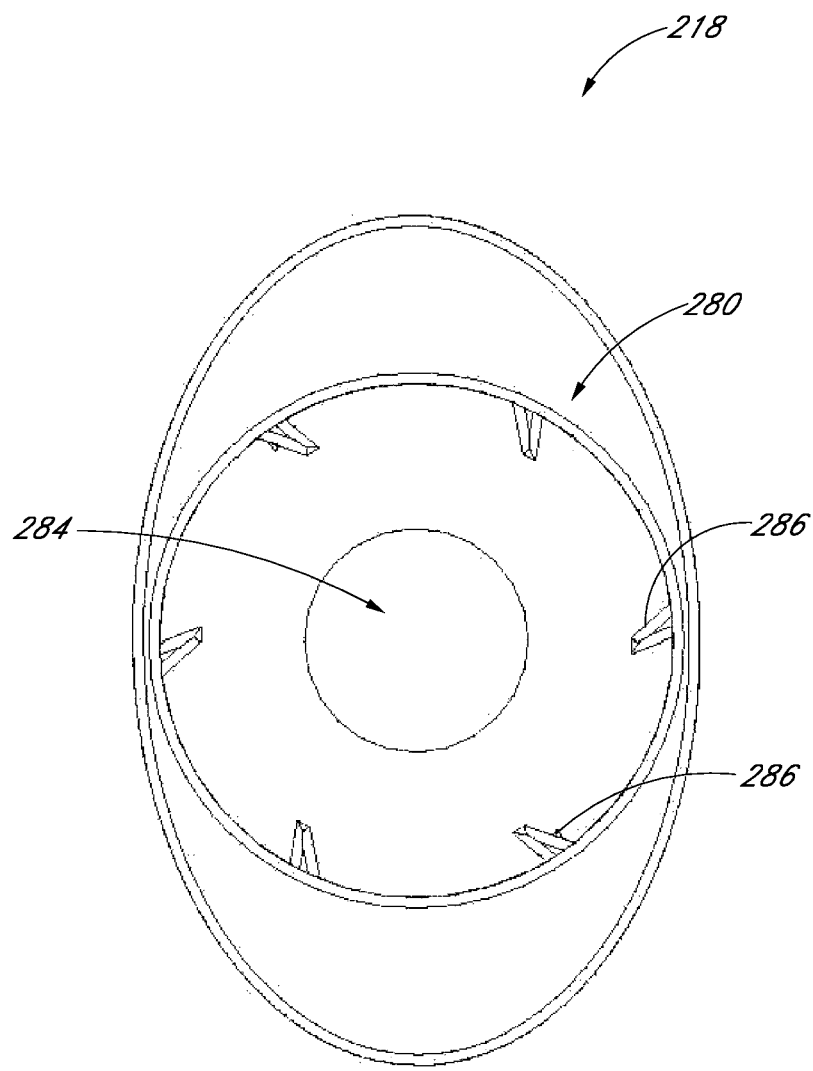
FIG. 21A illustrates a bottom view of the sleeve of FIG. 21.

With regard to FIGS. 21 and 21A, an embodiment of the sleeve 216 is illustrated. In some embodiments, the sleeve 216 includes a hollow member 280, a distal ends 281, and a proximal end 282. In some embodiments, the sleeve 216 is configured to couple with the intermediate member 208. For example, the distal ends 281 can have threads configured to engage threads on the intermediate member 208. In certain implementations, the sleeve 216 has a partition 283 with an opening 284 configured to receive the proximal end 272 of the piston 210. In certain embodiments, the sleeve 216 includes a tapered coupling member, such as a wedge 285. For example, the wedge 285 can be coupled with the wall 283 and be near or adjacent the opening 284.

In some variants, the sleeve 216 includes retaining members, such as fingers 286, which can project radially inwardly. In certain embodiments, the fingers 286 project inward to a greater extent near the distal end 281 than near the proximal end 282. The fingers 286 can, for example, provide a friction fit with a blood collection tube, thereby inhibiting or preventing the tube from being pushed proximally by the bias of the biasing member 212.

Figure 22:
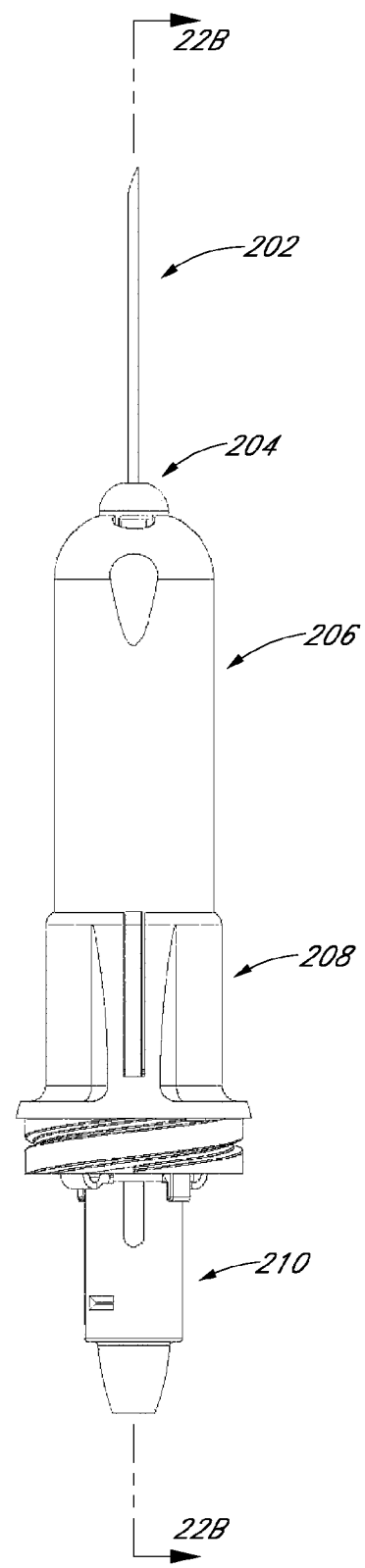
FIG. 22 illustrates a front view of the device of FIG. 15 in an initial state.
Figure 22A:
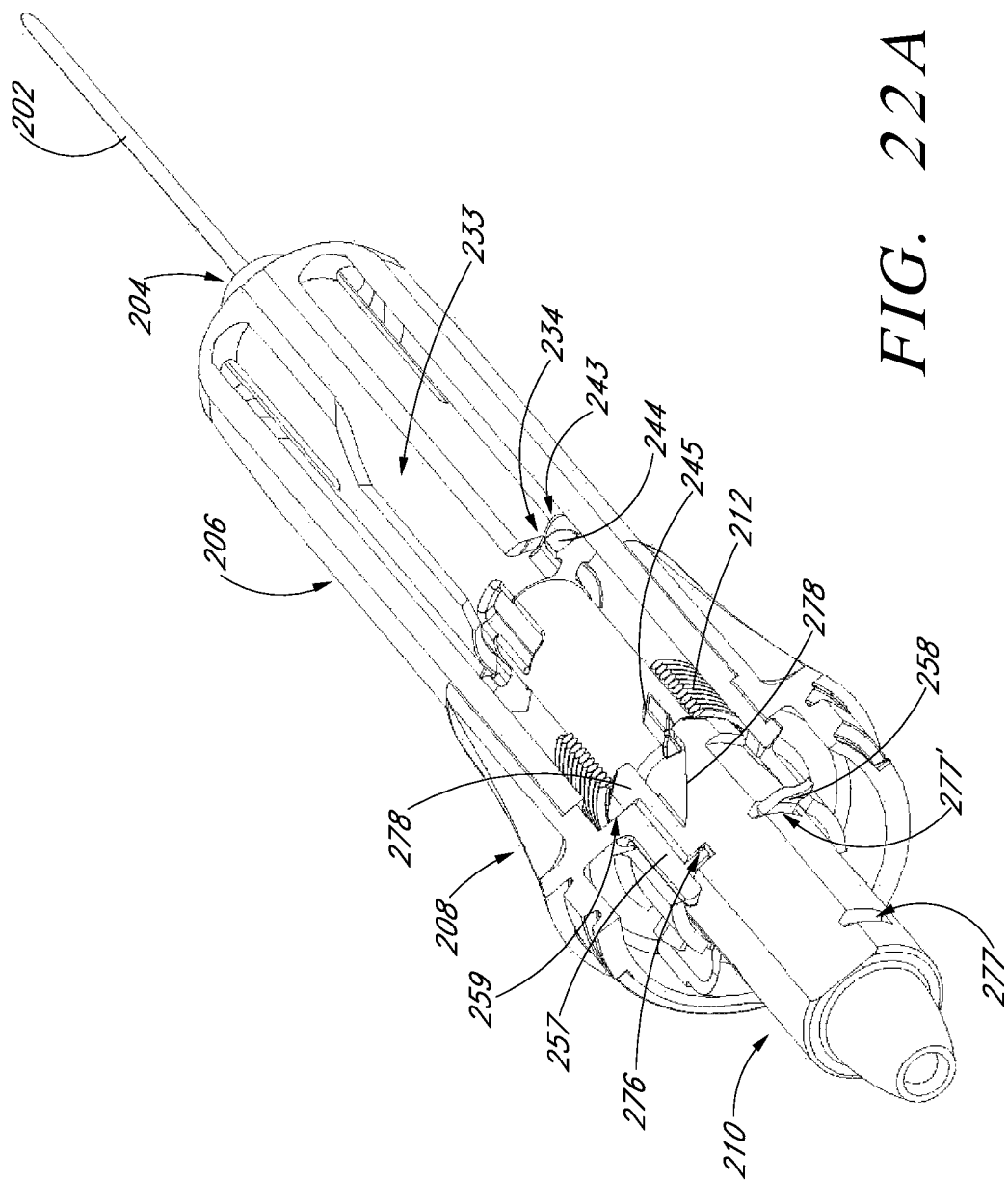
FIG. 22A illustrates a rear perspective partial cross-sectional view of the device of FIG. 22.
Figure 22B:
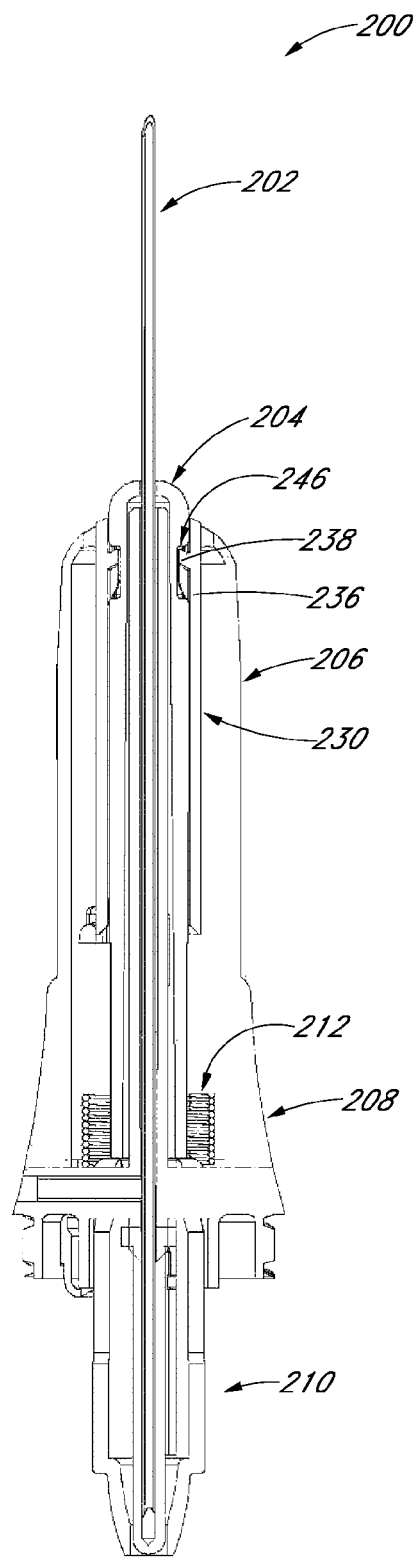
FIG. 22B illustrates a cross-sectional view along the line 22B-22B of FIG. 22.

With reference to FIGS. 22-22B, the device 200 in an initial state is illustrated. In certain embodiments, in the initial state, the sleeve 216 is separate from the rest of the device 200. For example, in some embodiments, in the initial state, the sleeve 216 is not secured to the intermediate member 208. Such a configuration can, for example, provide an arrangement in which the device 200 can be stored or shipped. In some embodiments, the device 200 is stored or shipped in a configuration that includes the cap 218, as shown in FIG. 15A.

In some embodiments, the prongs 227 of the housing 206 are received in the slot 253 of the intermediate member 208. In certain implementations, the radially outer face of the prongs 227 is generally flush with the radially outer face of the intermediate member 208, thereby providing a generally seamless aesthetic. Moreover, the tabs 228 of the housing 206 can be configured to engage (e.g., by a snap connection with the clasps 229) the shoulder 259 of the intermediate member 208, thereby substantially permanently coupling the housing 206 and the intermediate member 208. Thus, in certain embodiments, the housing 206 and intermediate member 208 are substantially stationary relative to each other. Such a configuration can, for example, provide a stable location on the device 200 for a person to use as a handhold (e.g., when transporting the device 200, during the blood collection procedure, and/or in the course of disposal). In some embodiments, the recess 220' on the inner wall of the body 220 of the housing 206 can receive a portion of the protrusion 274 of the piston 210.

In certain embodiments, in the initial state, the sheath 204 is generally inhibited from moving, thereby inhibiting or preventing unintentional activation of certain features configured to promote single-use of the device 200. For example, in some embodiments, in the initial state, the wings 243 of the sheath 204 can abut the valley 234 of the frame 230 of the housing 208, thereby inhibiting distal movement of the sheath 204. In certain implementations, the engagement of the wings 243 and the valley 234 counteracts the biasing member 212, which biases the sheath 204 distally.

In some embodiments, in the initial state, the tooth 238 of the housing 206 is received in the distal opening 246 of the sheath 204 (see FIG. 22B). In some embodiments, the tooth 238 is configured to resist proximal movement of the sheath 204. For example, the tooth 238 can be angled proximally. In certain variants, a distal end of the distal opening 246 has a complementary shape with regard to the tooth 238. For example, both the tooth 238 and the distal opening 246 can be angled proximally.

In certain implementations, the piston 210 is engaged with the intermediate member 208. For example, the protrusion 274 of the piston 210 can be at least partly received in one of the spaces 259' of the intermediate member 208. In some arrangements, one or more of the flanges 275 of the piston 210 abuts the shoulder 259 of the intermediate member 208. Thus, the piston 210 can be retained in the intermediate member 208 although the biasing member 212 biases the piston 210 proximally.

In some variants, the channel 273 of the piston 210 receives the arms 255 of the intermediate member 208. In some such variants, distal movement of the piston 210 is limited by the longitudinal length of the channels 273. For example, in some embodiments, the arms 255 abut with the stops 273' after having traveled the longitudinal extent of the channel 273, thereby inhibiting further distal movement of the piston 210.

In certain embodiments, in the initial state, a portion of the piston 210 extends proximally of the proximal end 205 of the needle 202. Typically, in the initial state, the piston 210 is inhibited or prevented from moving distally. Such a configuration can, for example, reduce the likelihood of the distal end 205 of the needle 202 becoming contaminated or pricking a person. In other states, as will be discussed below, the piston 210 is configured to move distally (e.g., by a distal force applied via the blood collection vial) and/or proximally (e.g., by the bias of the biasing member 212).

As illustrated in FIG. 22A, in some embodiments, in the initial state, the struts 257 of the intermediate member 208 engage with the windows 276 of the piston 210, thereby providing a radial interference and inhibiting the piston 210 from moving distally. Indeed, the struts 257 and/or the windows 276 can be shaped or otherwise configured such that even if a distal force is applied to the piston 210, the struts 257 and the windows 276 remain engaged. In certain embodiments, in the initial state, the resilient arms 258 of the intermediate member 208 engage the distal notches 277' of the piston 210, thereby providing a secondary radial interference to resist movement.

Typically, the needle 202 is coupled with another component of the device 200. In some implementations, the needle 202 is mounted to the rail 254. For example, the needle 202 can be joined or bonded with the rail 254 with an adhesive, by welding (e.g., thermal or ultrasonic), or otherwise. As shown, the needle 202 can be received at least partly within the rail 254. In some variants, the rail 254 is at least partly received within the sheath 204. In some embodiments, the sheath 204 is at least partly radially received in the housing 206. In certain implementations, the housing 206 is at least partly received within the intermediate member 208. In some embodiments, the distal end 203 of the needle 202 projects distally from the sheath 204 and the proximal end 205 of the needle 202 projects distally from the intermediate member 208.

In certain implementations, the proximal end of the rail 254 is configured to couple with the resilient boot 214. The proximal end of the rail 254 can have retaining features (e.g., ribs or radially outwardly extending shoulders) upon which the boot 214 can be retained, such as by friction fit. As shown, the boot 214 can receive the proximal end 205 of the needle 202. The boot 214 can be configured to be pierced by the proximal end 205 of the needle 202. Further, some variants of the boot 214 are configured to substantially reseal upon removal of the proximal end 205 of the needle 202 from the boot 214.

As noted above, some embodiments of the device 200 include the biasing member 212. In certain implementations, the biasing member 212 engages and extends between the sheath 204 and the piston 210. In some embodiments, the biasing member 212 is positioned longitudinally between the sheath 204 and the piston 210. In certain embodiments, the biasing member 212 encourages the sheath 204 distally and/or the piston 210 proximally. In certain implementations, the biasing member 212 encourages the sheath 204 and the piston 210 apart. For example, the biasing member 212 can encourage the sheath 204 and the piston 210 in generally opposite directions. In some embodiments, the biasing member 212 engages the wings 243. In some embodiments, the biasing member 212 engages one or more of the flanges 275 of the piston 210.

As illustrated, some embodiments include a single biasing member 212. Other embodiments include a plurality of biasing members. For example, some embodiments include a first biasing member configured to bias the sheath 204 and a second biasing member configured to bias the piston 210. Such a configuration can, for example, reduce or avoid a change in the bias on the sheath 204 when the piston 210 moves, or vice versa. In certain variants, the first and second biasing members are at least partly radially nested.

Various biasing members 212 can be used, such as a helical spring, conical spring, wave-spring, belleville washers, or otherwise. In some embodiments, the biasing member 212 is a conical coil spring having a free length of about 100 mm and a spring rate of at least about 0.12 N/mm through the linear portion of the spring's deflection. Other constructions can include softer or stiffer springs depending on the application, and can be constructed of substantially any suitable material. Progressive springs and/or multiple springs of varying lengths can also be used, for example, to provide a variable effective spring rate.

Figure 23:
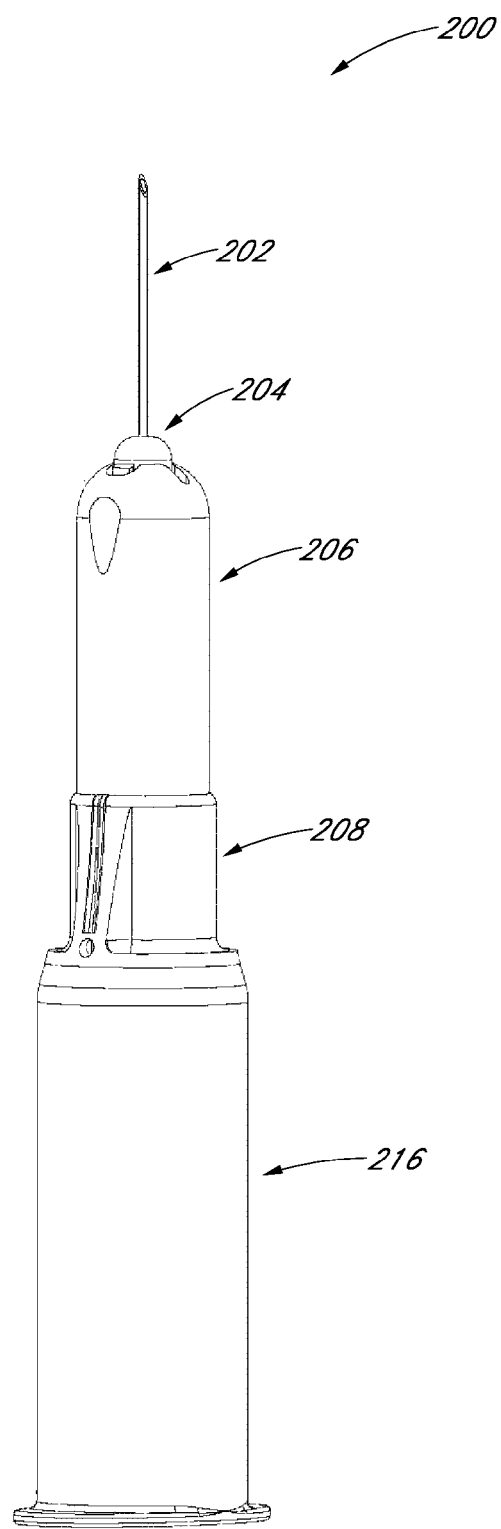
FIG. 23 illustrates a front view of the device of FIG. 15 in a ready-to-operate state.
Figure 23A:
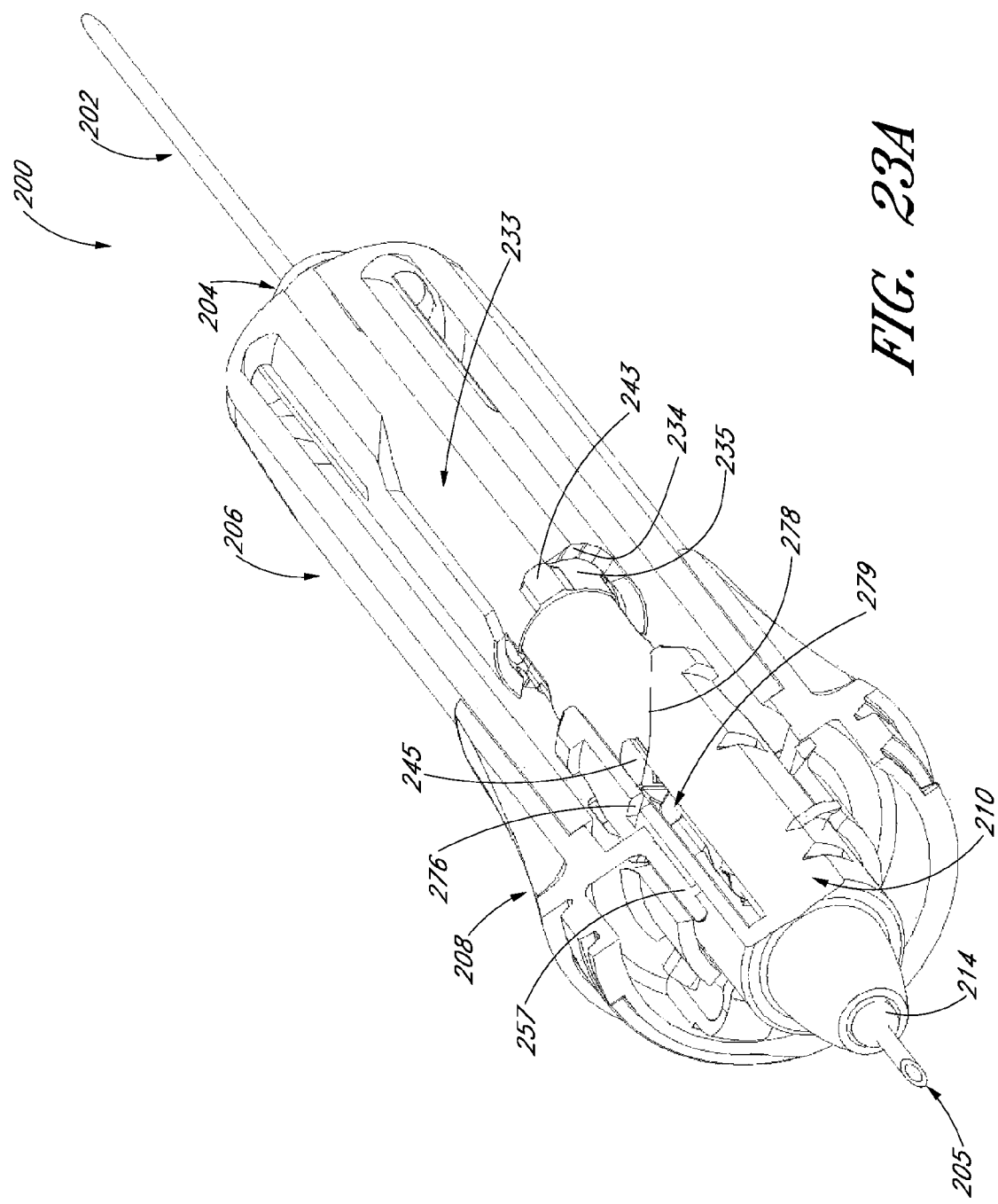
FIG. 23A illustrates a rear perspective partial cross-sectional view of the device of FIG. 23, with the sleeve and biasing member not illustrated for clarity.
Figure 23B:
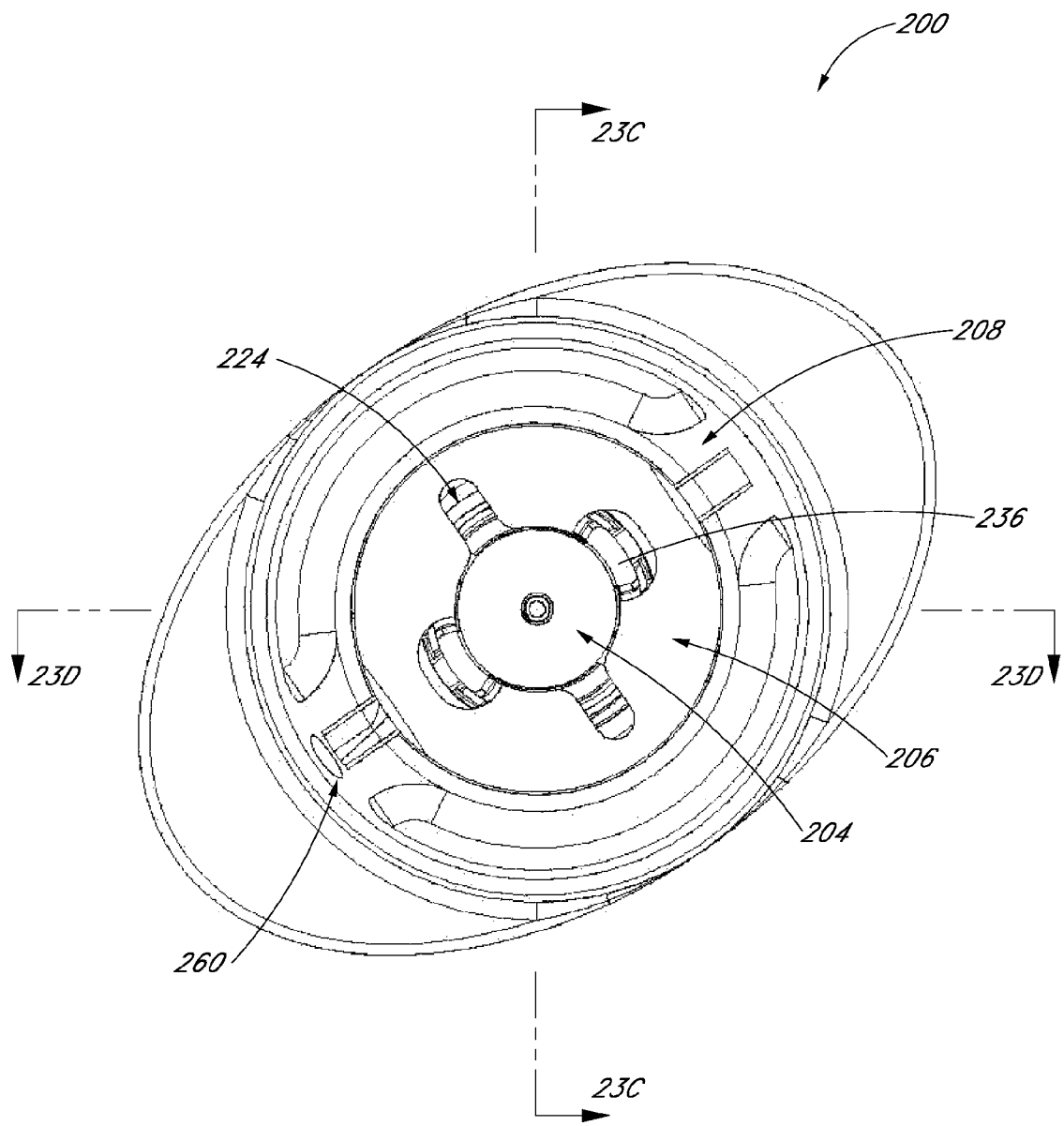
FIG. 23B illustrates a top view of the device of FIG. 23.
Figure 23C:
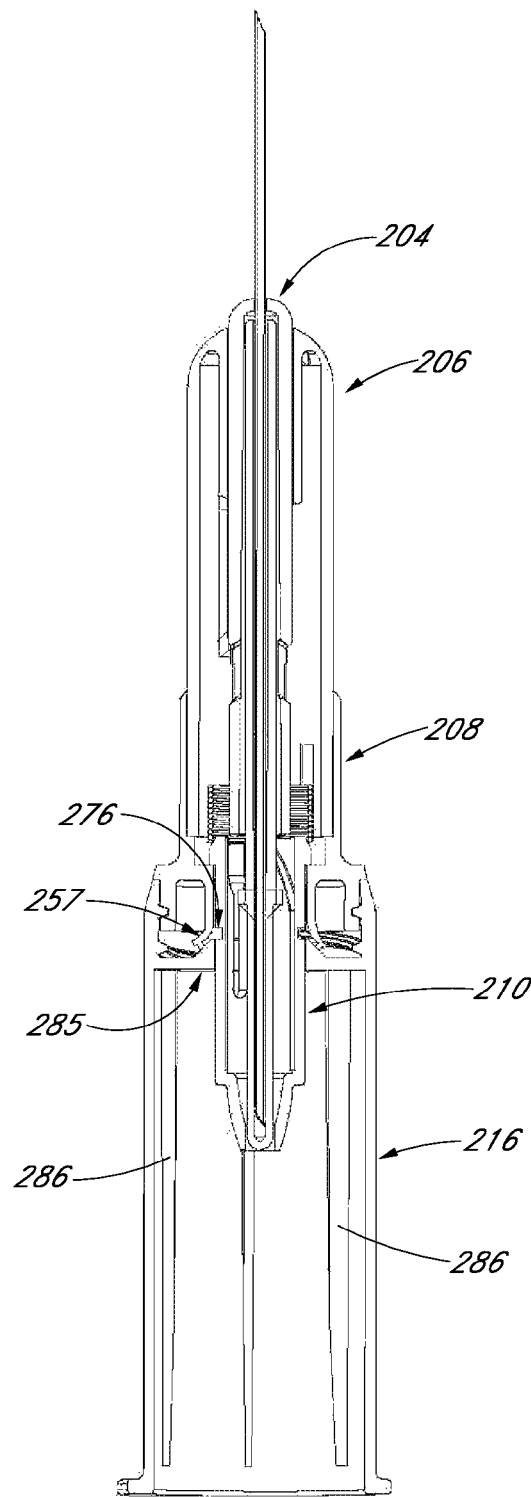
FIG. 23C illustrates a cross-sectional view along the line 23C-23C of FIG. 23A.
Figure 23D:
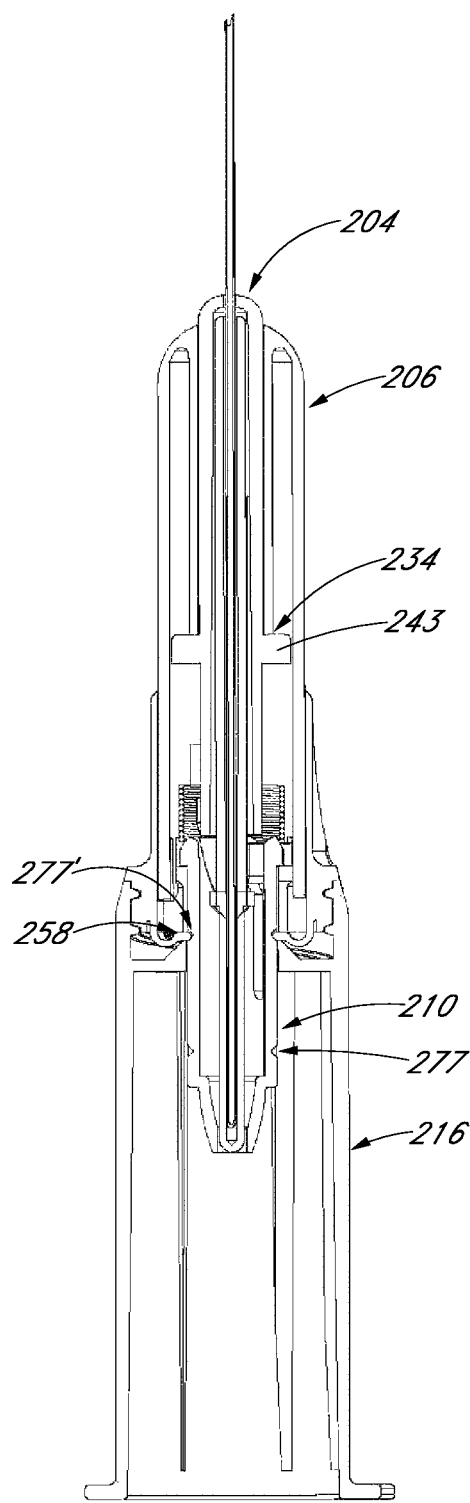
FIG. 23D illustrates a cross-sectional view along the line 23D-23D of FIG. 23A.

With reference to FIGS. 23-23D, the device 200 is illustrated with the sleeve 216 attached. As previously noted, in certain embodiments, in the initial state, the sleeve 216 is separated from the rest of the device 200. However, the sleeve 216 is normally attached prior to a blood collection procedure being performed. As illustrated, in certain implementations, the sleeve 216 is attached by securing it to the intermediate member 208, such as with a threaded connection. In some embodiments, attachment of the sleeve 216 releases the piston 210, thereby placing the device 200 in a ready-to-operate state. Typically, the device 200 is placed into the ready-to-operate state at about the time and/or location in which the device is to be used (e.g., at the bedside, phlebotomy chair, or otherwise).

In some embodiments, the sleeve 216 is configured to couple with the intermediate member 208 (e.g., via a threaded connection). In some variants, such coupling can engage the wedge 285 of the sleeve 216 with the struts 257 of the intermediate member 208. For example, the wedge 285 can deflect the struts 257 radially outward. In some embodiments, the struts 257 are deflected such that they no longer engage the windows 276 of the piston 210, thereby removing the radial interference between the struts 257 and the windows 276. In certain implementations, the opening 284 in the sleeve 216 can receive a portion of the piston 210.

Generally, during a blood collection procedure, after removing the cap 218 (if used) and taking surface prepatory steps (if appropriate, e.g., applying a disinfectant to the surface), the distal end 203 of the needle 202 can be placed against the patient's skin at the penetration site. The device 200 can then be moved distally, thereby moving the distal end 203 of the needle 202 into the patient (e.g., through the patient's skin and into a vein).

In certain embodiments, the device 200 is configured to facilitate a shallow insertion angle (e.g., less than or equal to about 30° relative to the surface being penetrated) of the needle 202. A shallow angle of insertion can facilitate proper placement of the needle 202 and/or reduce discomfort associated with placement of the needle 202. In some embodiments, the sheath 204 includes a relatively small diameter, which can reduce radial interference between the sheath 204 and the surface being penetrated, and thus facilitate the shallow insertion angle. For example, the sheath 204 can have an outside diameter of at least about 3.0 mm and/or less than or equal to about 12.5 mm. In certain implementations, the outside diameter of the sheath 204 is about 2.0 mm, about 3.0 mm, about 4.0 mm, about 5.0 mm, about 6.0 mm, about 7.0 mm, about 8.0 mm, about 9.0 mm, about 10.0 mm, values in between, or otherwise. As illustrated, the outside diameter of the sheath 204 can be less than an outside diameter of the housing 206.

In some embodiments, blood in the vein can be encouraged (e.g., by pressure in the vein) proximally through the needle 202. In certain embodiments, the blood can pass through the intermediate aperture 207 of the needle 202 and into the conduit 261 of the flash assembly 260. As noted above, the filter 262 can be an air-pass filter, thereby permitting air or other gases in the needle 202 and/or conduit 261 to escape. Thus, some embodiments of the device 200 are configured to inhibit air or other gases in the needle 202 and/or conduit 261 from presenting an embolus that inhibits blood from contacting the filter 262. As also noted above, the filter 262 can be visible on the exterior of the device 200 and can be configured to exhibit a change (e.g., a color change) after being contacted with blood. Accordingly, certain embodiments can provide the user of the device 200 a visual indication of the blood having passed through the needle 202 and conduit 261, which can indicate, for example, that the needle 202 is properly placed in the patient. Further, in certain embodiments, such an indication is made without visually exposing the blood itself.

Figure 24:
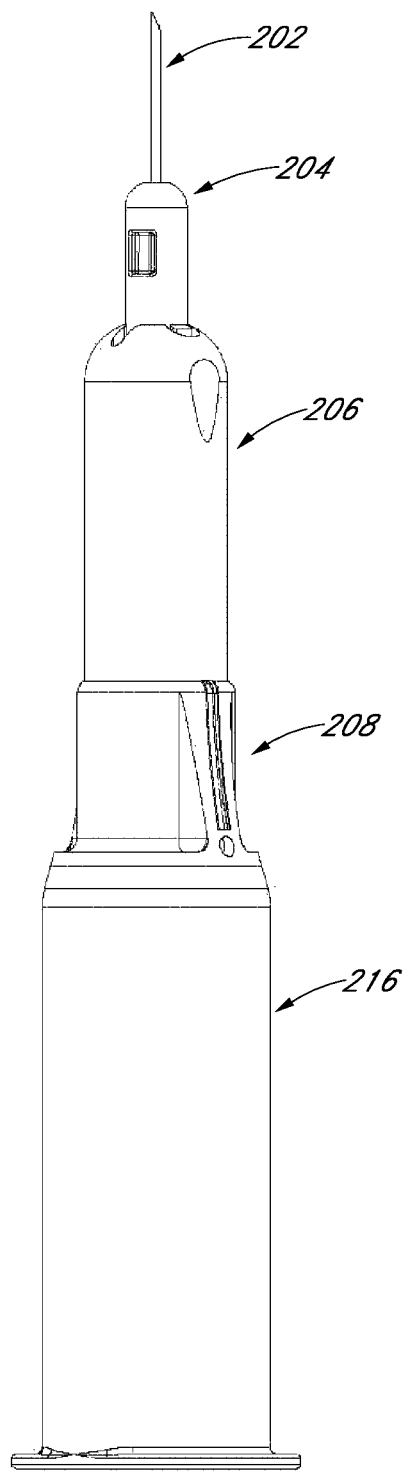
FIG. 24 illustrates a front view of the device of FIG. 15 in an intermediate state, with the sleeve and biasing member not illustrated for clarity.
Figure 24A:
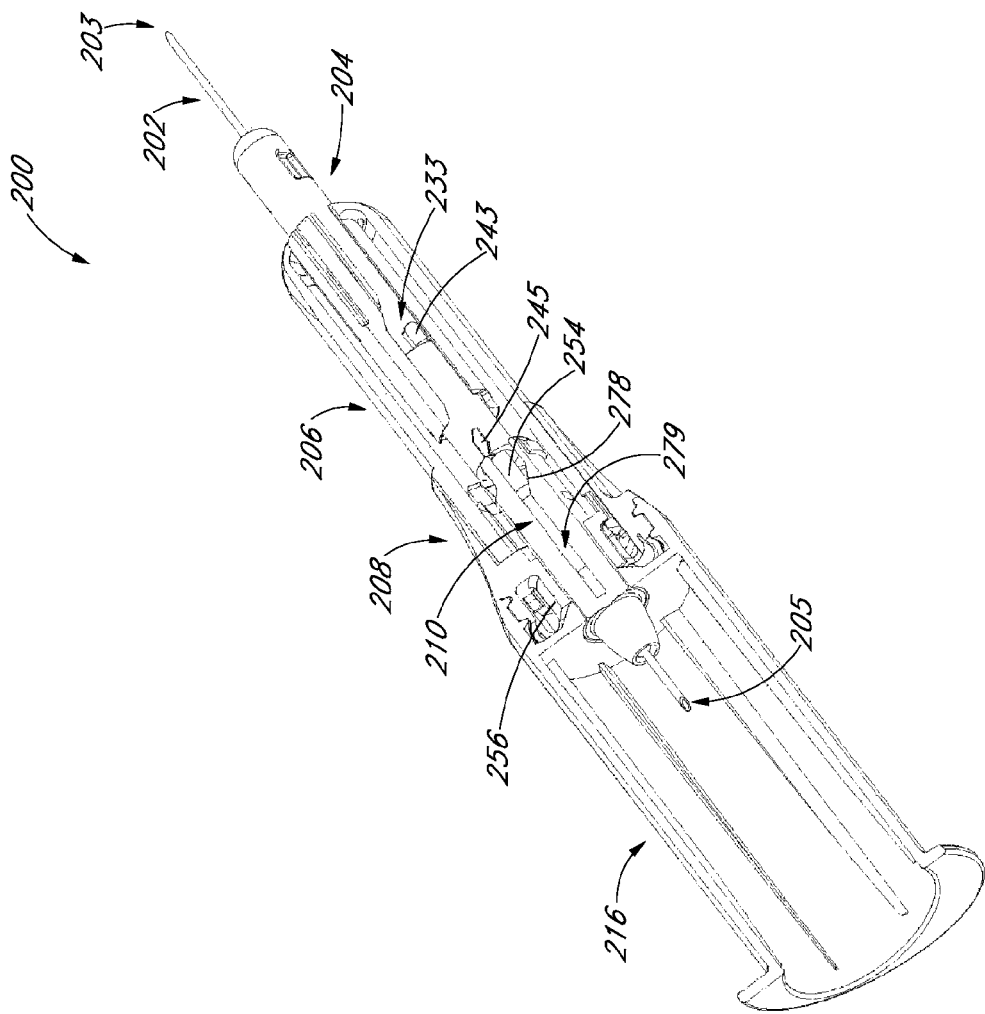
FIG. 24A illustrates a rear perspective partial cross-sectional view of the device of FIG. 24.
Figure 24B:
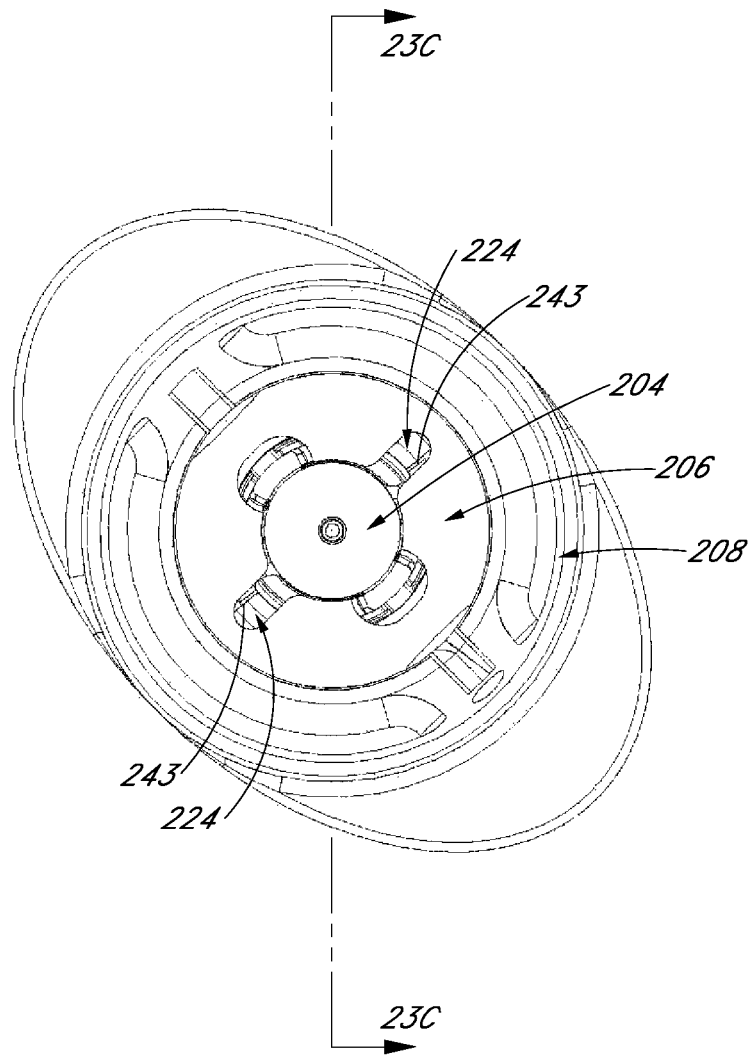
FIG. 24B illustrates a top view of the device of FIG. 24.
Figure 24C:
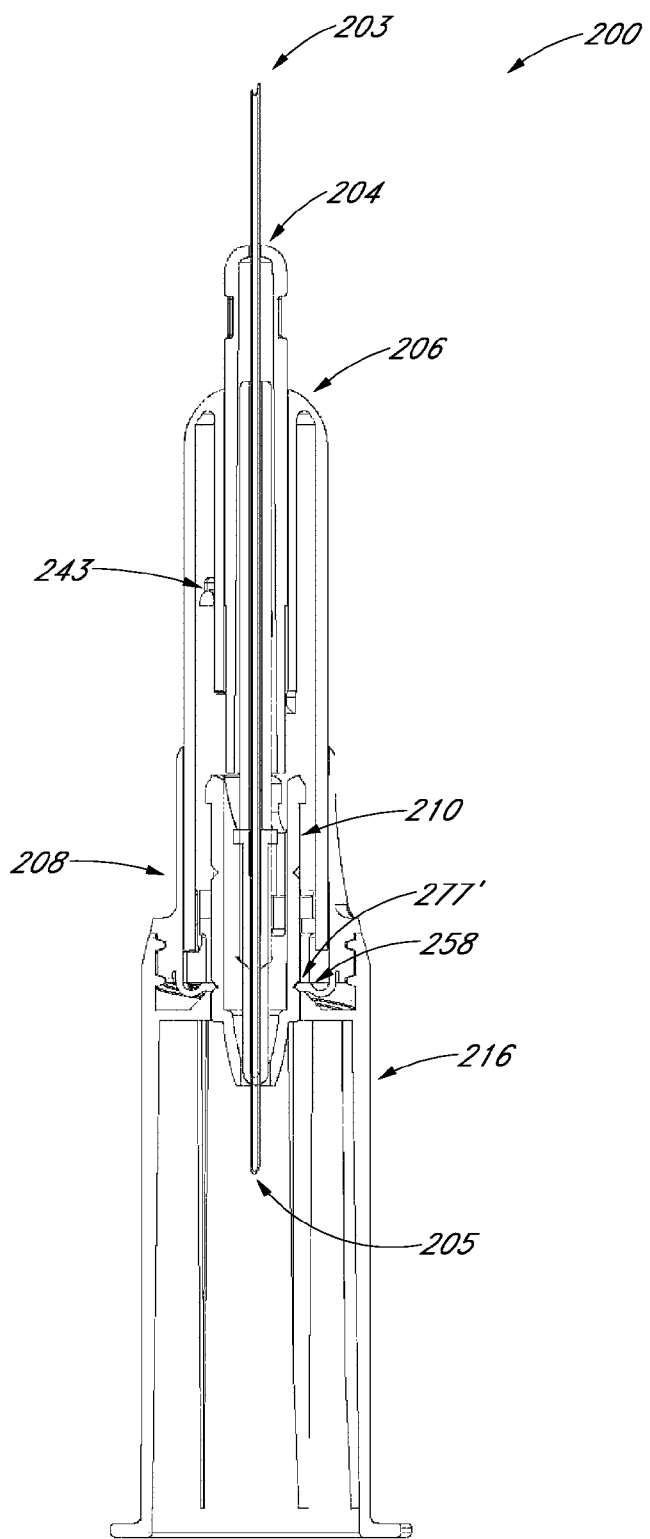
FIG. 24C illustrates a cross-sectional view along the line 24C-24C of FIG. 24B.

When proper placement of the needle 202 in the patient has been determined, the blood collection portion of the procedure generally begins. As illustrated in FIGS. 24-24B, during the blood collection portion of the procedure, a distal end of the blood collection vial can be abutted with the proximal end 272 of the piston 210. In some instances, the user applies distal force to the blood collection vial, which in turn applies distal force to the piston 210 against the bias of the biasing member 212. The distal force on the piston 210, if sufficiently large, can overcome the bias of the biasing member 212. Further, sufficient distal force on the piston 210 can result in the resilient arms 258 of the intermediate member 208 being disengaged (e.g., being deflected radially outward) from the distal notch 277' of the piston 210. Accordingly, the piston 210 can be moved distally relative to the needle 202.

In some embodiments, distal movement of the piston 210 results in the boot 214 being pressed against the blood collection vial. Continued distal force can result in the proximal end 205 of the needle 202 piercing the boot 214 and passing into the blood collection vial. Thus, blood can flow from the patient's vein into the blood collection vial via the needle 202. In some embodiments, the flow of blood is encouraged by the blood collection vial being evacuated (e.g., under a vacuum).

In certain embodiments, as the blood collection vial moves the piston 210 distally, the piston 210 moves relative to the sheath 204. In some embodiments, the ramp track 278 of the piston 210 engages the foot 245 of the sheath 204. For example, the foot 245 can slide along the ramp track 278, which can be non-axially oriented (e.g., angled, helixed, spiraled, curved, or otherwise shaped with regard to the axis L). As the foot 245 slides along the ramp track 278, a torque can be created. In some implementations, because the channel 273 of the piston 210 is engaged with the arms 255 of the intermediate member 208, the piston 210 is inhibited from being rotated relative to the intermediate member 208 by the torque.

In some embodiments, the sheath 204 can be rotated relative to the housing 206, intermediate member 208, and/or piston 210 by the torque. For example, in the illustrated embodiment, distal movement of the piston 210 can encourage the foot 245 to ride along the helical ramp track 278, thereby rotating the sheath 204 relative to the intermediate member 208. In certain variants, the sheath 204 is configured to rotate about the longitudinal axis at least about 10° and/or less than or equal to about 120°. In some embodiments, the sheath 204 is configured to rotate at least about 30° and/or less than or equal to about 60°. In some implementations, the sheath 204 is configured to rotate at least about 15°, about 20°, about 25°, about 30°, about 35°, about 40°, about 45°, about 50°, about 55°, about 60°, about 65°, about 70°, about 75°, about 80°, about 85°, about 90°, values in between, or otherwise. In certain variants, with sufficient distal movement of the piston 210, the foot 245 moves into the longitudinal track 279.

In some embodiments, rotation of the sheath 204 results in the distal openings 246 of the sheath 204 being rotated out of engagement with the tooth 238 of the housing 206. For example, the tooth 238 can be deflected radially outward by the hollow casing 240 of the sheath 204.

Figure 25:
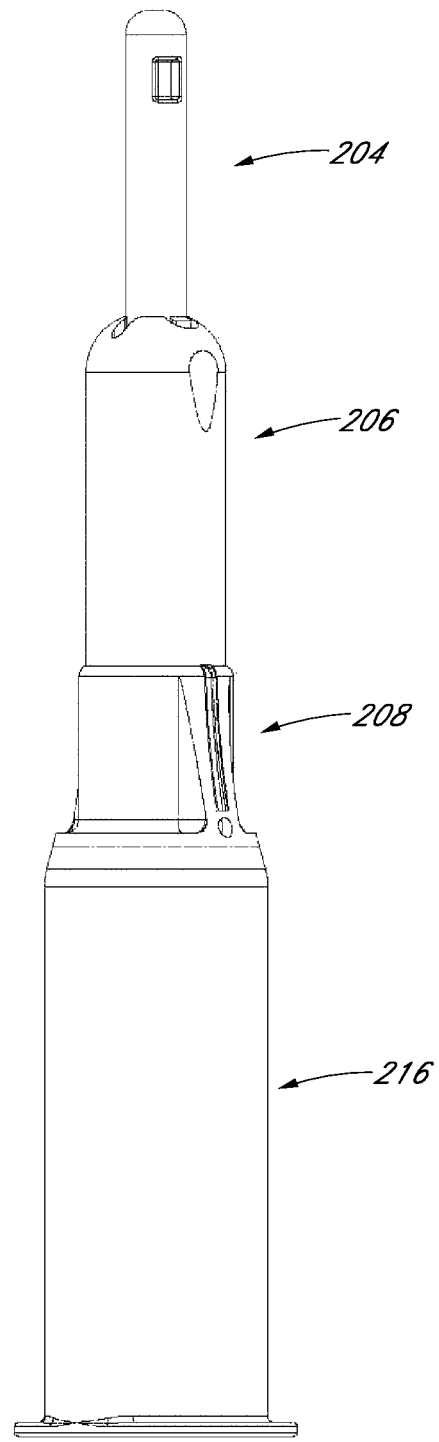
FIG. 25 illustrates a front view of the device of FIG. 15 with the sheath in a distal and locked position.
Figure 25A:
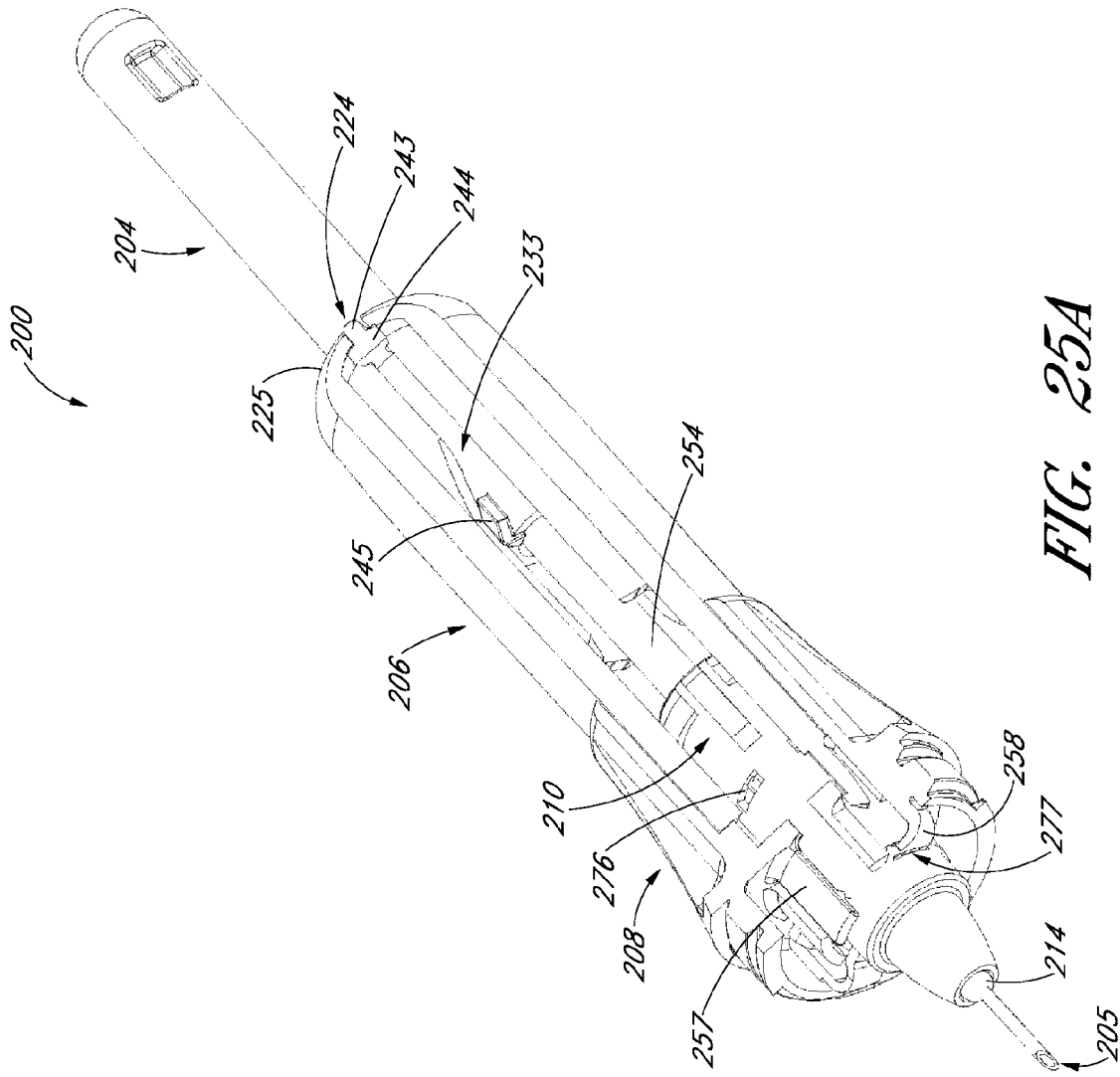
FIG. 25A illustrates a rear perspective partial cross-sectional view of the device of FIG. 25, with the sleeve and biasing member not illustrated for clarity.
Figure 25B:
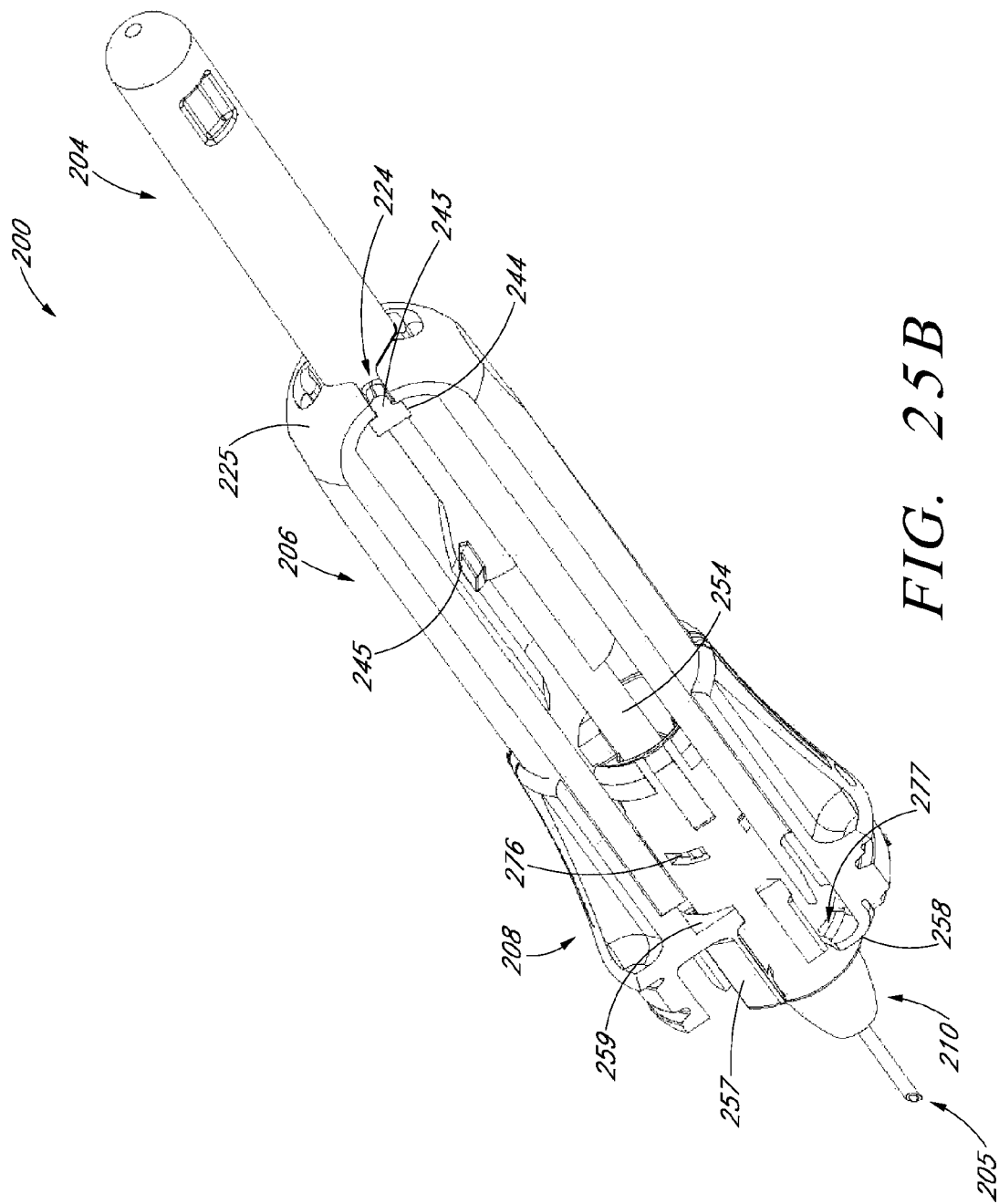
FIG. 25B illustrates a front perspective partial cross-sectional view of the device of FIG. 25, with the sleeve and biasing member not illustrated for clarity.

With regard to FIGS. 25-25B, in certain configurations, rotation of the sheath 204 results in the sheath 204 being released to move distally. For example, rotation of the sheath 204 can result in the wings 243 no longer being inhibited in the distal direction by the valley 234 of the frame 230 of the housing 206. In some implementations, the wings 243 are rotated into alignment with the longitudinal conduit 233. The sheath 204 can thus be moved distally, such as by the bias of the biasing member 212.

In some implementations, after being released, the distal end 241 of the sheath 204 moves distally into abutment with the surface being penetrated by the needle 202 (e.g., the patient's skin). In certain embodiments, after the sheath 204 has been released, the sheath 204 covers at least a portion of the needle 202 distal of the distal end 221 of the housing 206 and remains biased distally by the bias of the biasing member 212. In some variants, as the sheath 204 moves distally, the wings 243 pass through at least some the longitudinal conduit 233.

In certain implementations, the wings 243 slide along the ramp 235 prior to entering the longitudinal conduit 233, thereby providing a slight resistance. A resistance can, for example, provide feedback to the user of the device 200 that the sheath 204 is about to be released. Feedback can, for example, allow the user and/or patient to expect and/or prepare for movement of the sheath 204.

In some embodiments, the foot 245 of the sheath 204 is stationary with regard to the intermediate member 208, yet traverses through a portion of the longitudinal track 279 of the piston 210 due to the distal movement of the piston 210. In some configurations, such as after the sheath 204 has been released to move distally, the foot 245 of the sheath 204 traverses through a portion of the longitudinal track 279 (e.g., proximally) and is not stationary with regard to the intermediate member 208.

In some variants, distal movement of the vial is limited by the abutment members 256. For example, the abutment members 256 can present a rigid stop to the sleeve 216. Such a configuration can, for example, inhibit or prevent the sleeve 216 from being threaded too far distally relative to other components, which could result in damage to the sleeve 216 and/or other components of the device 200. For example, the abutment members 256 can inhibit or prevent the partition 283 from contacting the distal end of the rail 254, which could dislodge the boot 214.

As noted above, the vial or other container or adaptor can move the piston 210 distally as the vial is being engaged with the device 200. In some embodiments, when the distal end of the vial is nearly abutted against the partition 283 of the sleeve 216, the resilient arms 258 of the intermediate member 208 engage with the proximal notch 277 of the piston 210, which can counteract the force of the biasing member 212 and thus reduce or eliminate the amount of distal force that the user needs to apply to the vial to maintain it in position in the device 200. Such a configuration can, for example, reduce the likelihood of the piston 210 and/or the vial being inadvertently moved proximally by the biasing member 212, which could result in a spill or aspiration of blood.

In various embodiments, if further samples of blood are desired, the vial can be disengaged from the device 200 by moving the vial 200 proximally, thereby extracting the proximal end 205 of the needle 202 from the vial. In certain implementations, as the vial is moved proximally, the biasing member 212 will encourage the piston 210 proximally. In some embodiments, removal of the vial allows the piston 210 and/or the boot 214 to return to its original position (e.g., having a portion disposed proximal of the proximal end 205 of the needle 202). In certain implementations, the resilient arms 258 of the intermediate member 208 re-engage with the distal notch 277' of the piston 210, which can provide a slight resistance against incidental contact with the piston 210. After disengagement of the vial, another vial or vials can be engaged with the device 200.

After the desired number of samples has been collected, the user normally moves the device 200 proximally, thereby extracting the distal end 203 of the needle 202 from the patient. In some embodiments, as the distal end 203 of the needle 202 is extracted proximally, the sheath 204 is automatically moved distally (e.g., relative to the distal end 203 of the needle 202) by the bias of the biasing member 212.

Figure 26:
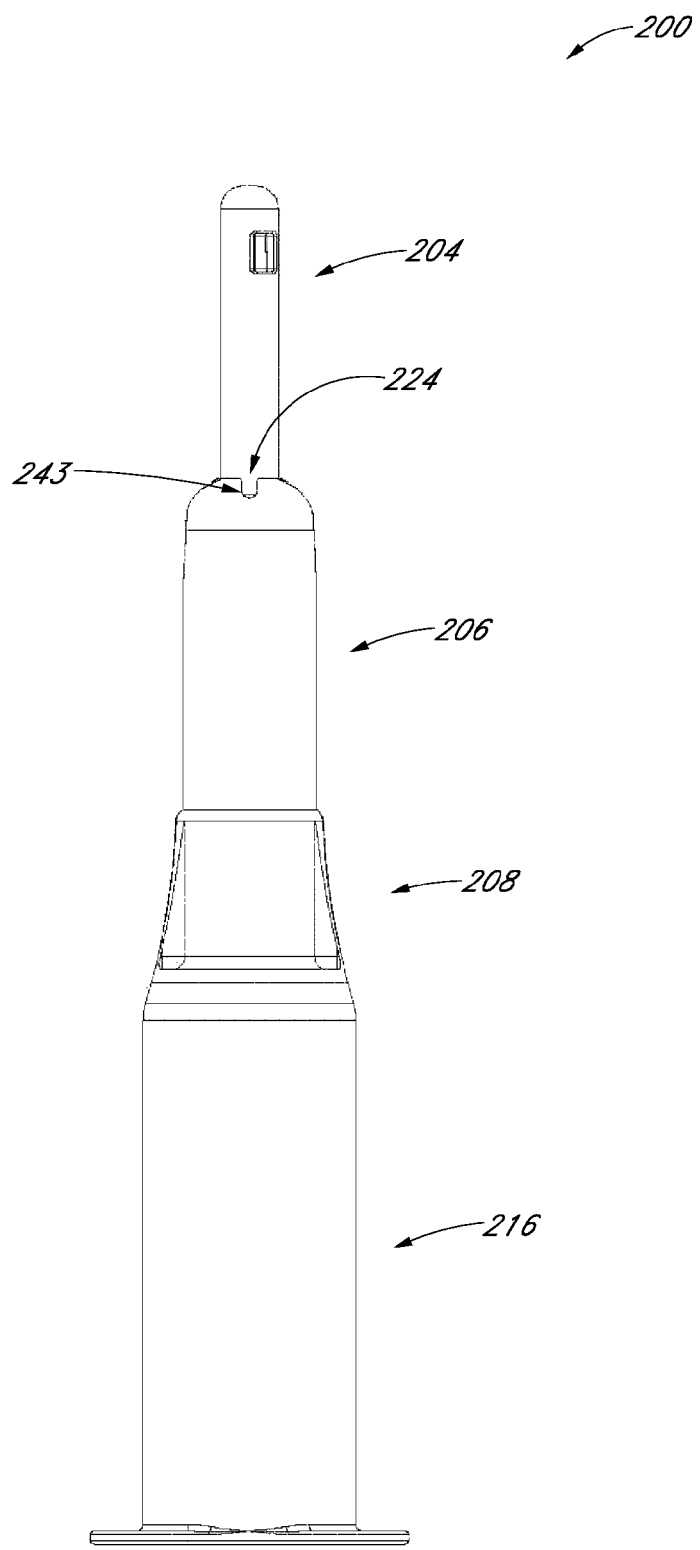
FIG. 26 illustrates a front view of the device of FIG. 15 in a locked state.
Figure 26B:
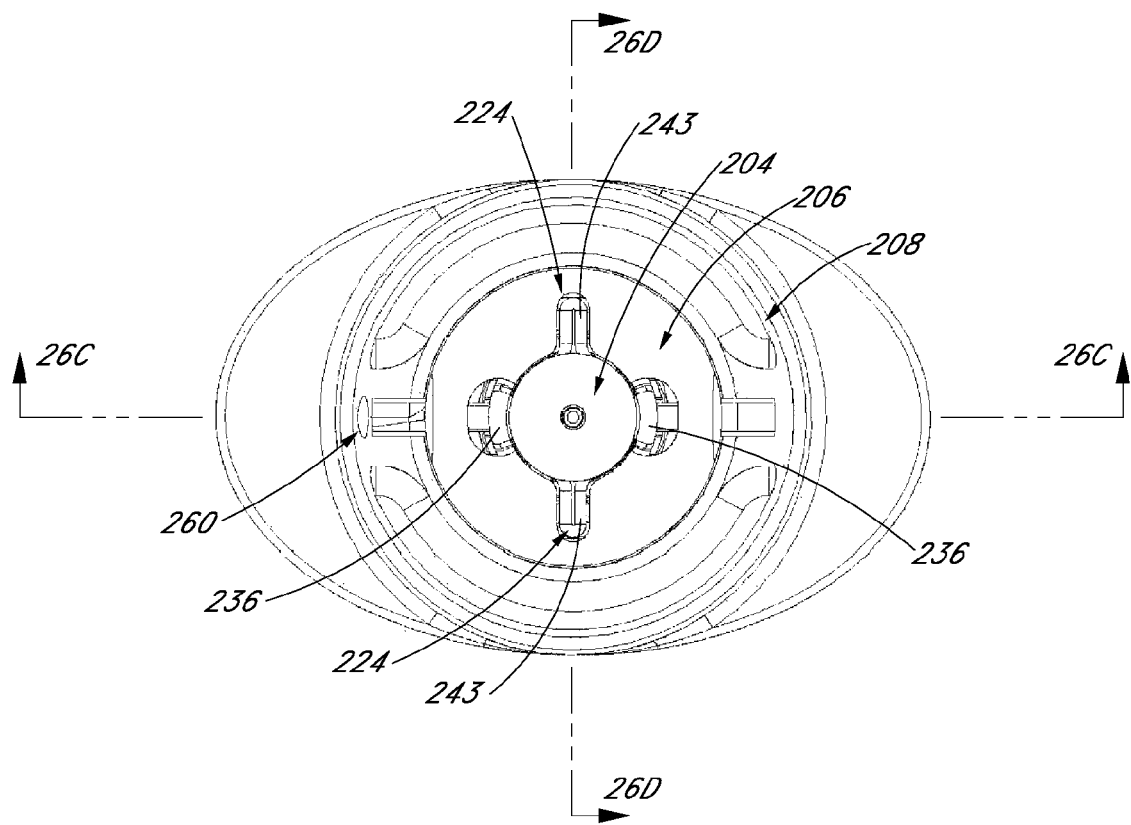
FIG. 26B illustrates a top view of the device of FIG. 26.
Figure 26C:
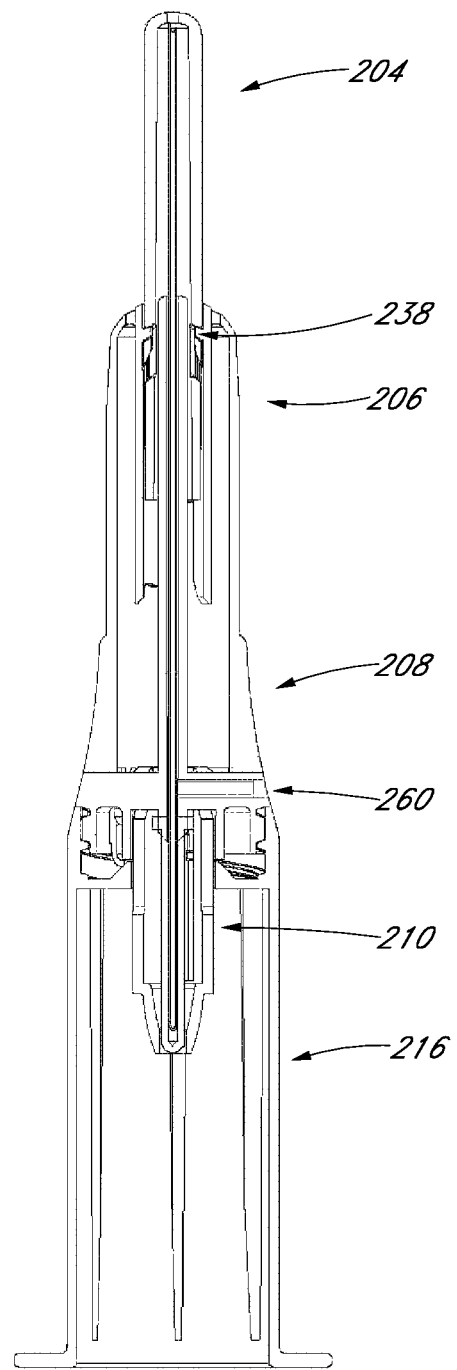
FIG. 26C illustrates a cross-sectional view along the line 26C-26C of FIG. 26.
Figure 26D:
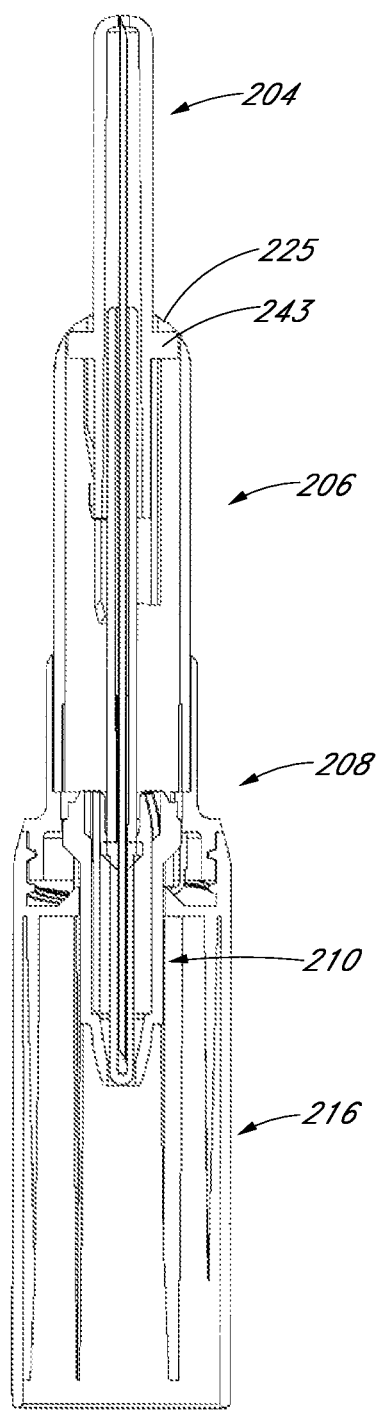
FIG. 26D illustrates a cross-sectional view along the line 26D-26D of FIG. 26.

As illustrated in FIGS. 26-26D, after the needle 202 has been fully removed from the patient, the sheath 204 can move toward its fully distal position. Generally, in the fully distal position, a portion of the sheath 204 is positioned distal of the distal end 203 of the needle 202. Such a configuration can, for example, promote safety by shielding persons from the sharp distal end 203. Further, because the sheath 204 is automatically moved to cover the distal end 203 of the needle 202, such a passive safety feature does not require the user to activate, trigger, or otherwise engage such a feature and diminishes the risk of inadvertent harm to the patient and/or healthcare worker caused by failure to deploy an active safety feature.

In some embodiments, distal movement of the sheath 204 is limited. For example, the winglets 244 of the sheath 204 can abut with an inner surface of the shoulder 225 of the housing 206, thereby inhibiting or preventing further proximal movement of the sheath 204. As illustrated, in some embodiments, the winglets 244 are positioned radially outward of the frame 230 of the housing 206.

In some configurations, proximal movement of the sheath 204 is limited. In certain embodiments, when the sheath 204 nears its fully distal position, the tooth 238 of the frame 230 of the housing 208 engages the proximal opening 247 of the sheath 204. Typically, the tooth 238 and the proximal window 247 are configured to resist proximal movement of the sheath 204. For example, the tooth 238 can be angled proximally. In certain variants, a distal end of the proximal opening 247 has a complementary shape with regard to the tooth 238. For example, both the tooth 238 and the proximal opening 247 can be angled proximally.

Generally, when the sheath 204 has moved to its generally fully proximal position, it is retrained from moving distally (e.g., by the abutment of the winglets 244 with the shoulder 225) and proximally (e.g., by engagement of the tooth 238 and the proximal window 247). In some configurations, the sheath 204 is described as being in a locked-out state. In the locked-out state, the distal end 203 of the needle 202 generally cannot be re-exposed, thereby preventing inadvertent sticking with the distal end 203. Further, as reuse of the device 200 is generally not possible when the sheath 204 is in the locked-out state, the device 200 can avoid the risk of transmitting blood-born pathogens that could occur when needles are reused.

Certain variants include an indication that the sheath 204 is substantially at its fully distal position. For example, in some embodiments, when the winglets 244 abut with the shoulder 225, a portion of the wings 243 extend at least partly through the indication channel 224 of the housing 206. In some such embodiments, the wings 243 can be visually observed external of the device 200, thereby providing a signal that the sheath 204 is generally in its fully distal position.

As noted above, the sleeve 216 can be configured to attach to other components of the device 200. For example, the sleeve 216 can attach to the intermediate member 208 with a threaded connection. Certain embodiments of the sleeve 216 are also configured to be removable. For example, some variants of the sleeve 216 can be removed from the intermediate member 208 by unscrewing the threaded connection. In some embodiments, removal of the sleeve 216 disengages the wedge 285 from the struts 257 of the intermediate member 208. In some implementations, such disengagement results in the struts 257 of the intermediate member 208 re-engaging with the windows 266 of the piston 210, thereby inhibiting further distal movement of the piston 210. Such a configuration can, for example, reduce the likelihood of a needle stick with the proximal end 205 of the needle 202.

Therefore, certain embodiments of the device 200 provide a passively-locking single-use blood collection instrument. In some embodiments, the proximal end 205 of the needle 202 can be rendered generally safe when the sleeve 216 is removed from the device 200. In some embodiments, the distal end 203 of the needle 202 can be rendered generally safe after the piston 210 has been moved distally (e.g., by insertion of the vial) and the sheath 204 has been allowed to travel to its fully distal position. Indeed, certain embodiments of the device 200 can render generally safe both the distal and proximal ends 203, 205, thereby providing protection at both ends of the needle 202. Some embodiments of the device 200 provide protection even after the sleeve 216 has been removed. Furthermore, the locking features of the device 200 can prevent reuse.

Figure 27:
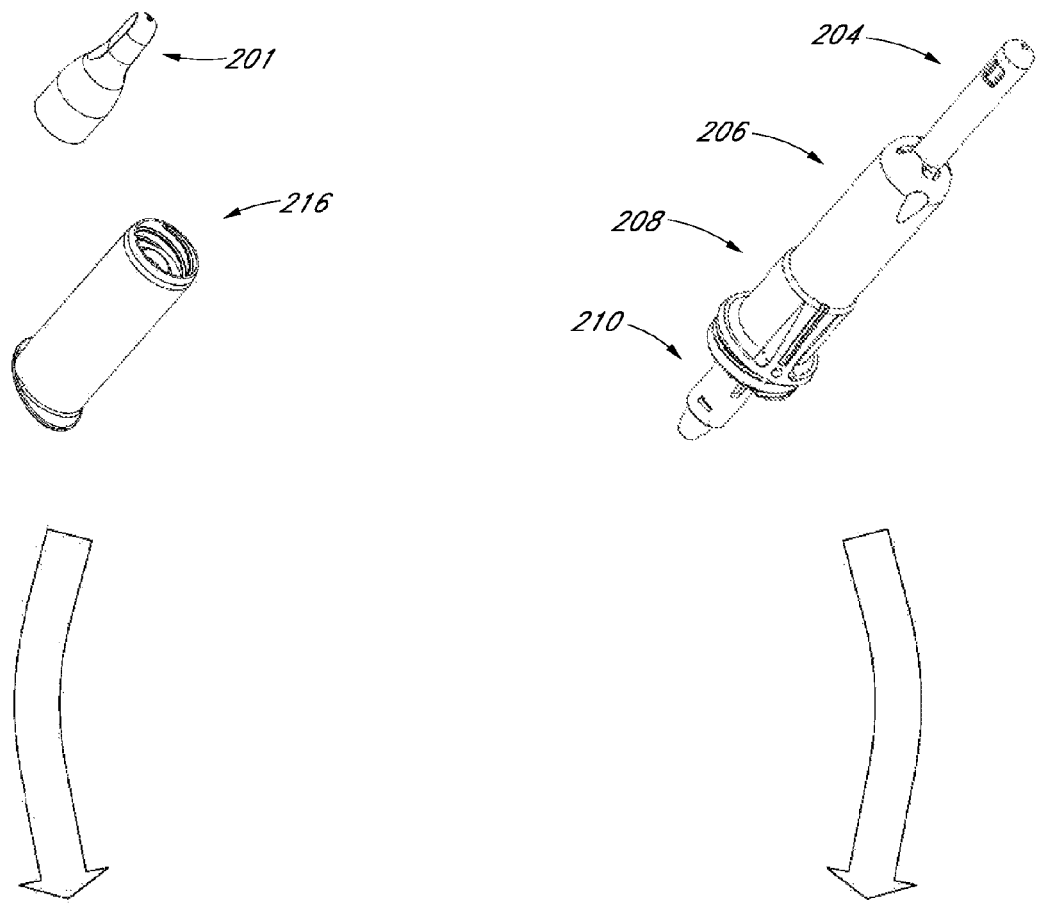
FIG. 27 illustrates a schematic disposal diagram of certain components of the device of FIG. 15.

With reference to FIG. 27, after the blood collection procedure has been completed, the device 200 is normally disposed of. Disposal of devices including needles and other types of medical waste are generally subject to laws, codes, and/or regulations requiring special "sharps" disposal methods and procedures. For example, many states require that items including needles be disposed of in dedicated rigid leak-proof containers and be disposed of in particular locations and/or by hazardous waste organizations. In many instances, the cost to dispose of "sharps" waste is weight-based and can be quite expensive due to the special care that such waste requires. Therefore, it can be desirable to reduce the weight (and thus the cost of disposal) of items that will be subject to "sharps" disposal requirements. In some embodiments, a portion of the device 200 comprising a substantial proportion of the weight of the device 200 can be disposed of in a non-"sharps" disposal receptacle. For example, as certain embodiments of the sleeve 216 do not include a needle, the sleeve 216 typically can be disposed of as standard waste or non-"sharps" waste. Likewise, in certain embodiments, the cap 218 can be configured to be removed from the rest of the device 200 and be disposed as standard waste or non-"sharps"

waste. Thus, removal of the sleeve 216 and/or cap 218 can reduce the weight of the device 200 that is disposed of as "sharps" waste, which in turn can reduce the cost to dispose of the device 200. In some embodiments, a method of manufacturing or providing a blood connection device 200 can include instructing healthcare providers and/or patients to dispose of a portion of the device 200 in a "sharps" receptacle and to dispose of another portion of the device 200 in an ordinary and/or conventional medical refuse receptacle.

As noted above, some embodiments device 200 may be configured for disposal in a non-"sharps" disposal receptacle. For example, some or all of the device 200 can be disposable as hazardous waste or other non-"sharps" waste. Certain variants may be disposable as non-"sharps" waste at least partly due to the needle 202 being substantially, substantially entirely, or entirely contained in the device 200 after the device 200 has been used (e.g., in a blood collection procedure), thereby greatly reducing or eliminating the potential of the needle 202 to pierce or rupture the disposal container (e.g., a plastic bag or cardboard box) and/or to produce skin laceration or puncture injuries. For example, as discussed above, after the device 200 has been used, a portion of the sheath 204 can extend beyond and cover the distal end 203 of the needle 202 and a portion of the piston 210 can extend beyond and cover the proximal end 203 of the needle 202. Further, the sheath 204 and the piston 210 can be configured to lock, thereby preventing the needle 202 from projecting from the sheath 204 and piston 210. Some variants of the device 200 may be disposable as non-"sharps" waste because, for example, the device 200 can automatically and passively secure the sheath 204 and piston 210 after the device 200 has been used.

In certain configurations, portions of the device 200 can form a protective enclosure around the needle 202, thereby reducing or eliminating the need for disposing the device 200 in a separate "sharps" container. For example, the sheath 204, housing 206, intermediate member 208, and piston 210 can form a protective enclosure around the needle 202 after the device 200 has been used. In certain embodiments, the protective enclosure may render the device 200 suitable for disposal as non-"sharps" waste, such as hazardous waste. In some variants, the sheath 204 and/or piston 210 include sealing elements (e.g., a resilient flap, septum, or otherwise) that are configured to generally seal the distal hole 248 of the sheath 204 and/or the hollow proximal end 272 of the piston 210 at least after the device 200 has been used, thereby reducing the possibility of fluid (e.g., blood) from the needle 202 leaking from the device 200.

In certain embodiments, after the device 200 has been used, the needle 202 is substantially or completely obscured from view. In some embodiments, after the device 200 has been used, the only portions of the needle 202 that are visible from outside the device 200 are the distal and proximal ends 203, 205. In certain implementations, after the device 200 has been used, the distal and proximal ends 203, 205 are visible only through the distal hole 248 of the sheath 204 and the hollow proximal end 272 of the piston 210.

FIGS. 28-35 illustrate yet another embodiment of a blood collection safety device 300. The blood collection safety device 300 can use components, portions, and/or features that are the same as or identical to those described herein with respect to other blood collection safety devices disclosed herein. Any features and/or components of the disclosed embodiments can be combined or used interchangeably.

Figure 28:
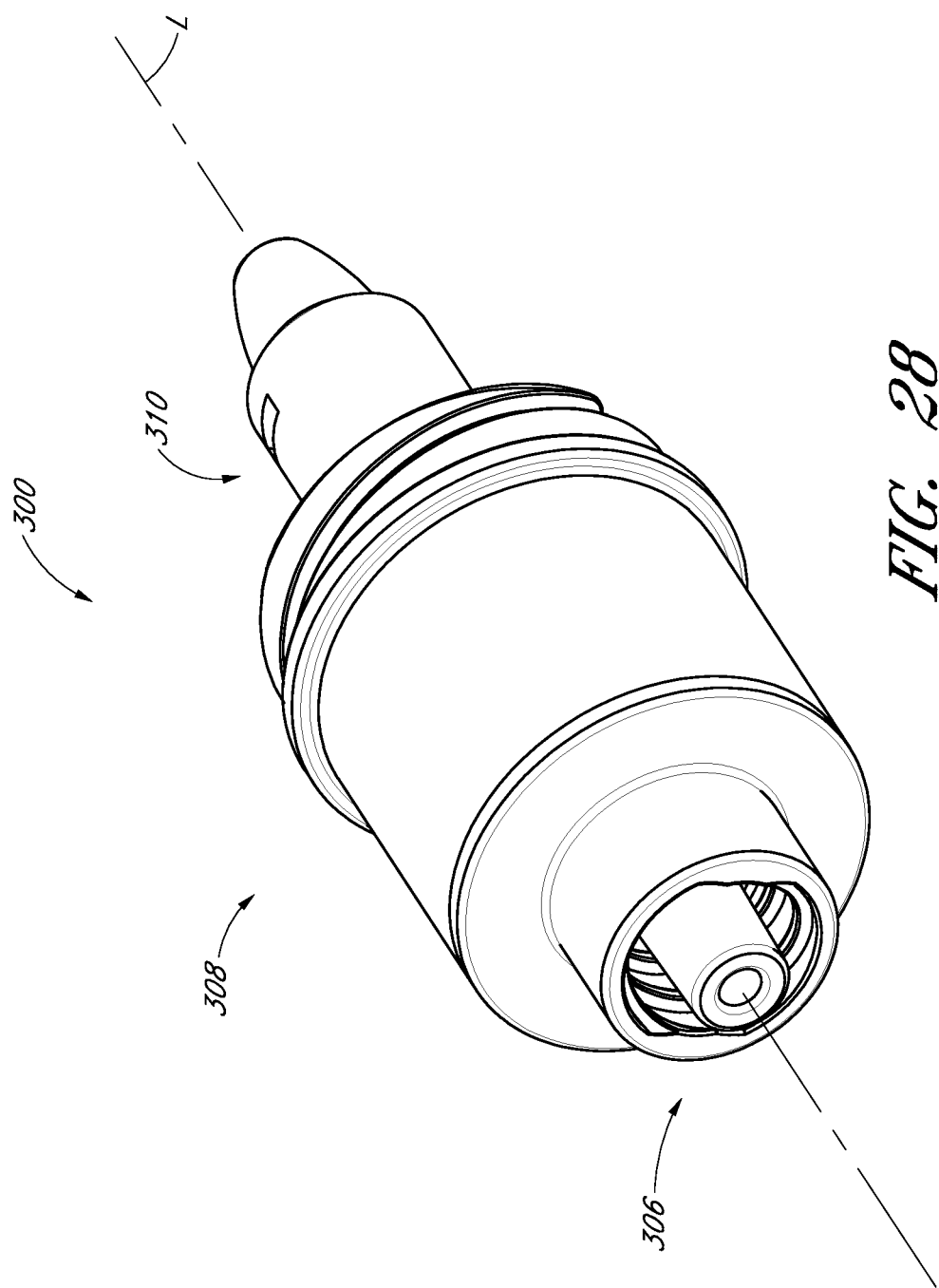
FIG. 28 illustrates a perspective view of another embodiment of a blood collection safety device having a housing, intermediate member, and piston.
Figure 28A:
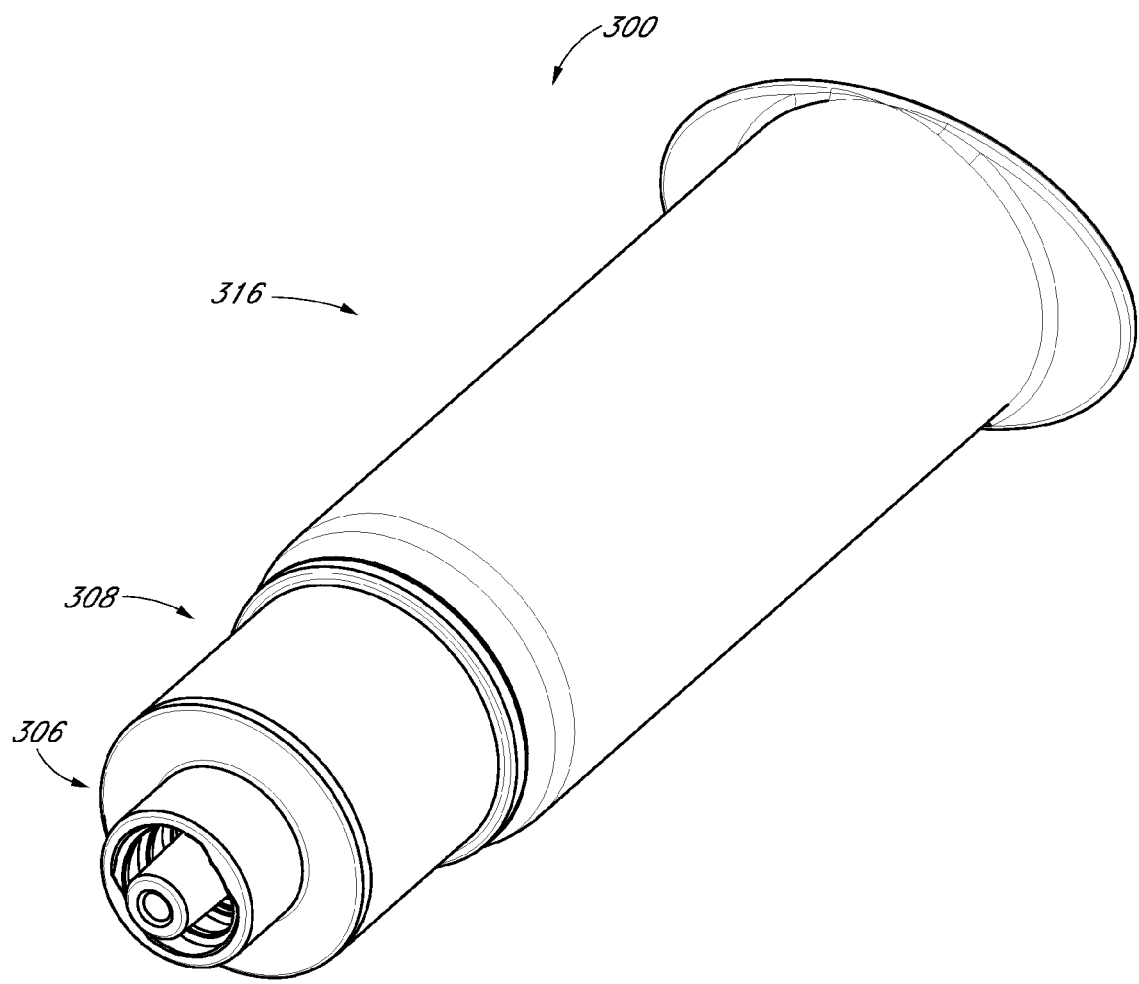
FIG. 28A illustrates a perspective view of the device of FIG. 28 coupled with a sleeve.
Figure 29:
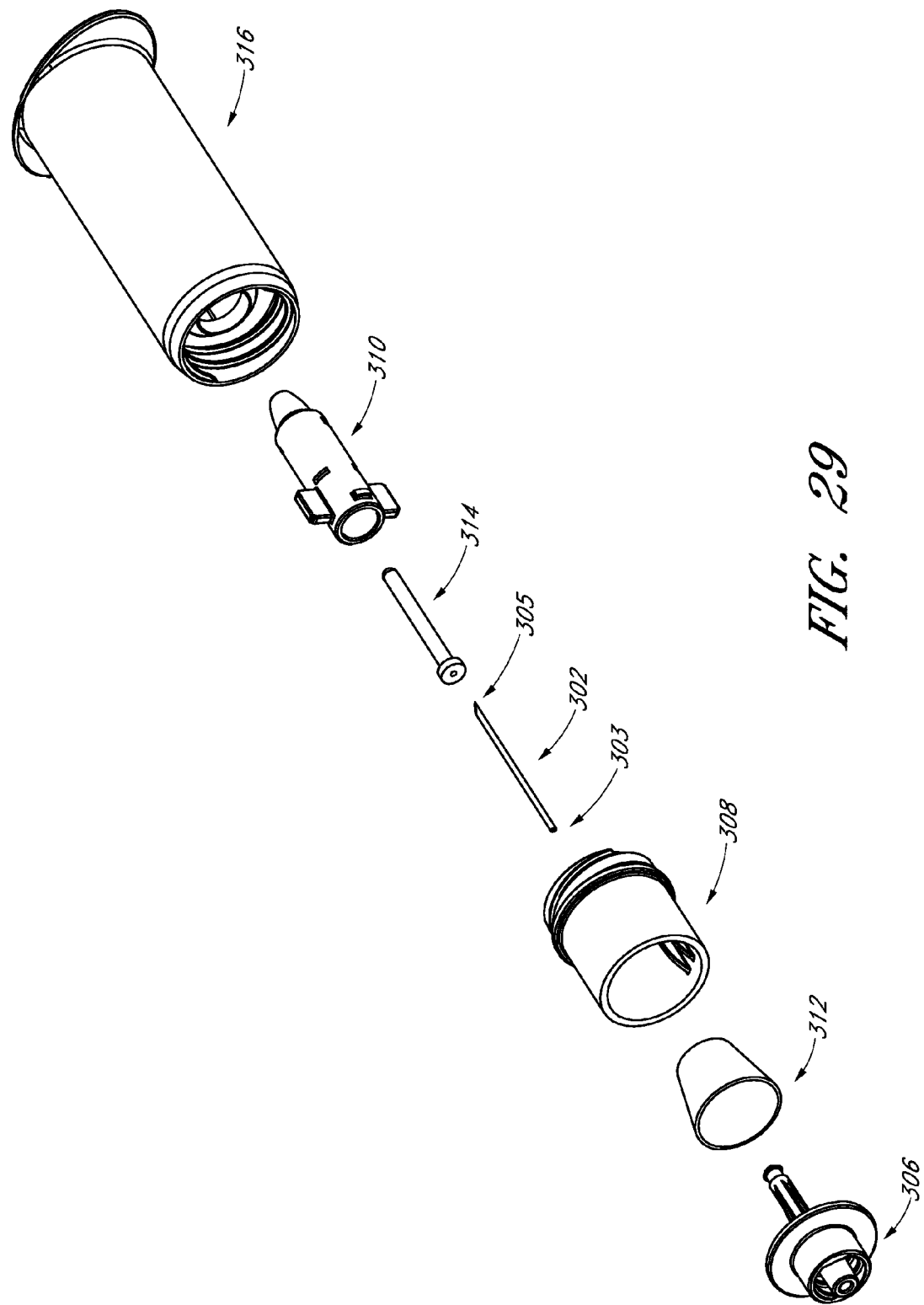
FIG. 29 illustrates a perspective exploded view of the device of FIG. 28A.

With reference to the assembled views of FIGS. 28 and 28A, as well as the exploded view of FIG. 29, an embodiment of the blood collection safety device 300 is illustrated. In certain configurations, the device 300 can be configured to mate with a blood collection vial or other container or adaptor (not shown). As illustrated, some embodiments of the device 300 include a connector member 306, an intermediate member 308, and a piston 310 that are generally aligned along a longitudinal axis L. Certain implementations include a sleeve 316 that is generally aligned along the axis L. In some embodiments, the sleeve 316 is similar or identical to the sleeve 216 described above. In certain variants, the sleeve 316 is removably secured to the intermediate member 308, such as with threads, clips, friction fit, bayonet connection, or otherwise. Some embodiments include a biasing member 312, such as a spring. For example, in some variants, the biasing member 312 comprises a helical spring, wave-spring, belleville washers, or otherwise.

As illustrated, the device 300 can include a needle 302 and a resilient boot 314. In some implementations, the needle 302 has a distal end 303 and a proximal end 305. In certain embodiments, at least the proximal end 305 comprises a sharp tip (e.g., configured to pierce a cover of a blood collection vial). In certain modes of the device 300, the proximal end 305 of the needle 302 is covered by the piston 310 (e.g., a portion of the piston 310 extends proximally beyond the proximal end 305). In other modes, the proximal end 305 of the needle 302 is exposed by the piston 310. In some embodiments, as will be discussed in greater detail below, the piston 310 can be configured to reciprocate, telescope, move, or otherwise be at least partly received within the intermediate member 308.

Figure 30:
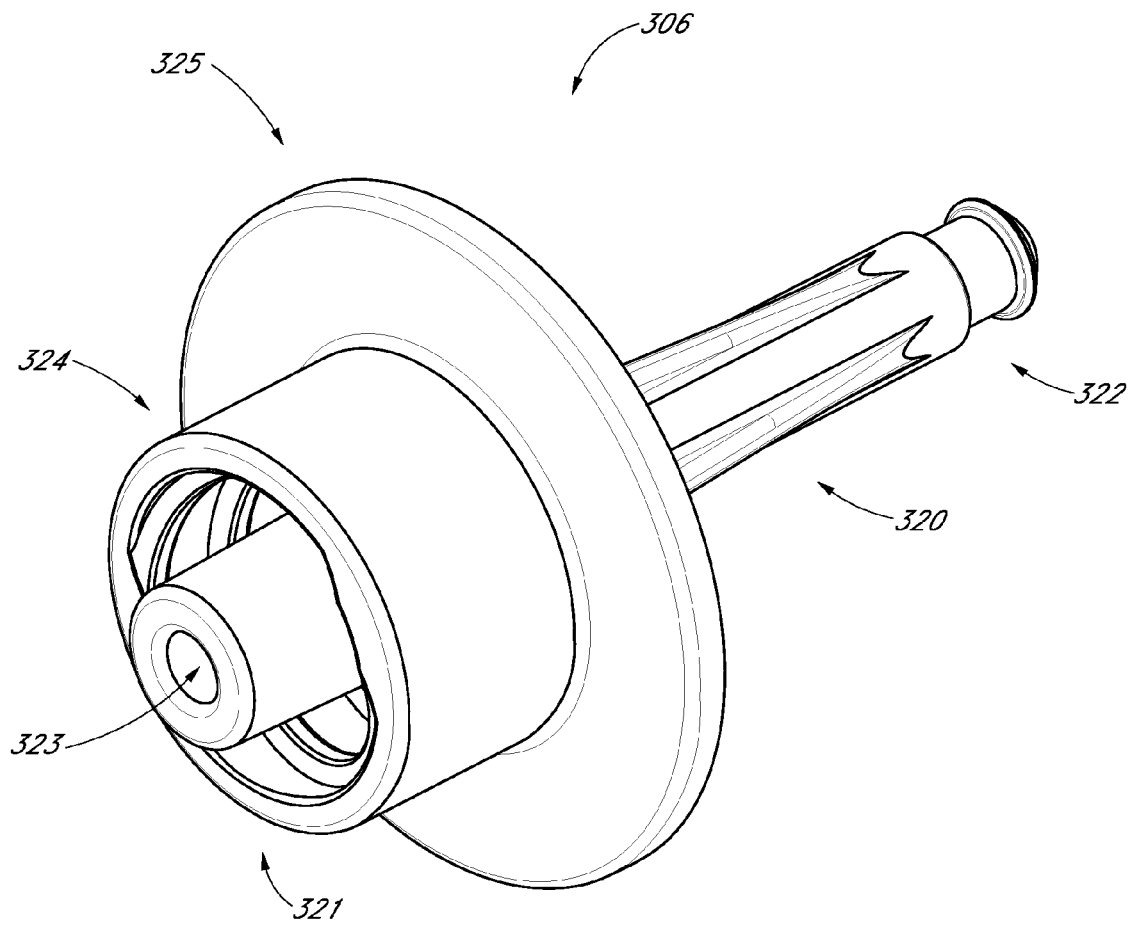
FIG. 30 illustrates a perspective view of an embodiment of the housing of the device of FIG. 28.
Figure 30A:
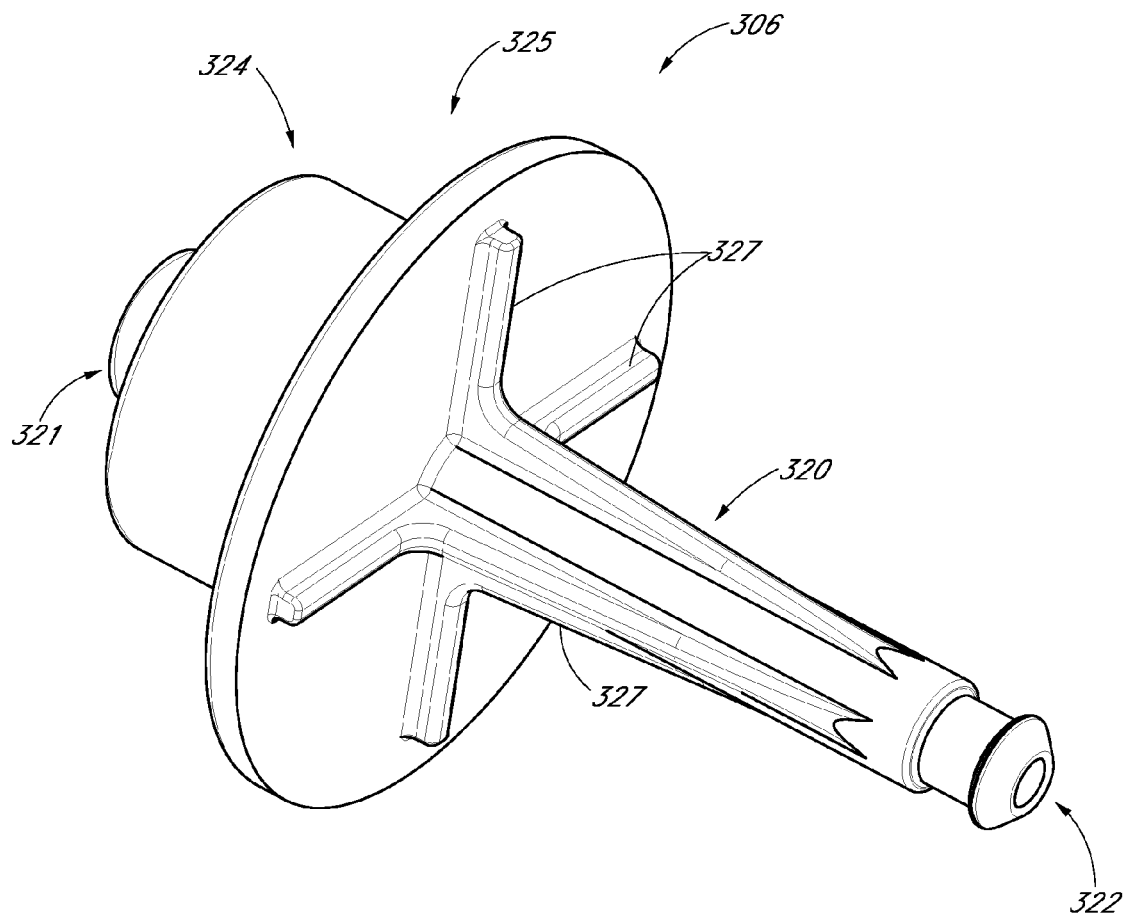
FIG. 30A illustrates another perspective view of the housing of FIG. 30.

With regard to FIGS. 30 and 30A, an embodiment of the connector member 306 is illustrated. In some implementations, the connector member 306 includes an elongate hollow body 320, a distal end 321, and a proximal end 322. In some embodiments, a portion of the proximal end 322 includes a retaining feature, such as a flange, that is configured to connect with the resilient boot 314 (e.g., by a friction fit). In some variants, the connection between the boot 314 and the proximal end 322 is substantially liquid tight. As illustrated, the connector member 306 can include a distal aperture 323 in fluid communication with the hollow body 320.

Some embodiments of the connector member 306 include a medical connector interface 324, which can be configured to engage with any suitable medical connector. For example, the medical connector interface 324 can be configured to engage with a needleless IV access device. As illustrated, the medical connector interface can comprise a male luer with a luer-lock shroud configured to be inserted into a corresponding female luer connector or another medical device, such as a catheter or shunt, connected to a patient. Many other structures and configurations can be used. For example, the medical connector interface 324 can comprise a female luer connector configured to be attached to a male luer connector on another medical device. In some embodiments, the medical connector interface 324 is threaded, configured to accept a Luer connector, or otherwise shaped to attach directly to a medical device or other instruments. In certain variants, the medical connector interface 324 includes a passage or channel, such as a length of tubing. As illustrated, certain embodiments include a radially outwardly extending shoulder 325, which can be generally flat, generally curved, or otherwise shaped.

In some embodiments, the connector member 306 includes one or more support members, such as ribs 327. In some embodiments, a portion of the ribs 327 extends generally longitudinally along a portion of the elongate body 320. In certain variants, a portion of the ribs 327 extends generally outwardly along a portion of the shoulder 325. Certain embodiments of the ribs 327 are configured to support a portion of the biasing member 312. For example, the ribs 327 can be configured to position a distal end of the biasing member 312 and/or inhibit the biasing member 312 from becoming misaligned with respect to the elongate body 320. Some implementations of the struts are configured to facilitate generally longitudinal sliding movement of the piston 310 along a portion of the elongate body 320. For example, the ribs 327 can reduce friction between the piston 310 and the elongate body 320 and/or can help to align the piston 310 with respect to the elongate body 320.

Figure 31:
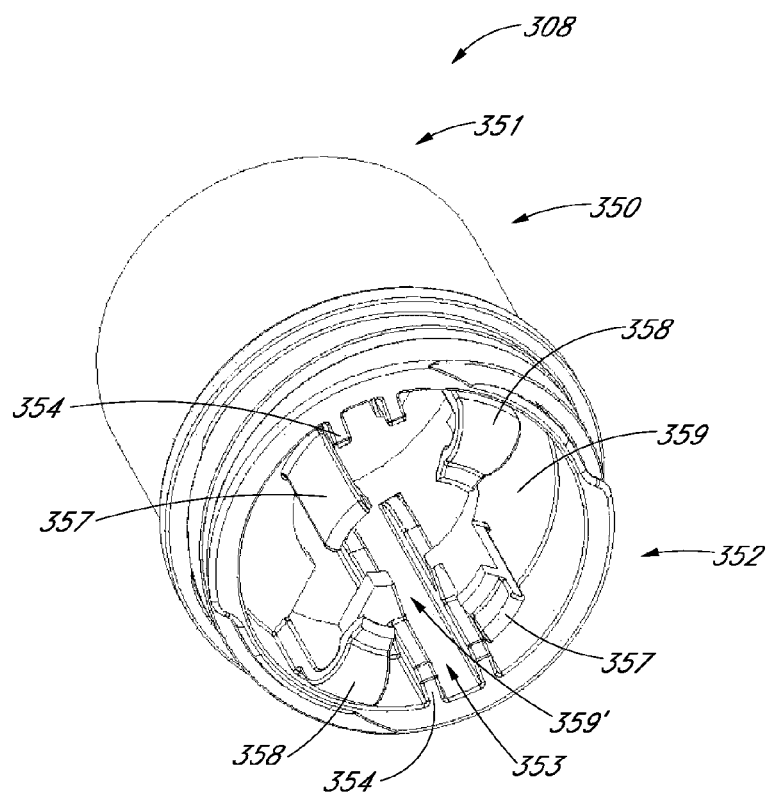
FIG. 31 illustrates a perspective view of an embodiment of the intermediate member of the device of FIG. 28.
Figure 31A:
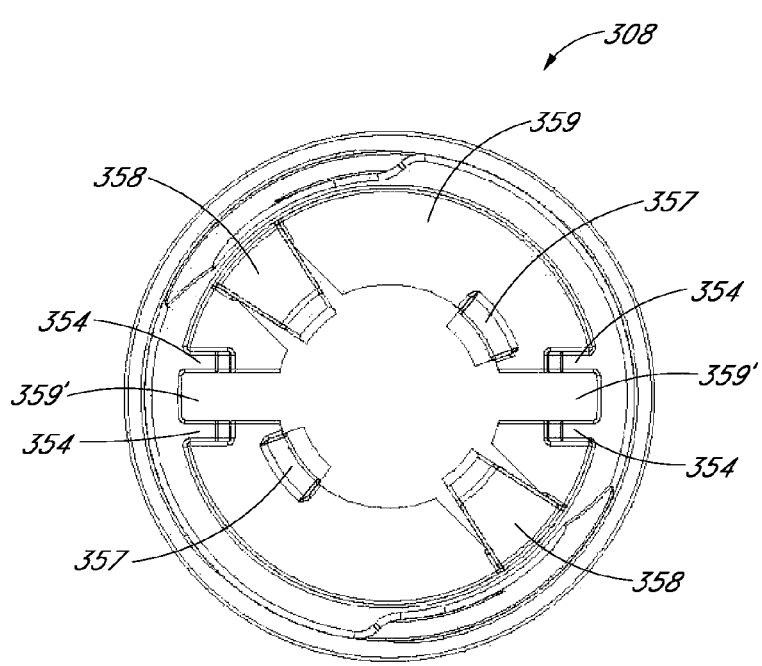
FIG. 31A illustrates a rear view of the intermediate member of FIG. 31.

With regard to FIGS. 31 and 31A, an embodiment of the intermediate member 308 is illustrated. Some embodiments of the intermediate member 308 include a generally hollow body portion 350, distal end 351, and proximal end 352. In certain variants, the proximal end 352 comprises a connection member, such as threads. In some embodiments, the body portion 350 includes an engagement structure, such as at least one longitudinal slot 353. In certain embodiments, the slot 353 is positioned on a radially inner surface of the body portion 350. Some variants include a guide structure, such as a fence 354, on one or more sides of the slot 353.

The proximal end 352 of the intermediate member 308 can include a plurality of first engagement members, such as resilient struts 357, which can include a radially inwardly extending portion. In certain variants, the intermediate member 308 includes a plurality of second engagement members, such as resilient arms 358. As shown, the resilient arms 358 can include a radially inwardly extending portion. Similar to the resilient struts 257 and the resilient arms 258 discussed above in connection with device 200, the resilient struts 357 and the resilient arms 358 can be configured to engage and/or disengage with certain features of the piston 310. In some embodiments, the resilient struts 357 and/or the resilient arms 358 connect with, or extend proximally from, a radially inwardly extending support member, such as a shoulder 359, of the body portion 350. In some variants, the shoulder 359 includes a movement enabling structure, such as one or more spaces 359'.

Figure 32:
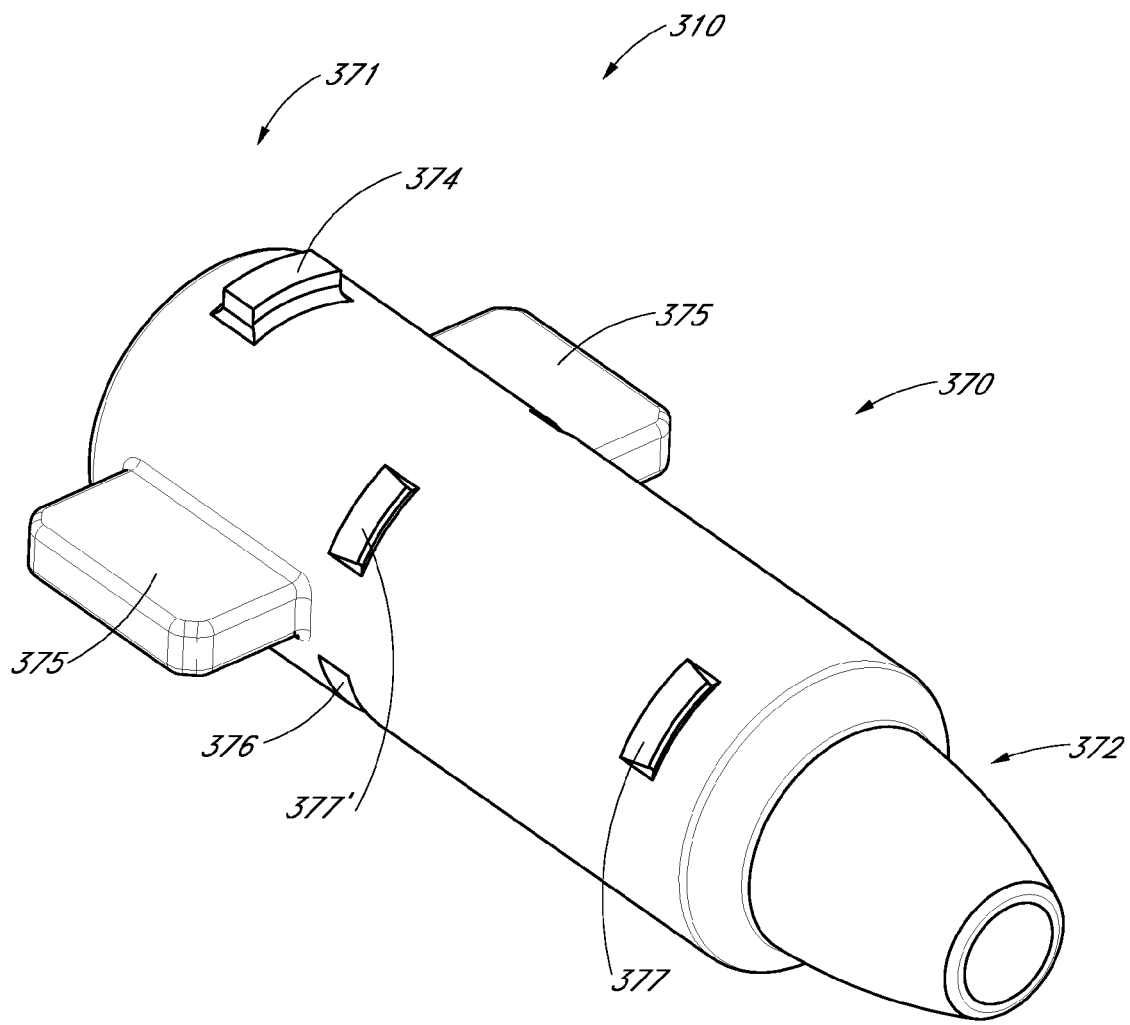
FIG. 32 illustrates a perspective view of an embodiment of the piston of the device of FIG. 28.

With reference to FIG. 32, an embodiment of the piston 310 is illustrated. The piston 310 can include a hollow tube 370, a distal end 371, and a proximal end 372. In some embodiments, the proximal end 372 has a generally rounded shape and/or has a smaller diameter than the hollow tube 370. Such a configuration can, for example, assist in mating with the blood collection vial (e.g., can facilitate a substantially air-tight seal between the proximal end 372 and the vial). In some embodiments, the proximal end 372 is generally flat.

In certain embodiments, piston 310 includes one or more engagement structures, such as protrusions 374 and/or flange 375. As illustrated, certain variants of the protrusions 374 and/or flanges 375 extend radially outward from the hollow tube 370. Some embodiments include one or more windows 376. In certain embodiments, the windows 376 are recesses in the hollow tube 370. In other implementations, the windows 376 fully extend through the width of the hollow tube 370.

In certain implementations, the piston 310 includes one or more engagement structures, such as notches 377 (e.g., wedge-shaped recesses), at or near the proximal end 372. In certain variants, the piston 310 includes one or more notches 377' positioned distal of the notches 377. The notches 377, 377' can be generally circumferentially aligned (e.g., such that the notches 377, 377' are generally collinear on a line generally parallel with the axis L). The notches 377, 377' can be configured to engage one or more features of the connector member 306 or intermediate member 308 to inhibit unintentional proximal movement of the piston 310.

Figure 33:
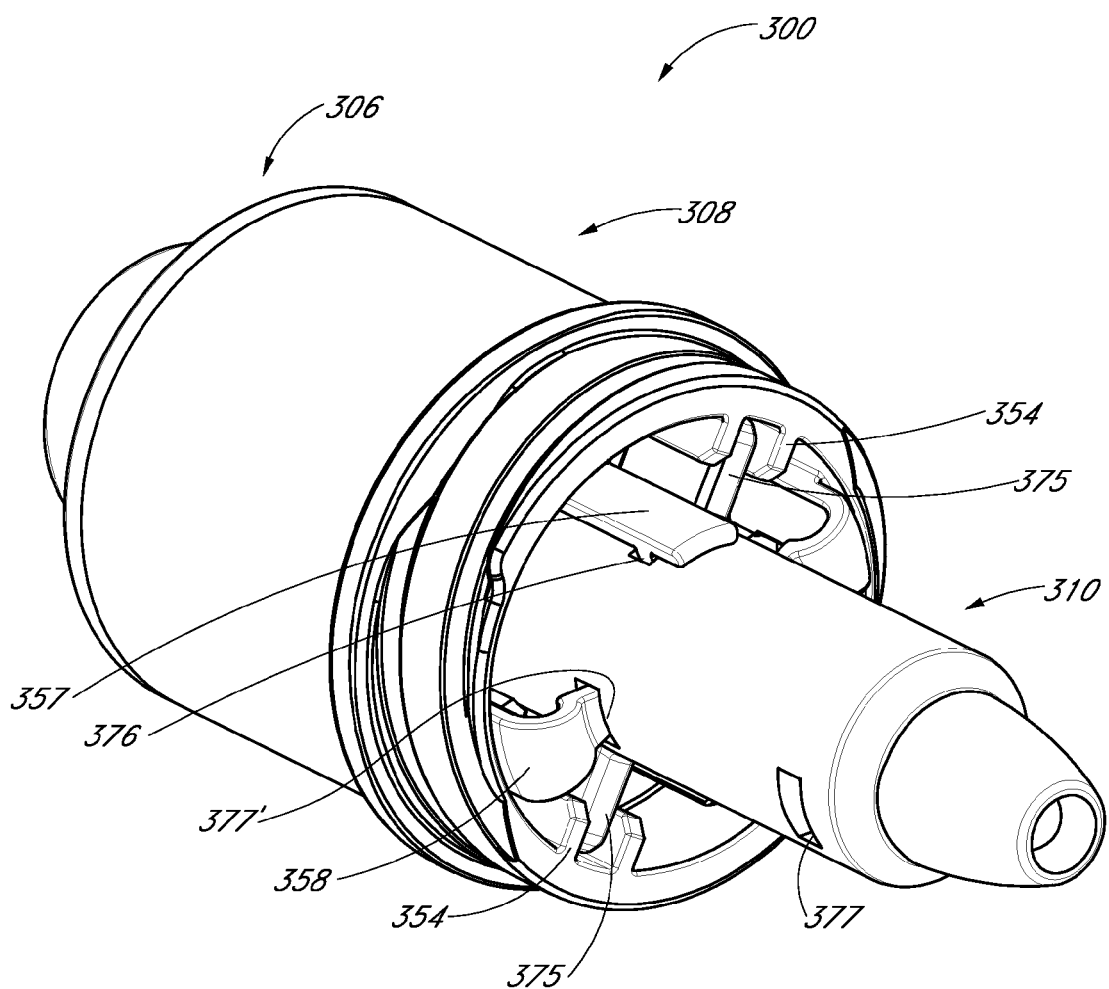
FIG. 33 illustrates a perspective view of the device of FIG. 28 in an initial state.

With reference to FIGS. 28 and 33, the device 300 in an initial state is illustrated. In certain embodiments, in the initial state, the sleeve 316 is separate from the rest of the device 300. For example, in some embodiments, in the initial state, the sleeve 316 is not coupled with the intermediate member 308. Such a configuration can, for example, provide an arrangement in which the device 300 can be stored or shipped.

In some embodiments, in the initial state, piston 310 is inhibited from moving distally relative to the needle 302, thereby providing a generally locked covering for the sharp proximal end 305 of the needle 302 and decreasing the chance of an accidental needle stick. For example, in certain implementations, the piston 310 is inhibited from moving distally relative to the needle 302 because the resilient struts 357 of the intermediate member 308 engage with the windows 376 of the piston 310, thereby providing a radial interference. In some variants, the struts 357 and/or the windows 376 can be shaped or otherwise configured such that even if a distally-directed force is applied to the piston 310, the struts 357 and the windows 376 remain engaged. In certain embodiments, in the initial state, the resilient arms 358 of the intermediate member 308 engage the distal notches 377' of the piston 310, thereby providing a secondary radial interference to resist movement.

In some embodiments, the sleeve 316 can be configured to couple with the intermediate member 308 (e.g., via a threaded connection). Similar to the discussion above in connection with the engagement of the sleeve 216 and the intermediate member 208 of the device 200, in some embodiments, engagement of the sleeve 316 and the intermediate member 308 can disengage the struts 357 of the intermediate portion 308 from the windows 376 of the piston 310. For example, a wedge 385 of the sleeve 316 can deflect the struts 357 radially outwardly, thereby removing the radial interference between the struts 357 and the windows 376.

Figure 34:
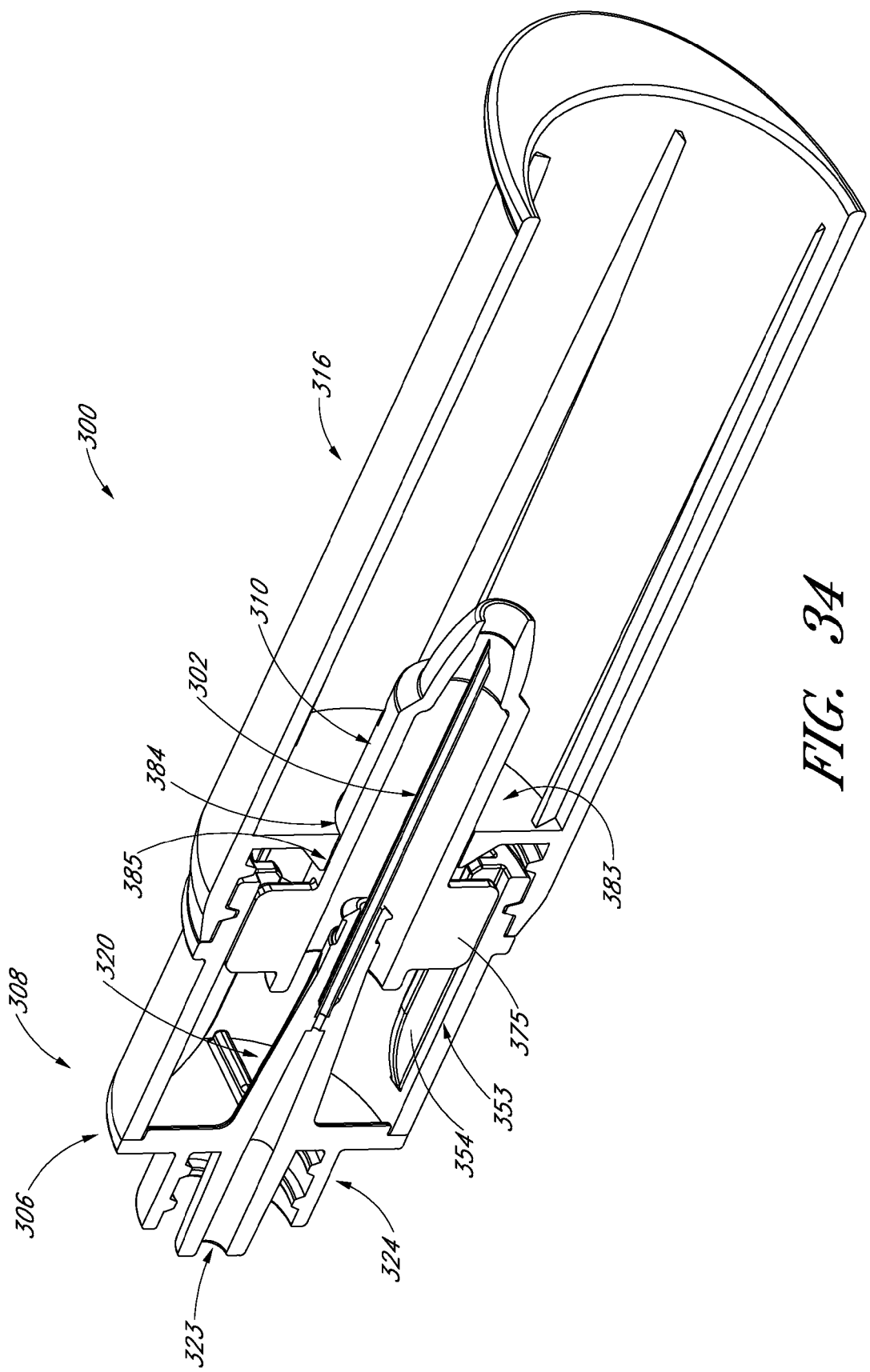
FIG. 34 illustrates a cross-sectional perspective view of the device of FIG. 33 in a ready-to-operate state.

With regard to FIG. 34, a cross-sectional perspective view of the device 300 in a ready-to-operate state is illustrated. The ready-to-operate state can occur, for example, after the sleeve 316 has been coupled with the intermediate member 308. In certain embodiments, the device 300 is in the ready-to-operate state before a blood collection vial (not shown) has been engaged with the device 300. In some embodiments, the device 300 is in the ready-to-operate state after a blood collection vial has been disengaged from the device 300.

As illustrated in FIG. 34, the shoulder 325 of the connector member 306 can be connected with the distal end 351 of the intermediate member 308, such as with adhesive, welding, or other techniques. In some implementations, the ribs 327 of the connector member 306 extend radially outward along the shoulder 325 less than an inner diameter of the distal end 351 of the intermediate member 308, which can allow the shoulder 325 and the distal end 351 of the intermediate member 308 engage in a generally flush manner.

In certain embodiments, the needle 302 is mounted in, or otherwise connected with, the connector member 306, such as with adhesive, welding, or other techniques. As illustrated, the needle 302 can be spaced apart from the medical connector interface 324 by a distance along the axis L. A portion of the needle 302 can extend proximally from the connector member 306 and through a portion of the hollow tube 370 of the piston 310 and the boot 314 (not shown for clarity). As shown, in the ready-to-operate state, a portion of the proximal end 372 of the piston 310 can extend proximally of the proximal end 303 of the needle 302, which can shield the sharp proximal end 305 and reduce the likelihood of accidental needle sticks. In some arrangements, a portion of the piston 310 is received in, and projects proximally through, the aperture 384 of the sleeve 316.

As illustrated, a portion of the distal end 371 of the piston 310 can be received in the hollow body 350 of the intermediate member 308. The flange 375 of the piston 310 can be received in the longitudinal slot 353 and allowed to move therealong (e.g., with sliding reciprocating motion). In certain embodiments, the fence 354 is configured to generally maintain the flange 375 in the slot 353 and/or to inhibit rotational movement of the piston 310 with respect to the intermediate member 308. In certain implementations, a distance that the fence 354 extends radially inwardly from the inner surface of the body portion 350 is less than or equal to a distance that the flange 375 extends radially outwardly from an outer surface of the hollow tube 370. For example, in some embodiments, the fence 354 extends radially inwardly from the inner surface of the body portion 350 less than or equal to about ½ of the distance that the flange 375 extends radially outwardly from an outer surface of the hollow tube 370.

In some embodiments, the biasing member 312 (not shown for clarity) can be positioned and/or compressed between the connector member 306 and the piston 310. For example, a distal end of the biasing member 312 can be abutted against, or otherwise engaged with, the shoulder 325 of the connector member 306, and a proximal end of the biasing member 312 can be abutted against, or otherwise engaged with, the flange 375 of the piston 310. In some implementations, the biasing member 312 biases the piston 310 proximally. For example, in certain configurations, the biasing member 312 encourages the piston 310 proximally such that the protrusions 374 of the piston 310 abut or otherwise engage the shoulder 359 of the intermediate member 308, thereby inhibiting further proximal movement of the piston 310. In some embodiments, a distance between a distal-most edge of the flange 375 and a proximal-most edge of the ribs 327 that extend generally outwardly along the shoulder 325 is less than or equal to a distance between a proximal surface of a partition 383 of the sleeve 316 and the proximal end 372 of the piston 310.

During a blood collection procedure, the device 300 can be engaged with a medical connector (not shown). For example, the medical connector interface 324 can be rotated into threaded engagement with a needleless IV access device or any other type of needleless port or access device. In some configurations, when the medical connector interface 324 is engaged with the medical connector, the needle 302 is in fluid communication with the medical connector and associated systems (e.g., the venous system of the patient in which the IV is disposed), thereby allowing blood or other fluids to flow into the needle 302 via the distal aperture 323 and hollow body 320. In some implementations, the device 300 is placed into the ready-to-operate state (e.g., as shown in FIG. 33) before being engaged with the medical connector. For example, the sleeve 316 can be engaged with the intermediate member 308 prior to the medical connector interface 324 being engaged with the medical connector.

In certain embodiments, when a blood collection vial is not engaged with the device 300, blood or other fluids in the needle 302 are inhibited or prevented from escaping from the device 300 by the boot 314. For instance, the boot 314 can be configured to inhibit or prevent blood or other fluids from escaping from the device 300 after the medical connector interface 324 has been engaged with the medical connector but before a blood collection vial has been engaged with the device 300. In some embodiments, the boot 314 is connected with the proximal end 322 of the connector member 306 such that blood or other fluids in the needle 302 are inhibited or prevented from passing therebetween and/or from separating the boot 314 from the proximal end 322.

Figure 35:
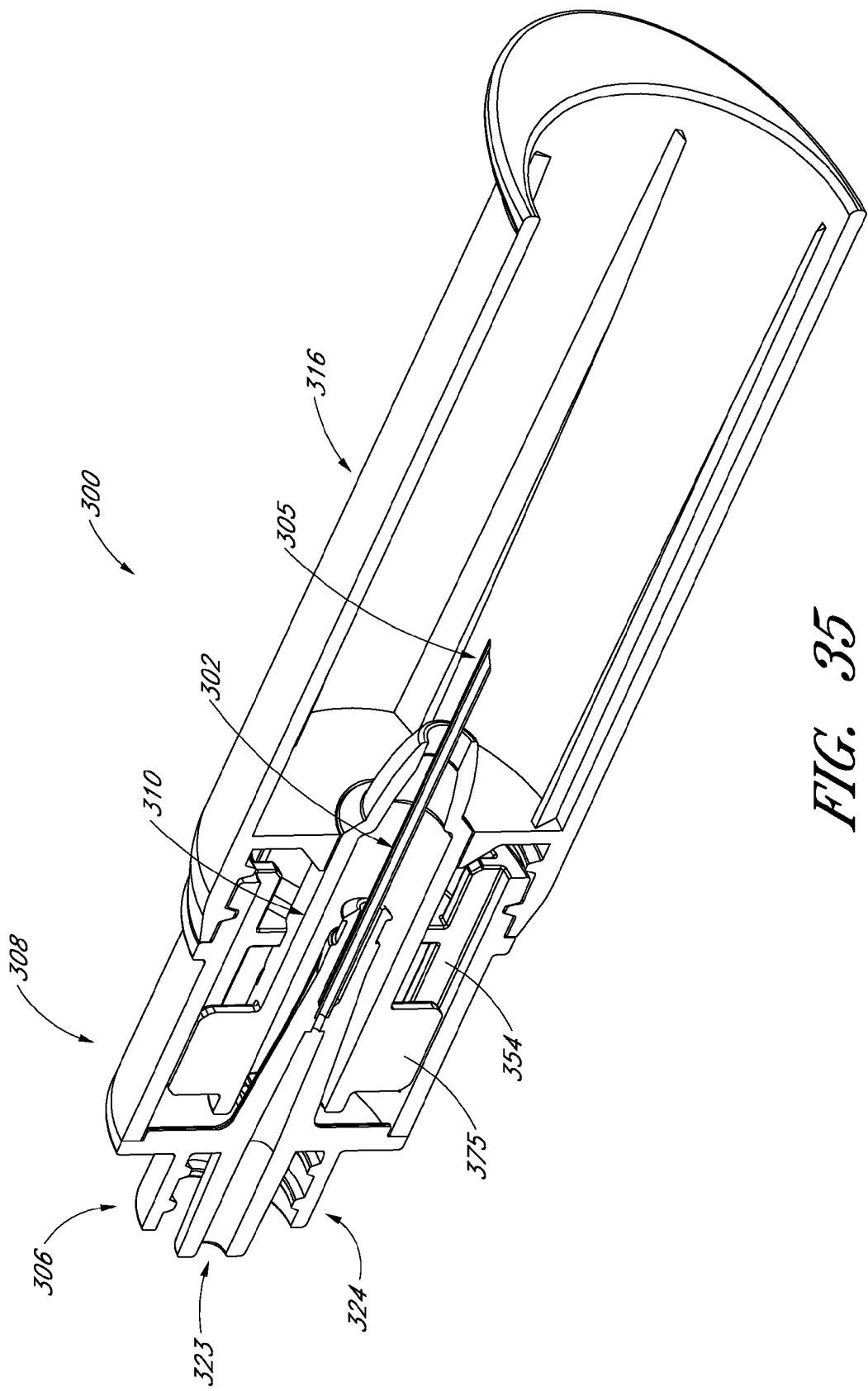
FIG. 35 illustrates a cross-sectional perspective view of the device of FIG. 33 during a blood collection portion of a blood collection procedure.

In some implementations, after the device 300 has been engaged with the medical connector, the blood collection portion of the procedure generally begins. With reference to FIG. 35, during the blood collection portion of the procedure, a distal end of the blood collection vial (not shown) can be abutted with the proximal end 372 of the piston 310. In some instances, the user applies distal force to the blood collection vial, which in turn applies distal force to the piston 310 against the bias of the biasing member 312. The distal force on the piston 310, if sufficiently large, can overcome the bias of the biasing member 312. Further, sufficient distal force on the piston 310 can result in the resilient arms 358 of the intermediate member 308 being disengaged (e.g., being deflected radially outward) from the distal notch 377' of the piston 310. Accordingly, the piston 310 can be moved distally relative to the needle 302.

In some embodiments, distal movement of the piston 310 results in the boot 314 being pressed against the blood collection vial. Continued distal force can result in the proximal end 305 of the needle 302 piercing the boot 314 and passing into the blood collection vial. Thus, blood can flow from the medical connector and associated systems (e.g., the patient's vein) into the blood collection vial via the needle 302. In certain variants, the flow of blood is encouraged by the blood collection vial being evacuated (e.g., under a vacuum).

In some embodiments, when the distal end of the vial is moved distally a distance toward the partition 383 of the sleeve 316, the resilient arms 358 of the intermediate member 308 engage with the proximal notch 377 of the piston 310. In certain embodiments, engagement of the resilient arms 358 and the proximal notch 377 can at least partly counteract the force of the biasing member 312, which can reduce or eliminate the amount of distal force that the user needs to apply to the vial to maintain it in position in the device 300. Such a configuration can, for example, reduce the likelihood of the piston 310 and/or the vial being inadvertently moved proximally by the biasing member 312, which could result in a spill or aspiration of blood. In some variants, the resilient arms 358 and the proximal notch 377 engage when the distal end of the vial is near (e.g., less than or equal to about 5 mm, about 7 mm, or about 10 mm) or abutted against the partition 383 of the sleeve 316.

In various embodiments, if further samples of blood are desired, the vial can be disengaged from the device 300 by moving the vial 300 proximally, thereby extracting the proximal end 305 of the needle 302 from the vial. In certain implementations, when the vial is moved proximally, the biasing member 312 will encourage the piston 310 proximally. In some embodiments, removal of the vial allows the piston 310 and/or the boot 314 to generally return to the ready-to-operate position (e.g., having a portion disposed proximal of the proximal end 305 of the needle 302). In certain implementations, as the vial is removed from the device 300, the resilient arms 358 of the intermediate member 308 re-engage with the distal notch 377' of the piston 310, which can provide a slight resistance against incidental contact with the piston 310. After disengagement of the vial, another vial or vials can be engaged with the device 300.

In some embodiments, after the desired number of samples has been collected, the vial can be disengaged from the device 300 and the device 300 can be disengaged from the medical connector. For example, the medical connector interface 324 can be rotated out of threaded engagement with a needleless IV access device. In certain implementations, after the device 300 has been disengaged from the medical connector, the sleeve 316 is removed from the intermediate member 308, such as by unscrewing the threaded connection. In some embodiments, removal of the sleeve 316 disengages the wedge 385 from the struts 357 of the intermediate member 308. In certain implementations, such disengagement results in the struts 357 of the intermediate member 308 re-engaging with the windows 366 of the piston 310, thereby generally locking the piston 310 (e.g., inhibiting further distal movement), which can reduce the likelihood of a person being stuck with the proximal end 305 of the needle 302.

Furthermore, similar to the sleeve 216 of the device 200 and the discussion above in connection with FIG. 27, in some embodiments, the sleeve 316 can be disposed of as standard waste or non-"sharps" waste. Removal of the sleeve 316 can reduce the weight of the device 300 that is disposed of as "sharps" waste, which in turn can reduce the cost to dispose of the device 300. In some embodiments, a method of manufacturing or providing a blood connection device 300 can include instructing healthcare providers and/or patients to dispose of a portion of the device 300 in a "sharps" receptacle and to dispose of another portion of the device 300 in an ordinary and/or conventional medical refuse receptacle.

Some embodiments of device 300 may be configured for disposal as hazardous waste or other non-"sharps" waste. Certain variants may be disposable as non-"sharps" waste at least partly due to the needle 302 being substantially, substantially entirely, or entirely contained in the device 300 after the device 300 has been used (e.g., in a blood collection procedure), thereby greatly reducing or eliminating the potential of the needle 302 to pierce or rupture the disposal container (e.g., a plastic bag or cardboard box) and/or to produce skin laceration or puncture injuries. Some variants of the device 300 may be disposable as non-"sharps" waste because, for example, the device 300 can automatically and passively secure the piston 310 after the device 300 has been used.

In certain configurations, portions of the device 300 can form a protective enclosure around the needle 302, thereby reducing or eliminating the need for disposing the device 300 in a separate "sharps" container. For example, the connector member 306, intermediate member 308, and piston 310 can form a protective enclosure around the needle 302 after the device 300 has been used. In certain embodiments, the protective enclosure may render the device 300 suitable for disposal as non-"sharps" waste, such as hazardous waste. In some variants, the connector member 306 and/or piston 310 include sealing elements (e.g., a resilient flap, septum, or otherwise) that are configured to generally seal the distal aperture 323 of the connector member 306 and/or the hollow proximal end 372 of the piston 310 at least after the device 300 has been used, thereby reducing the possibility of fluid (e.g., blood) from the needle 302 leaking from the device 300.

In certain embodiments, before, during, or after assembly, the blood collection safety device 100-100c, 200, 300 is cleaned and/or sterilized. In some variants, the blood collection safety device 100-100c, 200, 300 is individually packaged. In some implementations, a blood collection kit comprises the blood collection safety device 100-100c, 200, 300 and a surface prepatory supply, such as a wipe comprising a disinfectant, antiseptic, or other sanitizing agent. Some variants of the kit also include a blood collection vial.

Although the safety device has been disclosed in the context of certain preferred embodiments and examples for blood collection, it will be understood by those skilled in the art that the device extends beyond the specifically disclosed embodiments to other alternative embodiments and/or uses of the invention and obvious modifications and equivalents thereof. For example, the locking and/or reuse inhibiting features could be used in a variety of medical and non-medical fields. Within the medical field, the device can be used in applications or uses that are separate from and/or do not involve blood collection. It should be understood that various features and aspects of the disclosed embodiments can be combined with or substituted for one another in order to form varying modes of the blood collection safety device. Thus, it is intended that the scope of the device herein-disclosed should not be limited by the particular disclosed embodiments described above, but should be determined only by a fair reading of the claims that follow.

The following is claimed:

1. A blood collection safety device, comprising:
a housing comprising a motion regulating frame, a chamber, and a longitudinal axis;
a needle comprising a proximal tip and a distal tip;
a proximal needle cover comprising a ramp and configured to move relative to the housing between an engaged position and a disengaged position, the engaged position being at least partly distal of the disengaged position, the disengaged position configured such that the proximal tip of the needle is positioned distal of a portion of the proximal needle cover;
a distal needle cover comprising a guiding member and configured to move relative to the housing between a retracted position and an extended position, the distal needle cover being positioned proximal of the distal tip of the needle in the retracted position, the distal needle cover being positioned distal of the distal tip of the needle in the extended position; and
a locking member comprising a wing configured to engage the motion regulating frame to retain the distal needle cover in the retracted position,
wherein the ramp of the proximal needle cover and the guiding member of the distal needle cover are configured to engage as the proximal needle cover is moving to the engaged position, thereby rotating the locking member relative to the motion regulating frame and releasing the distal needle cover to move distally toward the extended position.

2. The blood collection safety device of claim 1, wherein the locking member extends radially outward.

3. The blood collection safety device of claim 1, wherein the locking member is connected with a distal portion of the distal needle cover.

4. The blood collection safety device of claim 1, wherein the motion regulating frame of the housing further comprises a notch.

5. The blood collection safety device of claim 1, wherein the locking member further comprises a circumferentially extending winglet configured to engage the housing.

6. The blood collection safety device of claim 1, further comprising a reuse prevention member configured to engage the distal needle cover to inhibit proximal movement of the distal needle cover after the distal needle cover has moved to the extended position.

7. The blood collection safety device of claim 1, wherein the guiding member comprises a foot.

8. The blood collection safety device of claim 1, wherein the ramp extends along a portion of a helical path about the longitudinal axis.

9. The blood collection safety device of claim 1, wherein the proximal needle cover is configured to be pushed to the engaged position by a blood collection vial.

10. The blood collection safety device of claim 1, further comprising a distal tooth that passively secures the distal needle cover in the extended position.

11. The blood collection safety device of claim 10, further comprising a proximal tooth that passively secures the proximal needle cover in the disengaged position.

12. The blood collection safety device of claim 11, wherein the distal tooth and the proximal tooth extend radially inward.

13. The blood collection safety device of claim 1, further comprising a sleeve having an opening configured to receive a proximal end of the proximal needle cover.

14. The blood collection safety device of claim 13, wherein the sleeve is removably connected with the housing.

15. The blood collection safety device of claim 14, wherein the sleeve is configured such that connecting the sleeve with the housing deflects a tooth that secures the proximal needle cover in the disengaged position.

16. The blood collection safety device of claim 1, wherein a portion of the distal needle cover is received in the proximal needle cover during the engagement of the ramp and the guiding member.

17. The blood collection safety device of claim 1, wherein the distal needle cover further comprises the locking member.

18. The blood collection safety device of claim 1, wherein the rotation of the locking member is about the longitudinal axis.

19. The blood collection safety device of claim 1, further comprising a resilient boot that receives the proximal tip of the needle.

20. The blood collection safety device of claim 1, further comprising a flash assembly that indicates the presence of blood, the flash assembly comprising a filter that allows air to pass therethrough but inhibits the passage of blood therethrough.

21. The blood collection safety device of claim 20, wherein the filter is opaque and changes color after contacting blood.

* * * * *